(12) United States Patent
Kim et al.

(10) Patent No.: US 11,191,801 B2
(45) Date of Patent: Dec. 7, 2021

(54) PHARMACEUTICAL COMPOSITION FOR PREVENTING OR TREATING DIABETIC COMPLICATIONS AND ANGIOEDEMA, CONTAINING NATURAL MIXTURE EXTRACT AS ACTIVE INGREDIENT

(71) Applicant: KOREA INSTITUTE OF ORIENTAL MEDICINE, Daejeon (KR)

(72) Inventors: Jin Sook Kim, Seoul (KR); Junghyun Kim, Daejeon (KR); Chan-Sik Kim, Daejeon (KR); Eunjin Shon, Daejeon (KR); Yun Mi Lee, Daejeon (KR); Sojin Choi, Daejeon (KR); Ik Soo Lee, Daejeon (KR); Young Sook Kim, Daejeon (KR); Dong Ho Jung, Daejeon (KR); Bo-Jeong Pyun, Daejeon (KR); Seung-Hyun Jung, Daejeon (KR)

(73) Assignee: KOREA INSTITUTE OF ORIENTAL MEDICINE, Daejeon (KR)

( * ) Notice: Subject to any disclaimer, the term of this patent is extended or adjusted under 35 U.S.C. 154(b) by 632 days.

(21) Appl. No.: 15/313,341

(22) PCT Filed: May 21, 2015

(86) PCT No.: PCT/KR2015/005117
§ 371 (c)(1),
(2) Date: Dec. 22, 2016

(87) PCT Pub. No.: WO2015/178703
PCT Pub. Date: Nov. 26, 2015

(65) Prior Publication Data
US 2017/0182107 A1    Jun. 29, 2017

(30) Foreign Application Priority Data

May 23, 2014  (KR) .................. 10-2014-0062265
May 23, 2014  (KR) .................. 10-2014-0062266

(51) Int. Cl.
*A61K 36/54*    (2006.01)
*A61K 36/65*    (2006.01)

(52) U.S. Cl.
CPC ............. *A61K 36/65* (2013.01); *A61K 36/54* (2013.01)

(58) Field of Classification Search
None
See application file for complete search history.

(56) References Cited

U.S. PATENT DOCUMENTS

2004/0142049 A1    7/2004  Mae et al.
2012/0219649 A1*   8/2012  Rathod ................ A61K 36/482
                                                         424/774

FOREIGN PATENT DOCUMENTS

| CN | 1772261 A | * 5/2006 |
| CN | 101112468 | 1/2008 |
| CN | 101543621 | 9/2009 |
| CN | 101983699 | 3/2011 |
| CN | 102000278 | 4/2011 |
| CN | 102813780 | 12/2012 |
| CN | 103599302 | 2/2014 |
| CN | 103656528 | 3/2014 |
| DE | 102006018972 | 10/2007 |
| JP | 2007211003 | 8/2007 |
| KR | 10-2010-0108031 | 10/2010 |

OTHER PUBLICATIONS

GFCherbs 2019, https://www.gfcherbs.com/Images/Cinnamon%20Twig%20Monograph.pdf.*
"Chinese medicinal herb preparation e.g. for treating diabetes, prepared from prepared rhizome of Rehmannia, white peony roots, rhubarb, Baikal skullcap roots, notoginseng, *Cimicifuga foetida*, barbed skullcap herb, and cassia twig," WPI/Thomson, vol. 2009, Sep. 23, 2009.
Database TCM, Wang Chaoqun: "A skin caring and pox removing composition and its preparation methods," XP002776146, Aug. 12, 2009.
Database WPI Week 201133 Thomas Scientific, London, GB; AN 2011-E32556 XP002776147, Mar. 9, 2011.
Luo et al., "Identification of Compounds from the Water Soluble Extract of *Cinnamomum cassia* Barks and Their Inhibitory Effects against High-Glucose-Induced Mesangial Cells," *Molecules*, 18(9):10930-10943, (2013).
Supplementary European Search Report issued in European Application No. 15796502.1, dated Jan. 12, 2018.

(Continued)

*Primary Examiner* — Terry A McKelvey
*Assistant Examiner* — Catheryne Chen
(74) *Attorney, Agent, or Firm* — Norton Rose Fulbright US LLP

(57) ABSTRACT

The extract of a mixture of cinnamon twig and moutan root bark, cinnamon twig and peony root, or cinnamon twig and poria according to the present invention has been confirmed to inhibit the excessive generation of advanced glycation end-products, which occurs under chronic diabetic conditions, exhibit the effect of fragmentizing a cross-link between the advanced glycation end-products and matrix proteins, have an excellent effect in inhibiting the generation of the advanced glycation end-products in a human retinal pigment epithelial cell line subjected to a hyperglycemic or aging environment, and have excellent effects in delaying, preventing, and treating diabetic complications, muscular degeneration, commotio retinae, and lower extremity edema in various animal models of diabetic complications, macular degeneration, and lower extremity edema, and thus the mixture extract can effectively be used as an active ingredient for a composition for preventing and treating diabetic complications, including diabetic retinopathy, diabetic nephropathy, and diabetic neuropathy, and angioedema, including macular (retinal) edema, macular degeneration, and varicose veins.

10 Claims, 23 Drawing Sheets

(56) References Cited

OTHER PUBLICATIONS

Figure 1A:
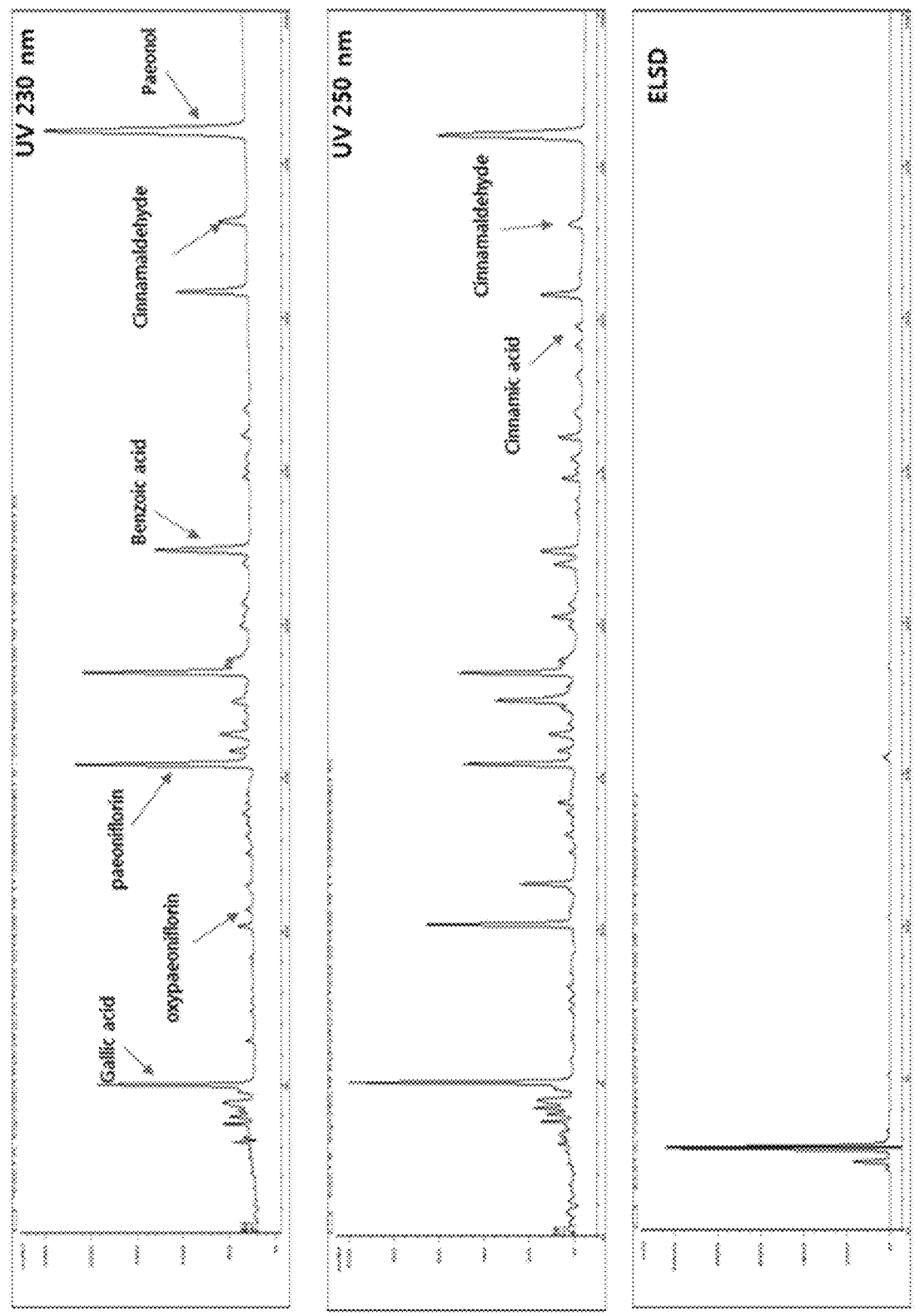

Wong et al., "Anti-inflammatory and analgesic effects and molecular mechanisms of JCICM-6, a purified extract derived from an anti-arthritic Chinese herbal formula," *Phytomedicine*, 15(6-7):416-426, (2008).
Zhang et al., "The anti-inflammation effect of Moutan Cortex on advanced glycation end products-induced rat mesangial cells dysfunction and High-glucose-fat diet and streptozotocin-induced diabetic nephropathy rats," *Journal of Ethnopharmacology*, 151(1):591-600, (2013).
Hao, et al. "Chinese Herbal Medicine for Diabetic Peripheral Neuropathy: An Updated Meta-Analysis of 10 High-Quality Randomized Controlled Studies" *PLoS ONE*, Oct. 2013, 8(10), e76113, pp. 1-13.
"Urticaria—Treatment with Chinese herbs for Urticaria symptoms" TCM Assistant, (http://web.archive.org/web/20130918130658/http://tcmassistant.com/symptoms/urticaria.html/) accessed Jun. 25, 2015.
Ha, et al. "Inhibitors of Aldose Reductase and Formation of Advanced Glycation End-Products in Moutan Cortex (*Paeonia suffruticosa*)" *J. Nat. Prod.* 2009, 72, 1465-1470.
Jin and Cho "Water extracts of cinnamon and clove exhibits potent inhibition of protein glycation and anti-atherosclerotic activity in vitro and in vivo hypolipidemic activity in zebrafish" *Food and Chemical Toxicology* 49 (2011) 1521-1529.
Brownlee, Michael "Biochemistry and molecular cell biology of diabetic complications" *Nature* 414, Dec. 13, 2001, pp. 813-820.
Brownlee, et al. "Advanced Glycosylation End Products in Tissue and the Biochemical Basis of Diabetic Complications" *N Engl J Med* 1988; 318; 1315-1321 (abstract only).
Yokozawa, et al. "Effects of Oriental medicines on the production of advanced glycation endproducts" *Journal of Traditional Medicines* 18, 107-112, 2001.
Sobrin and Seddon "Nature and nurture—genes and environment—predict onset and progression of macular degeneration" *Progress in Retinal and Eye Research* 40 (2014) 1-15.
Zampatti, et al. "Review of nutrient actions on age-related macular degeneration" *Nutrition Research* 34 (2014) 95-105.
Kay, et al. "Age-Related Changes of Cystatin C Expression and Polarized Secretion by Retinal Pigment Epithelium: Potential Age-Related Macular Degeneration Links" *IVOS* Feb. 2014 55(2), pp. 926-934.
Lee, Hoi-Seon, "Inhibitory Activity of *Cinnamomum cassia* Bark-Derived Component against Rat Lens Aldose Reductase," *J. Pharm Pharmaceut Sci.*, 2002; 5(3): 226-230.
Su et al., "Effects of Total Glucosides of Paeony on Oxidative Stress in the Kidney from Diabetic Rats," *Phytomedicine*, 2010; 17: 254-260.
Official Communication Issued in Corresponding European Patent Application No. 15796502.1, dated Jul. 23, 2019.
Office Action Issued in Corresponding Chinese Patent Application No. 201580039444.9, dated Nov. 5, 2019.
Zhan, Wenguo "All About Clinical Use of Gui-Zhi-Fu-Ling-Wan," Gansu Medical Journal, 31(10): 766-768, 2012.
Luo Hesheng, et al. "Immunological Pharmacology and Clinical Medicine of Chinese Medicine," ISBN: 7-81031-864-7, Beijing Medical University, China Peking Union Medical University Joint Press, pp. 241-242, Apr. 1999, Beijing. (English Abstract only).
Office Action issued in Corresponding Chinese Application No. 201580039444.9, dated Feb. 5, 2021 (No English Translation provided).

\* cited by examiner

Preventive effect against acellular capillary formation

*p<0.05 vs NOR;
p<0.05 vs DM

Fig. 6

| Preventive effect against damage of occludin, tight-junction protein between cells ||||
|---|---|---|---|
| Normal Group | Diabetic Group | FENO | CPA4-1-100 |
| CPA4-1-250 | CMO4-1-100 | CMO4-1-250 | |

Therapeutic effect on blood-retinal barrier damage in each week

Therapeutic effect on acellular capillary formation

| Therapeutic effect on damage of claudin-5, tight-junction protein between cells ||||
|---|---|---|---|
| Normal Group | Diabetic Group | MET | MET+FENO |
|  |  |  |  |
| MET+CMO4-100 | MET+CMO4-250 | MET+CPA4-100 | MET+CPA4-250 |
|  |  |  |  |

Inhibitory effect against mesangial expansion

Inhibitory effect against expansion of mesangial extracellular matrix

PHARMACEUTICAL COMPOSITION FOR PREVENTING OR TREATING DIABETIC COMPLICATIONS AND ANGIOEDEMA, CONTAINING NATURAL MIXTURE EXTRACT AS ACTIVE INGREDIENT

CROSS-REFERENCE TO RELATED APPLICATIONS

This application is a national phase application under 35 U.S.C. § 371 of International Application No. PCT/KR2015/005117 filed May 21, 2015, which claims priority to Korean Patent Application No. 10-2014-0062265 filed May 23, 2014 and Korean Patent Application No. 10-2014-0062266 filed May 23, 2014. The entire contents of each of the above-referenced applications are incorporated into the present application by reference.

TECHNICAL FIELD

The present invention relates to a pharmaceutical composition for preventing and treating diabetic complications including diabetic retinopathy, diabetic nephropathy, and diabetic neuropathy, and angioedema including macular (retinal) edema, macular degeneration, and varicose veins, wherein the composition contains an extract of a mixture of cinnamon twig and moutan root bark, cinnamon twig and peony root, or cinnamon twig and poria as an active ingredient.

BACKGROUND ART

According to a report by the Journal of the American Medical Association (JAMA) in 2009, the global diabetes population has already surpassed 240 million, and the number of diabetics globally is expected to grow to 380 million in 2025, and among these, about 60% will occur in the region of Asia. In particular, with the recent advent of an aging society and the continuous decrease of the onset age of diabetes, the onset of diabetic complications is rapidly increasing. Recently, the prevalence rate of diabetes has reached 10% in Korea. In particular, the onset of diabetes has advanced to young adults, and the number of patients with diabetic complications is explosively increasing due to increased life expectancy.

Occurrence of diabetic complications has increased by 60% over the past five years, and medical expenses have also increased by 54%. As a result, the medical expenses have ultimately reached 203.5 billion Korean won (National Health Insurance Corporation; August, 2011). That is, almost all organs in the body are damaged 10 to 15 years after the onset of diabetes, resulting in diabetic retinopathy, diabetic cataract, diabetic nephropathy, diabetic neuropathy, diabetic foot ulcers, diabetic heart disease, diabetic osteoporosis, or diabetic arteriosclerosis.

Although diabetes drugs having several mechanisms, e.g., Metformin, Rosiglitazone, Zemiglo, Januvia, etc., that are currently administered to a diabetic regulate the blood glucose level of early diabetes, the diabetes drugs cannot fundamentally prevent or treat the transition to onset diabetic complications (diabetic ophthalmopathy, nephropathy, neuropathy, foot ulcers, etc.), which occur by chronic progresses, due to the impossibility of complete recovery. Diabetic complications begin with diabetes, but the mechanisms of transition thereto are different from diabetes itself. Therefore, it is necessary to delay, prevent, or treat diabetic complications by jointly using drugs capable of delaying or preventing diabetic complications while also rapidly regulating the blood glucose.

Chronic diabetic nephropathy requires hemodialysis and organ transplantation, and diabetic cataract and retinopathy cause blindness. In the United States, it was reported that the main cause of blindness in the ages of 25 to 74 is diabetes. For patients with diabetic foot ulcers, they may have to suffer from the horrible situation of amputation of their arms and legs, and diabetic neuropathy is accompanied by a feeling of stabbing pain. In addition, diabetic heart disease causes sudden death. Therefore, when the onset of diabetic complications in diabetic patients can be delayed even for several years, the quality of life of the patients and their families will be changed, and it will greatly help the national finance.

It was reported that representative factors inducing these diabetic complications include production of advanced glycation end-products, activation of aldose reductase, activation of PKC isomers, and increase of hexosamine pathway flux (Nature, 414, 813-820, 2000; Diabetologia, 38: 357-394, 1995). Oxidative stress is accelerated by irreversible reaction of these factors, thereby further exacerbating diabetic complications.

Non-enzymatic glycation of a protein indicates a condensation reaction of a reducing sugar and an amino acid group such as a lysine residue of a protein without being mediated by an enzyme (Maillard reaction). As a result of this reaction, advanced glycation end-products (AGEs) are generated. That is, it forms a Schiff base as an early stage product, and then ketoamine adducts residing near the Schiff base react therewith to produce reversible Amadori-type early glycation products; and when a hyperglycemic status persists, the reversible Amadori-type early glycation products are not degraded but only rearranged to produce irreversible advanced glycation end-products. The generated irreversible advanced glycation end-products are conjugated or cross-linked with proteins or lipids, leading to the irreversible production of glycoproteins or glycolipids. The advanced glycation end-products bind (cross-link) to protein, such as basement membrane, plasma albumin, crystalline lens protein, fibrin, and collagen, or to lipid. Therefore, these are accumulated in tissues during the survival period thereof in order to abnormally change the structure and functions of tissues, thereby inducing complications. Additionally, even if the blood glucose level returns to normal, complications will be developed because the produced advanced glycation end-products continuously react with proteins and lipids (*N. Engl. Med.,* 1988, 318, 1315-1321). Additionally, oxidative stress is induced when the function of defense system against oxygen free radicals declines under the above-described conditions (*J. of Trad. Med.* 2001, 18: 107-112). It was reported that it is important to inhibit production of advanced glycation end-products in order to delay, prevent, or treat the onset of diabetic complications based on such mechanisms (*N. Engl. Med.* 1998, 318, 1315-1321).

Diabetic retinopathy damages blood vessels and nerve cells in a chronic hyperglycemic state, and thus progresses to non-proliferative retinopathy. As a result, it eventually progresses to proliferative retinopathy to cause blindness. That is, in a hyperglycemic state, pericytes that wrap around capillaries of the retina begin to break, while a microaneurysm phenomenon occurs, leading to damage to endothelial cells. As a result, numerous acellular capillaries that cannot function as blood vessels are produced. The walls of these abnormal neovessels are weak enough as to be easily destroyed, and thus blood components leak out, eventually leading to vision loss. Several pathological phenomena occur because tight-junction proteins such as occludin or claudin, which link to peripheral cells, endothelial cells, and the like, are damaged. In order to prevent such diabetic retinopathy, the initial symptom, which is damage to peripheral cells, must be prevented. Fenofibrate (Lipidil, Abott) was approved by the Australian FDA in December 2013 as a PPARα agonist, a drug for treating diabetic retinopathy. The ACCORD study and the FILD study reported that while 33% of patients with diabetes who had strict blood glucose control were prevented from transitioning to diabetic retinopathy, about 40% of the patients were delayed from transitioning to diabetic retinopathy.

Iluvien (fluocinolone acetonide intravitreal implant, Alimera Science) was approved by the US FDA in 2014 as a drug for treating diabetic muscular edema.

Diabetic nephropathy acts as an important factor in causing chronic diabetic nephropathy by glycated albumin in which advanced glycation end-products are coupled with proteins. Glycated albumin is more easily introduced into glomerular cells compared to normal albumin, and a chronically high concentration of glucose stimulates mesangial cells in order to increase the synthesis of extracellular matrix. The excessively introduced glycated albumin and the increased extracellular matrix cause the fibrosis of glomeruli. By these mechanisms, the glomeruli are continuously damaged, so that extreme treatments such as hemodialysis and organ transplantation are necessary.

Angioedema refers to a disease in which permeability of the blood vessels located deep inside the skin or underneath the skin, or beneath the mucous membrane is increased, thereby causing the body fluids therein to leak out and gather around the neighboring tissues, e.g., producing edema. Angioedema frequently occurs in relatively loose tissues. It can easily occur around the eyes and lips, or in the hands, mucous membranes such as the tongue, the inside of the mouth, the larynx, or the walls of the gastrointestinal tract. In particular, macular (retinal) edema, macular degeneration, or varicose veins occur due to angioedema causing damage to the blood-retinal barrier.

Age-related macular degeneration (AMD) refers to an irreversible disease, and is a representative disease that develops in numerous senior citizens and induces blindness. The incidence rate thereof is gradually increasing due to an aging global population. In the United States, it was reported that age-related muscular degeneration is the main cause of blindness, and environmental and genetic factors also affect the onset thereof. In particular, smoking was reported as the most fatal onset factor. In addition, obesity and excessive intake of antioxidants and dietary fat also induce macular degeneration and influence further progression thereof. Therefore, the onset of macular degeneration decreases with healthy dietary intake, body weight regulation, proper exercise, smoking cessation, and the like. In the United States, the prevalence rate of early (dry) macular degeneration was merely 3.9% in the 40- to 50-year-old age group, whereas it appeared that the incidence rate thereof was very high at 22.8% in the age group of 75 years and older (Beaver Dam Eye Study). Additionally, elderly people aged 75 years and older showed the incidence rate of 5.4%, and 7.1% thereof were end-stage macular degeneration patients. 1.9% of Australian Caucasians are end-stage macular degeneration patients, and during the five-year period, the incidence rate thereof in young age groups of 55 years and younger was 0%, but 18.5% of the elderly group aged 85 years and older had macular degeneration. In addition, the rates thereof were similar to rates in Asian Malays, an ethnic group of Australia (Blue Mountain Eye Study; *Progress in retinal and eye research*, 1-15, 2014). In Korea, the Korean Retina Society reported that, in the past year, the number of patients with wet macular degeneration was increased by 7.4-fold, and the incidence rate in the 40- to 50-year-old age group was increased by 9-fold. However, the most serious problem is that a treatment for macular degeneration has not been found. Lucentis, produced by Novartis, a Swiss pharmaceutical company, is an antibody therapeutic agent, and is very expensive. In addition, Lucentis is disadvantageous in that visual acuity cannot be recovered enough to stop progression of the disease.

Macular degeneration is classified as dry macular degeneration and wet macular degeneration. Drusen, a mass of waste, is accumulated in the macula and damages the metabolic connection between the choroid and upper part of the macula, thereby developing dry macular degeneration. In addition, when such process continuously progresses, it evolves into wet macular degeneration. That is, since waste is accumulated in the macular region, blood vessels cannot function properly, and thus nutrients, oxygen, and the like cannot be supplied thereto. As a result, it leads to abnormal neovessel growth, which is called choroidal neovascularization (CNV). The thus-generated blood vessels have very weak walls so that proteins, erythrocytes, or the like in the blood vessels leak out to the macular region and retina. In addition, due to a discharge of blood from the blood vessels, several factors occur, such as death of photoreceptors (rods and cones) and retinal pigment epithelial cell layer, etc., thereby leading to blindness (*Nutrition Research*, 34, 95-105, 2014; *Plos one*, 8, e71064, 2013).

Retinal pigment epithelial cells (RPEs) play a significant role in maintaining healthy eyesight by supporting Bruch's membrane (BrM) and by maintaining a non-proliferative status. Cystatin C secreted from retinal pigment epithelial cells is a strong cysteine proteinase inhibitor, and plays an important role in properly regulating protein circulation in BrM. However, excessive accumulation of advanced glycation end-products decreases the expression and secretion of cystatin C, resulting in an imbalance of protein degradation at the base part of retinal pigment epithelial cells. As a result, macular degeneration eventually occurs. Accordingly, it was reported that macular degeneration can also be prevented (treated) by inhibiting the production of advanced glycation end-products (Kay P, et al., *IOVS*, 2014, 55(2), 926-34).

Vascular endothelial growth factor (VEGF) is secreted from the retinal pigment epithelial cell layer to normally adjust the parts around Bruch's membrane (BrM) and to regulate growth and compactness of choroidal capillary endothelial cells. Under normal conditions, the secretion of VEGF is very severely regulated so that neovascularization does not occur. However, if the secretion of VEGF is not severely regulated, it acts as a decisive factor leading to reaching the end-stage of macular degeneration. When the secretion of VEGF is abnormally increased, abnormal and weak blood vessels are produced, thereby destroying the blood vessels (*J. Cell. Mol. Med.*, 17, 7, 833-843, 2013).

Varicose veins are a disease in which a vein appears toward the outside of the skin. Veins distributed in limbs are classified as deep veins, located between muscles, superficial veins, which can be seen below the skin, and perforating veins, connecting these two. Among these, varicose veins refer to veins in which the superficial veins are stretched so that they appear to protrude outside the skin. In addition, when valves that constantly maintain the blood flow in veins in order to always direct towards the heart increase the pressure in the varicose veins, vein walls become weak so that the valves are damaged. As a result, the blood moving toward the heart flows backward so that veins are stretched, thereby causing varicose veins.

Cinnamon twig is a young branch of *Cassia* bark tree (cinnamon tree) which is an evergreen tree, one of several species of *Cinnamomum*. The taste of cinnamon twig is spicy and sweet, the property thereof is warm, and it affects the heart, lungs, and bladder. It is known to strengthen the stomach, inhibit stroke, have pain-relief and cardiotonic actions, expand cutaneous blood vessels, stimulate sweat glands to induce perspiration so that an antipyretic action is applied to the body, and have an inhibitory action against viruses. In addition, cinnamon twig is used for treating chills, fever, headache, body aches, palpitations, etc., or used when perspiration is not properly produced. Cinnamon twig has a long cylindrical shape and has numerous branches, the length of which is 30 cm to 70 cm, while the diameter of thicker parts is 0.3 cm to 1 cm. The surface has a vertical ridgeline in a reddish-brown or brown color, and has traces of leaves and branches in the form of thin wrinkles and small lumps. The quality thereof is hard, fragile, and easy to cut. Guangxi and Guangdong Province are the main production areas, and Vietnam, Sri Lanka, India are the nations where cinnamon twigs are cultivated. According to the results of pharmacological experiments on cinnamon twig, it was revealed that the cinnamon twig has perspiration, antipyretic, analgesic, cardiotonic, anti-allergic, and antiviral effects. However, effects related to diabetic complications or angioedema of cinnamon twig have not been revealed.

Moutan root bark is an important herbal medicine which has been used since long ago, and is used as an antiphlogistic coagulant treating blood extravasation for oriental medicine due to its cold property. In addition, its medicinal effect is used for inflammation in vascular systems of lower abdominal organs, pains due to congestion, fever, suppuration, bleeding, and the like. In particular, moutan root bark has effects on anti-inflammation, contraction, spasmolysis for menstrual irregularity, inflammation in the uterus and adnexa, congestion, and dragging pain, and is also applied to treat hemorrhoids and epityphlitis.

Peony root is a perennial belonging to the family Ranunculaceae, and is classified as *Radix paeoniae alba* and *Radix paeoniae rubra*. *Radix paeoniae alba* and *Radix paeoniae rubra* are determined by the presence of a shell; *Radix paeoniae rubra* is a perennial with a shell; and *Radix paeoniae alba* is a perennial which the shell is peeled off (*Altern. Med. Rev.*, 6 (5), pp 495-499, 2001). *Radix paeoniae alba* and *Radix paeoniae rubra* have anti-contractile and coronary dilatation effects for smooth muscles of the stomach, intestine, and uterus; effects of preventing atherosclerosis, decreasing blood pressure, improving bloodstream, and an antioxidant effect for vascular diseases (Ohsugi M et al., *J. Ethnopharmacol.*, 67, pp 111-119, 1999); a platelet aggregation inhibitory effect (Lin H C et al., *Planta Med*, 65, pp 595-599, 1999); an antithrombotic effect (Ishida H et al., *Chem. Pharm. Bull*, 35 (2), pp 849-852, 1987); and prevention of hyperlipidemia (Yang HO et al., *Fitoterapia*, 75 (1), pp 45-49, 2004). In addition, it was reported that glycoside, which is a part of the constituents of peony root, is effective for treating cerebral infarction (Yang J et al., *Zhong Yao Cai*, 23 (2), pp 95-97, 2000).

Poria refers to *Sclerotium* which grows in pine roots, and has a ball or oval shape with a diameter of 5 cm to 7 cm. In addition, it has a brown or dirty black color and the appearance of pieces of bark on dirt. Poria is hard due to suberization, covered with a thickness of 0.2 mm to 0.5 mm, and radial cracks form. Although poria has little taste and odor, it sometimes spreads with light mucus and shows a positive reaction to iodine. In addition, it is reported that poria is used as a stabilizer, and not only has an effect for stabilizing congenital fever but also warms the body.

Therefore, the present inventors have made efforts to develop a safe and effective natural drug for preventing and treating diabetic complications and angioedema, wherein the natural drug does not have toxicity and side effects. As a result, it was confirmed that the mixed extract of cinnamon twig and moutan root bark, cinnamon twig and peony root, or cinnamon twig and poria inhibits the excessive generation of advanced glycation end-products, which occurs under chronic diabetic conditions, exhibits the effect of fragmentizing a cross-link between the advanced glycation end-products and matrix proteins, has an excellent effect in inhibiting the generation of the advanced glycation end-products in a human retinal pigment epithelial cell line subjected to a hyperglycemic or aging environment, and has excellent effects in delaying, preventing, and treating diabetic complications, macular degeneration, commotio retinae, and lower extremity edema in various animal models of diabetic complications, macular degeneration, and lower extremity edema, and thus the mixed extract can effectively be used as a composition for preventing and treating diabetic complications and angioedema. Accordingly, the present invention is completed.

Technical Problem

An object of the present invention is to provide a composition for preventing and treating diabetic complications and angioedema, containing the mixed extract of cinnamon twig and moutan root bark, cinnamon twig and peony root, or cinnamon twig and poria as an active ingredient.

Technical Solution

In order to achieve the above object, the present invention provides a pharmaceutical composition for preventing and treating diabetic complications and angioedema, containing the extract of a mixture of cinnamon twig and moutan root bark, cinnamon twig and peony root, or cinnamon twig and poria as an active ingredient.

Additionally, the present invention provides a health functional food for preventing and ameliorating diabetic complications and angioedema, containing the mixed extract as an active ingredient.

Additionally, the present invention provides a method for treating diabetic complications and angioedema, comprising a step of administering a pharmaceutically effective amount of the mixed extract to a subject having diabetic complications and angioedema.

Additionally, the present invention provides a method for ameliorating diabetic complications and angioedema, comprising a step of administering a pharmaceutically effective amount of the mixed extract to a subject having diabetic complications and angioedema.

Additionally, the present invention provides a use of the mixed extract as a pharmaceutical composition for preventing and treating diabetic complications and angioedema.

Additionally, the present invention provides a use of the mixed extract for use as a health functional food for preventing and ameliorating diabetic complications and angioedema.

Advantageous Effects

The mixed extract of cinnamon twig and moutan root bark, cinnamon twig and peony root, or cinnamon twig and poria according to the present invention has been confirmed to inhibit the excessive generation of advanced glycation end-products, which occurs under chronic diabetic conditions, exhibit the effect of fragmentizing a cross-link between the advanced glycation end-products and matrix proteins, have an excellent effect in inhibiting the generation of the advanced glycation end-products in a human retinal pigment epithelial cell line subjected to a hyperglycemic or aging environment, and have excellent effects in delaying, preventing, and treating diabetic complications, muscular degeneration, commotio retinae, and lower extremity edema in various animal models of diabetic complications, macular degeneration, and lower extremity edema, and thus the mixed extract can effectively be used as an active ingredient for a composition for preventing and treating diabetic complications, including diabetic retinopathy, diabetic nephropathy, and diabetic neuropathy, and angioedema, including macular (retinal) edema, macular degeneration, and varicose veins.

BRIEF DESCRIPTIONS OF THE DRAWINGS

Figure 1B:
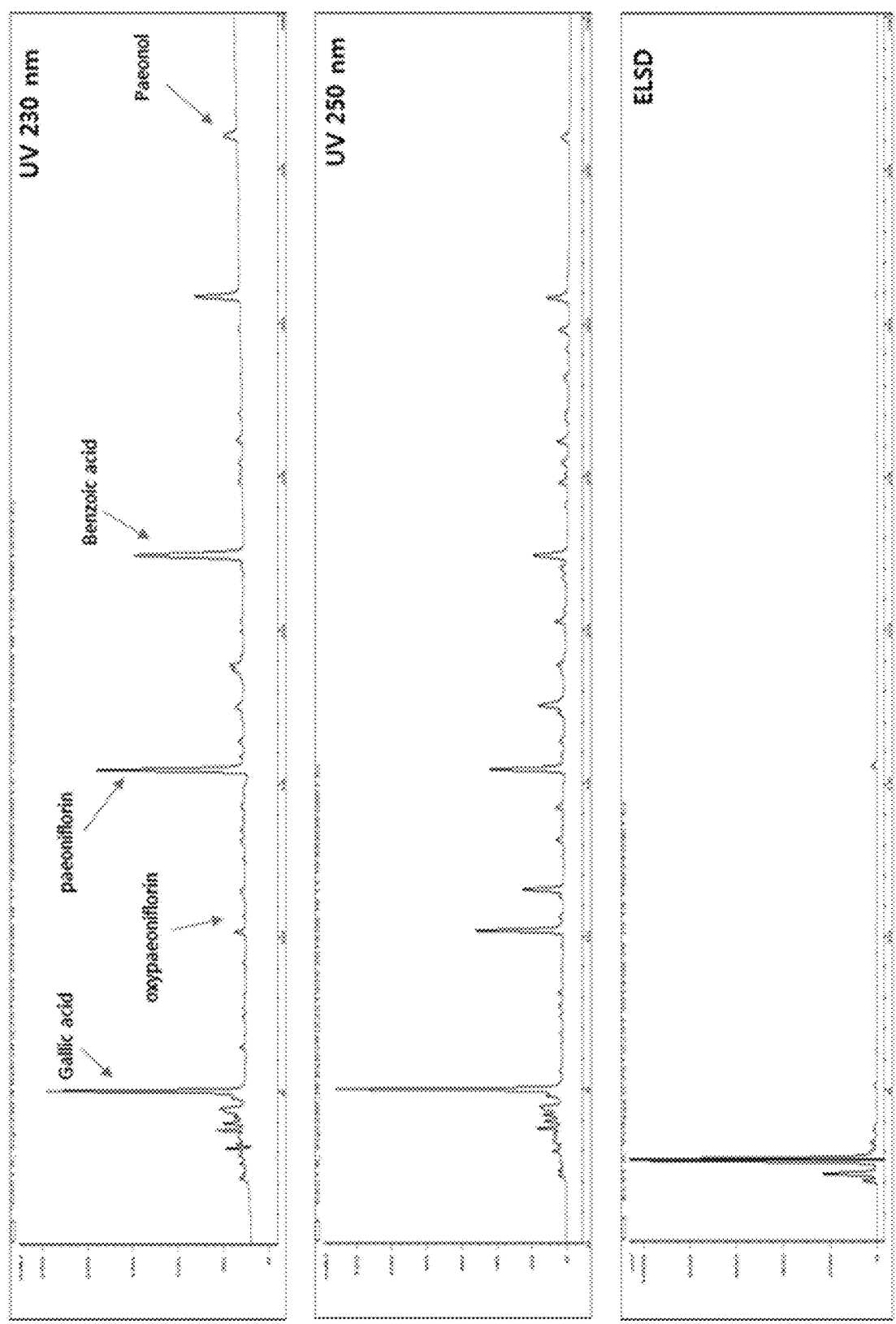
Figure 1C:
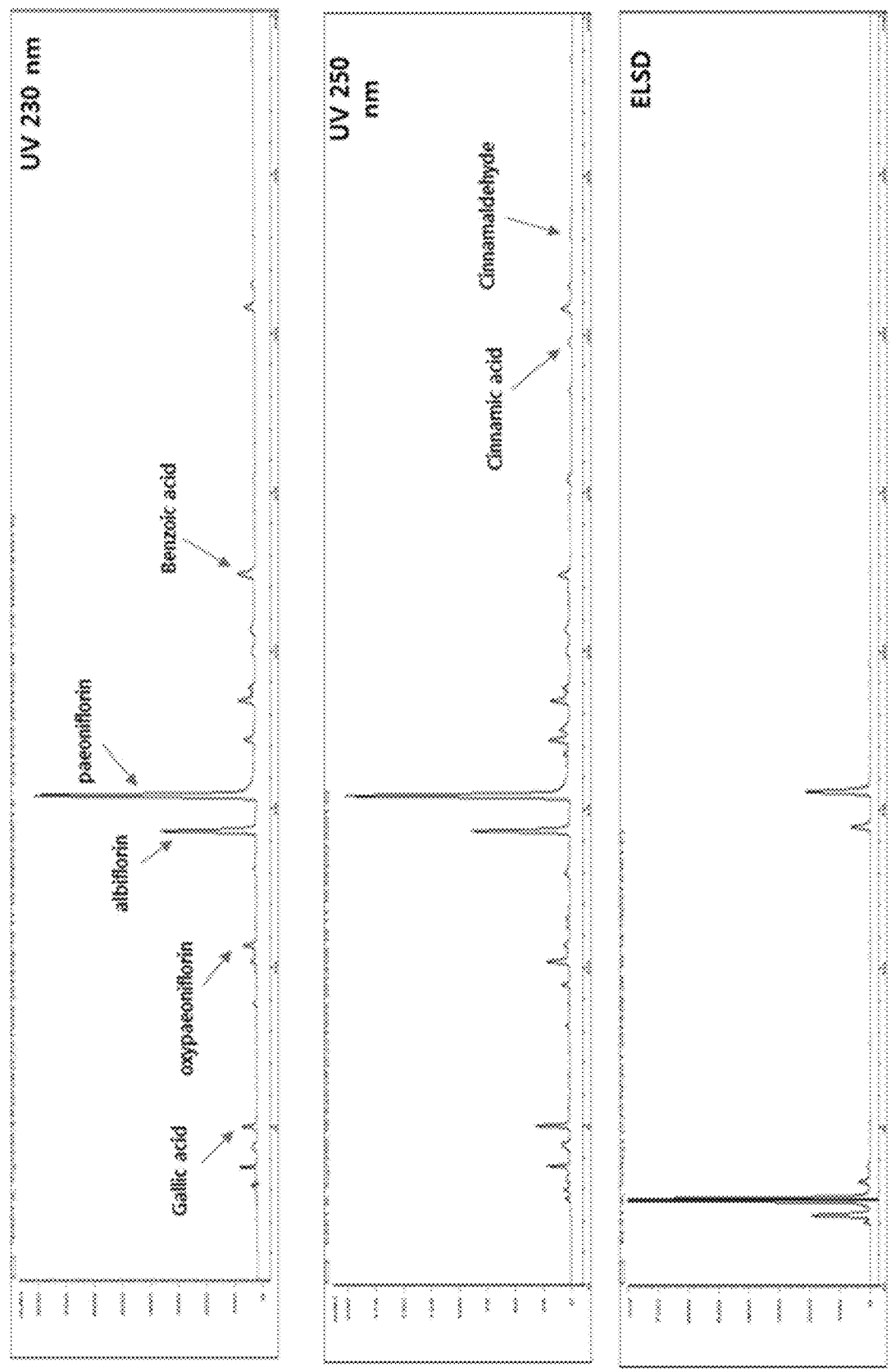
Figure 1D:
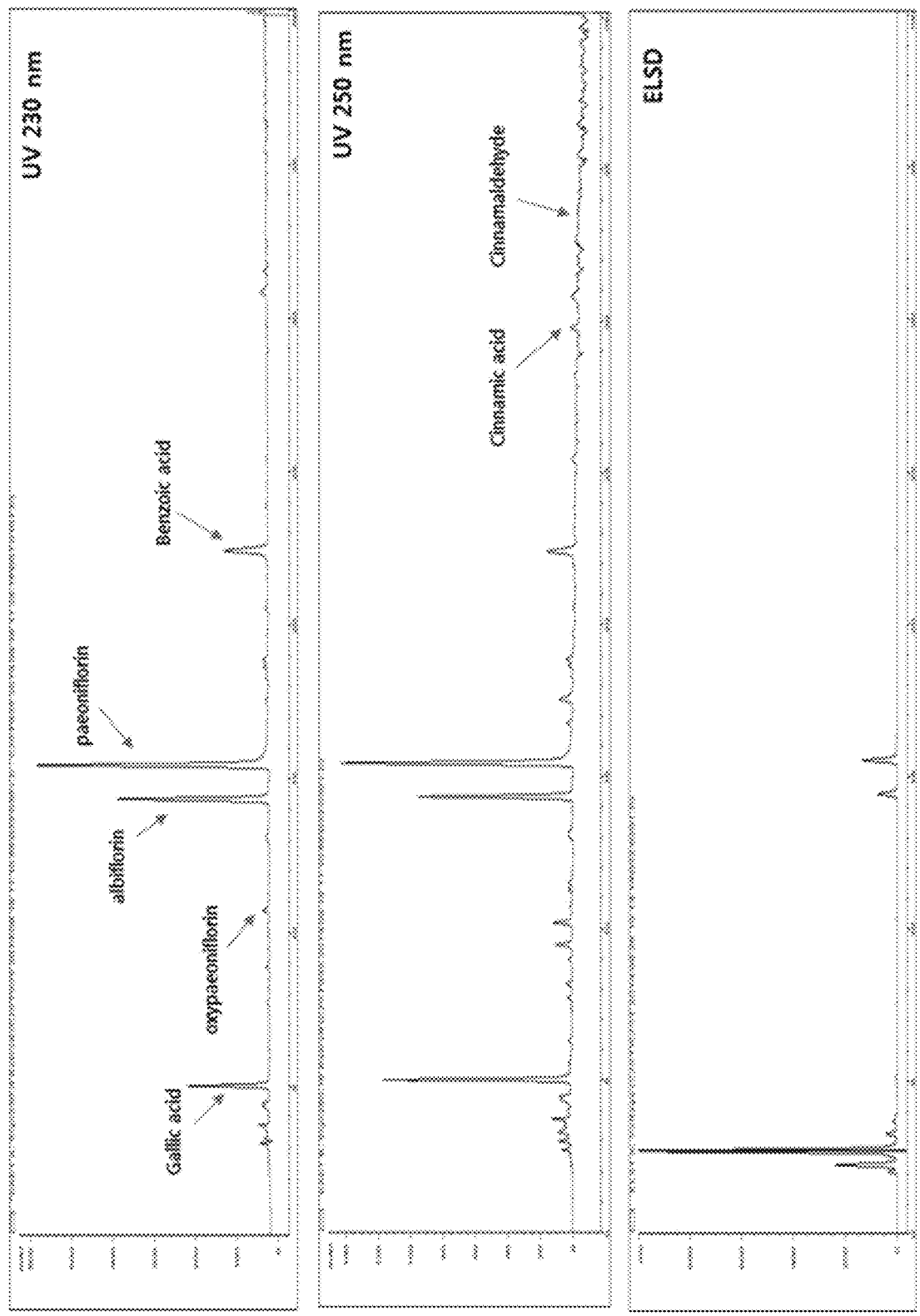

FIG. 1a is a graph showing an analysis result of ingredients for CMO4 (extract of cinnamon twig and moutan root bark (1:8)); FIG. 1b for CMO4-1 (hot water extract of cinnamon twig and moutan root bark (1:8)); FIG. 1c for CPA4 (extract of cinnamon twig and peony root (1:8)); and FIG. 1d for CPA4-1 (hot water extract of cinnamon twig and peony root (1:8)), all analyzed by HPLC.

Figure 2:
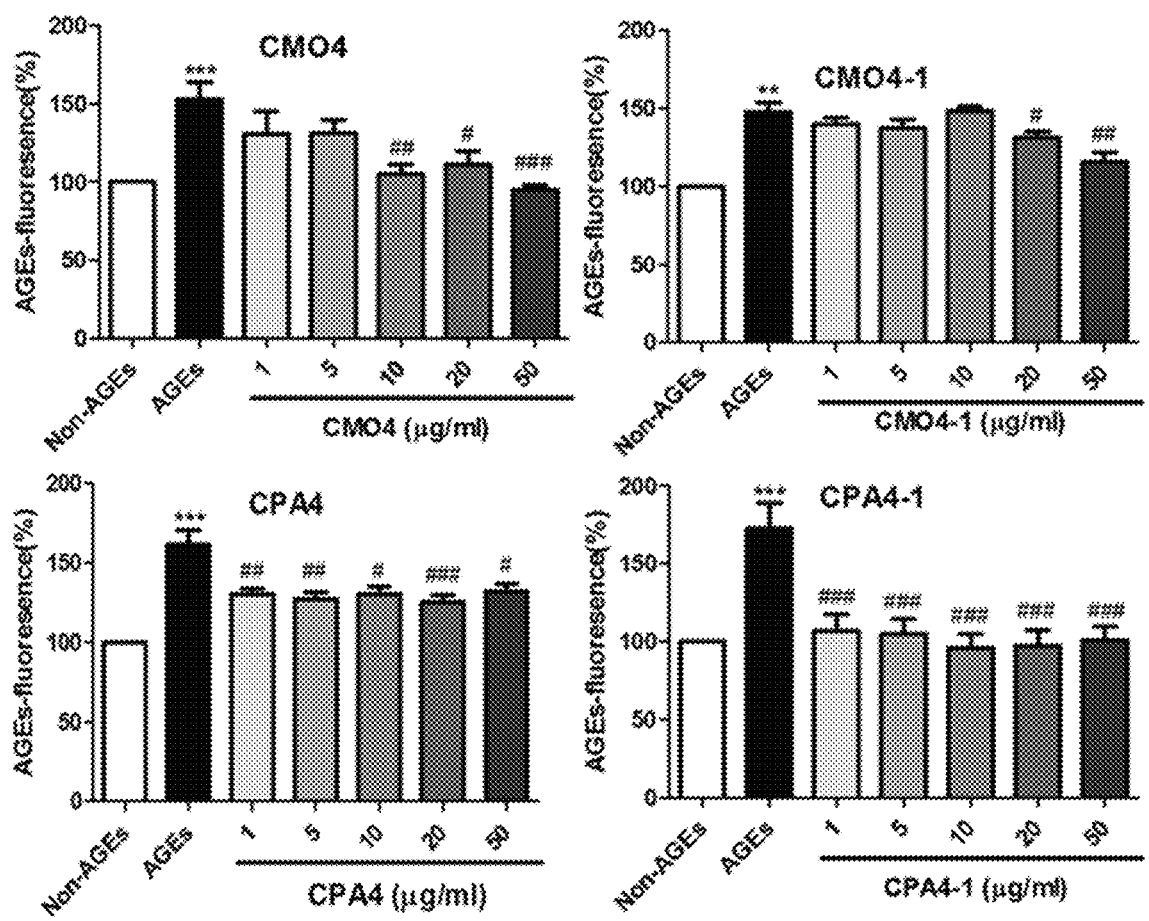

FIG. 2 is graphs confirming an effect of inhibiting production of advanced glycation end-products on extracellular matrix (ECM) treated with glycoaldehyde:
AGEs: advanced glycation end-products;
CMO4: extract of cinnamon twig and moutan root bark (1:8);
CMO4-1: hot water extract of cinnamon twig and moutan root bark (1:8);
CPA4: extract of cinnamon twig and peony root (1:8);
CPA4-1: hot water extract of cinnamon twig and peony root (1:8);
**$p<0.01$ vs. Non-AGEs;
***$p<0.001$ vs. Non-AGEs;
$p<0.05$ vs. AGEs;
$p<0.01$ vs. AGEs; and
$p<0.001$ vs. AGEs.

Figure 3:
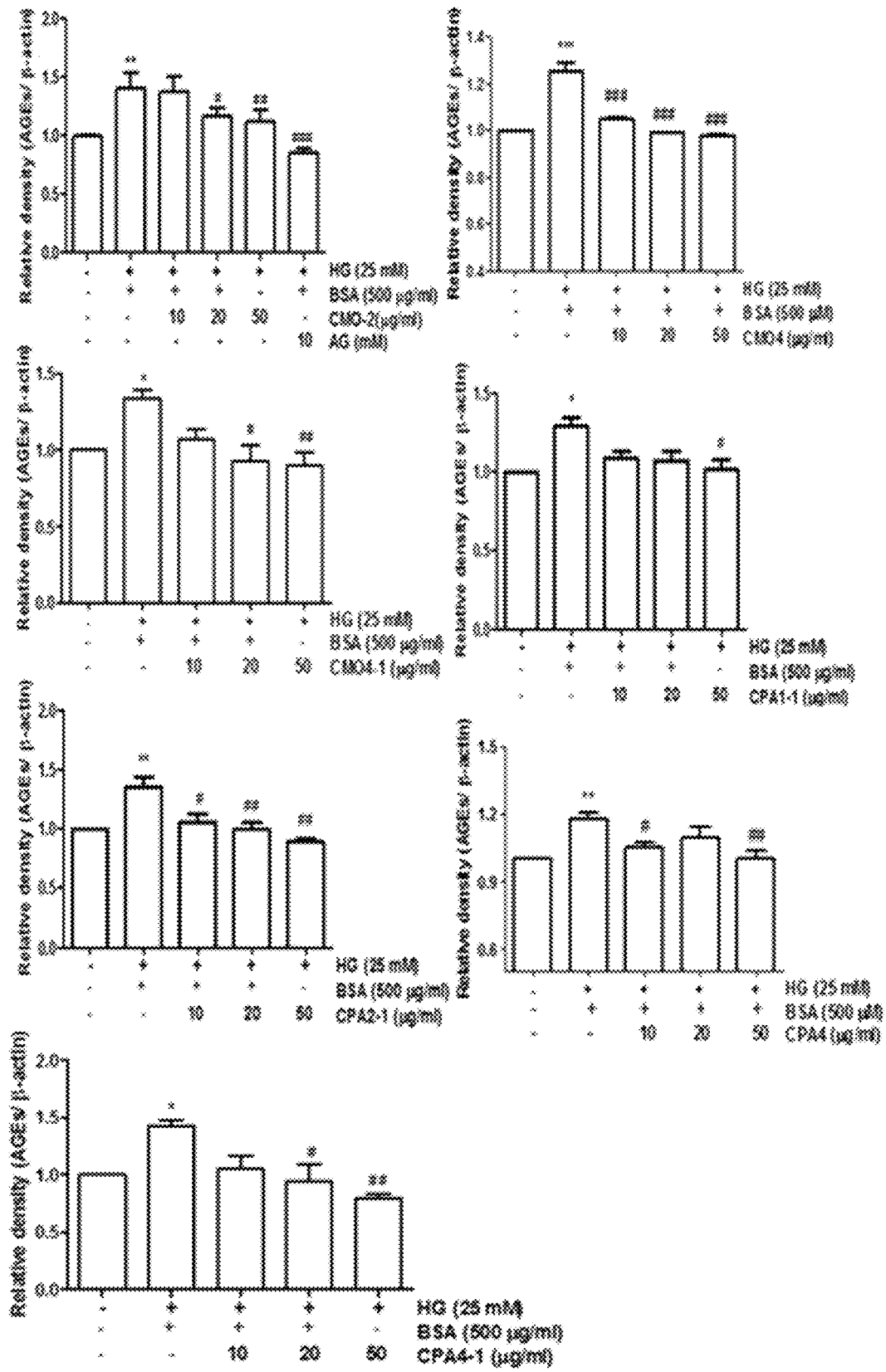

FIG. 3 is graphs confirming an effect of inhibiting production of advanced glycation end-products of CMO2 (extract of cinnamon twig and moutan root bark (1:2)), CMO4 (extract of cinnamon twig and moutan root bark (1:8)), CMO4-1 (hot water extract of cinnamon twig and moutan root bark (1:8)), CPA1-1 (hot water extract of cinnamon twig and peony root (2:1)), CPA2-1 (hot water extract of cinnamon twig and peony root (1:2)), CPA4 (extract of cinnamon twig and peony root (1:8)), and CPA4-1 (hot water extract of cinnamon twig and peony root (1:8)), in a human retinal pigment epithelial cell line under a hyperglycemic environment:
HG: hyperglycemia-treated group;
BSA: bovine serum albumin-treated group;
CMO2: extract of cinnamon twig and moutan root bark (1:2);
CMO4: extract of cinnamon twig and moutan root bark (1:8);
CMO4-1: hot water extract of cinnamon twig and moutan root bark (1:8);
CPA1-1: hot water extract of cinnamon twig and peony root (2:1);
CPA2-1: hot water extract of cinnamon twig and peony root (1:2);
CPA4: extract of cinnamon twig and peony root (1:8);
CPA4-1: hot water extract of cinnamon twig and peony root (1:8);
AG: aminoguanidine-treated group as a positive control group;
*$p<0.05$ vs. CON;
**$p<0.01$ vs. CON;
***$p<0.001$ vs. CON;
$p<0.05$ vs. HG;
$p<0.01$ vs. HG; and
$p<0.001$ vs. HG.

Figure 4:
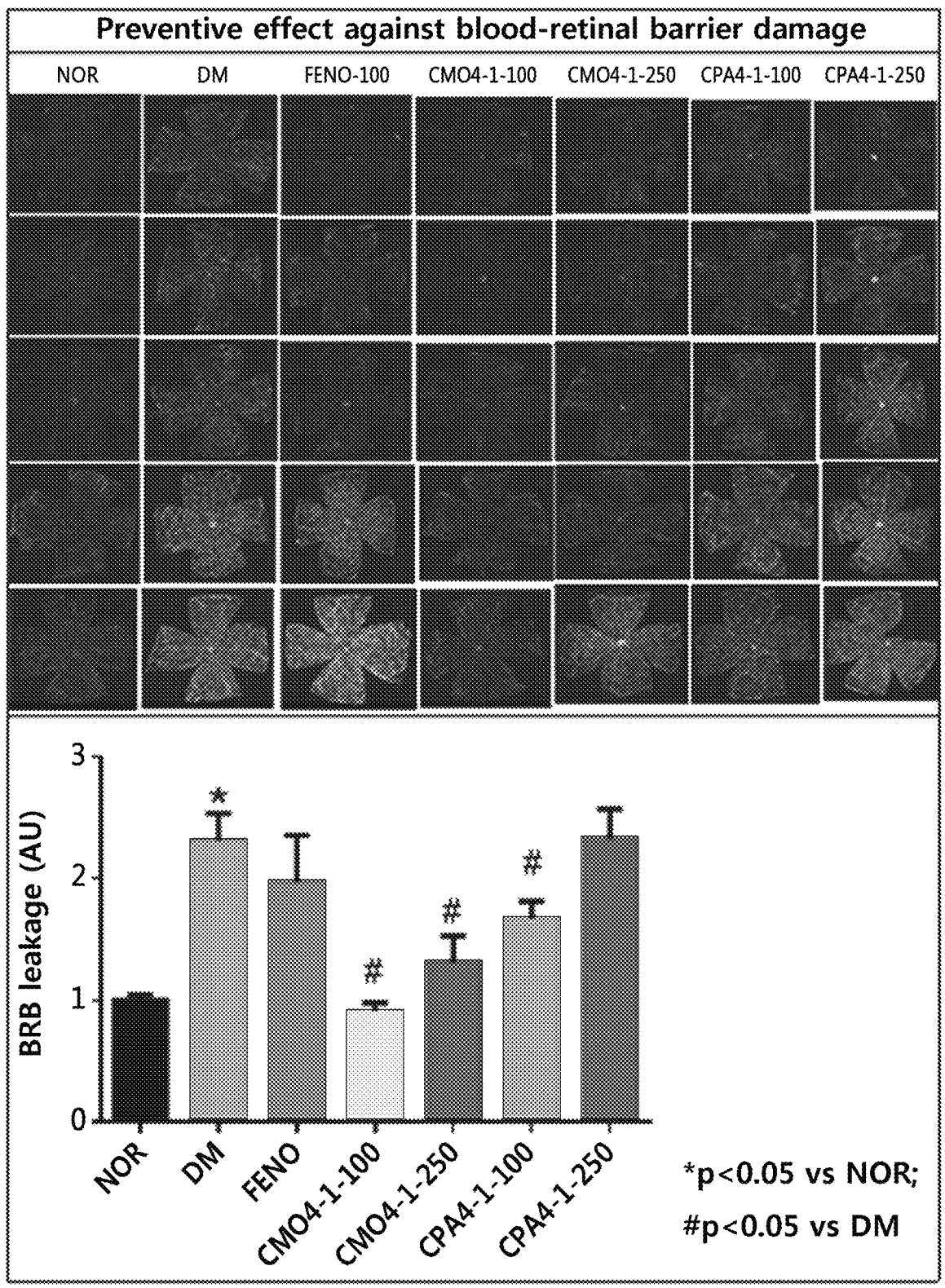

FIG. 4 is diagrams confirming a preventive effect against blood-retinal barrier damage, as a part of effects of preventing diabetic retinopathy, after administering CMO4-1 (hot water extract of cinnamon twig and moutan root bark (1:8)) and CPA4-1 (hot water extract of cinnamon twig and peony root (1:8)) in a type 2 diabetes model, db/db mice, for 12 weeks:
NOR: normal animal group (non-diabetic heterozygote db/+ mice);
DM: diabetic animal group (C57BL/KsJ-Lepr$^{db/db}$ diabetic mice);
FENO-100: a group administered with fenofibrate 100 mg/kg/day;
CMO4-1-100: a group administered with CMO4-1 100 mg/kg/day;
CMO4-1-250: a group administered with CMO4-1 250 mg/kg/day;
CPA4-1-100: a group administered with CPA4-1 100 mg/kg/day; and
CPA4-1-250: a group administered with CPA4-1 250 mg/kg/day.

Figure 5:
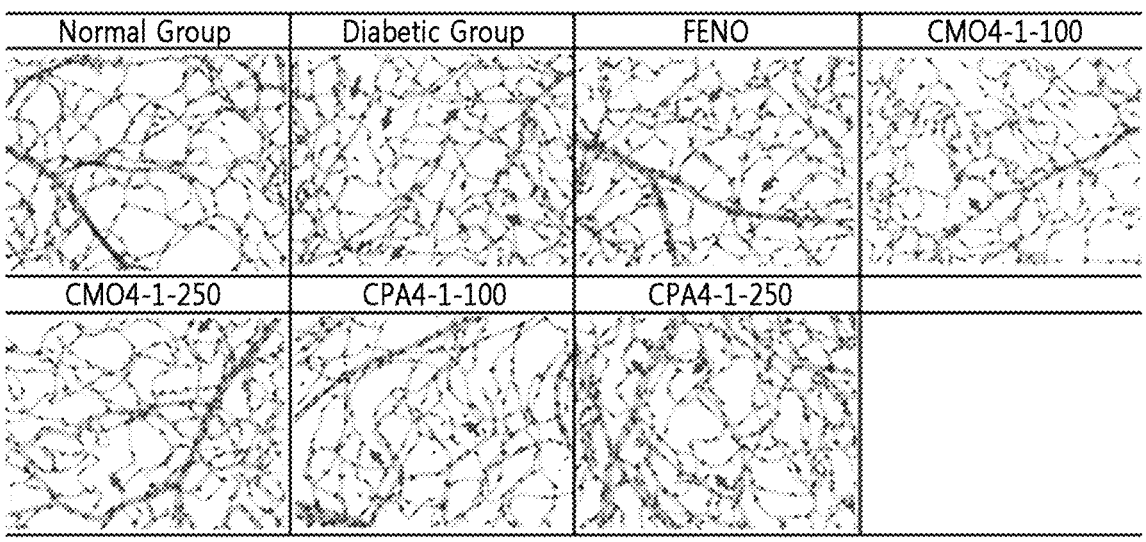
Figure 5:
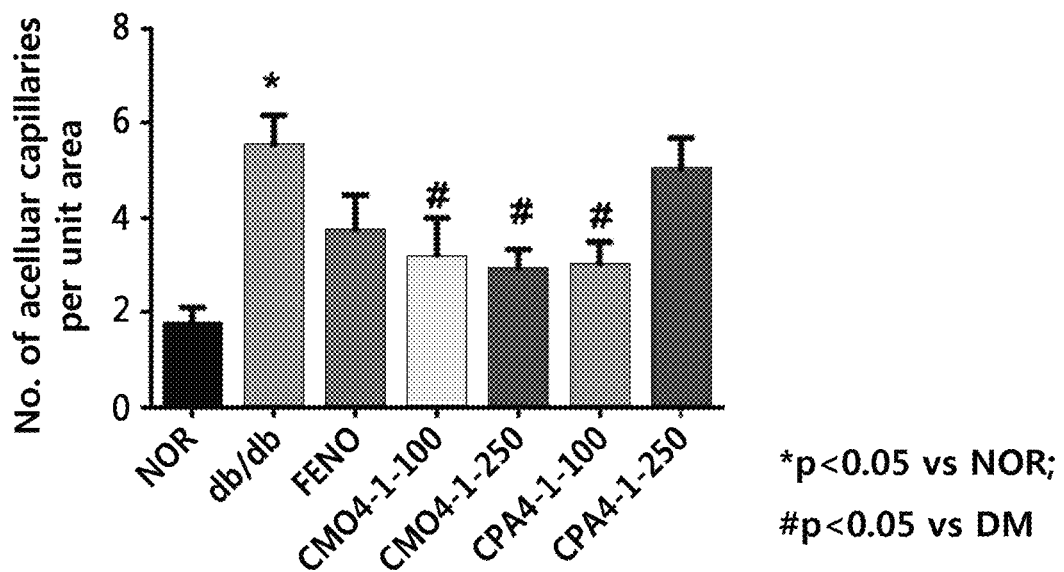

FIG. 5 is diagrams confirming a preventive effect against the formation of acellular capillaries, as a part of effects of preventing diabetic retinopathy, after administering CMO4-1 (hot water extract of cinnamon twig and moutan root bark (1:8)) and CPA4-1 (hot water extract of cinnamon twig and peony root (1:8)) in a type 2 diabetes model, db/db mice, for 12 weeks:
NOR: normal animal group (non-diabetic heterozygote db/+ mice);
DM: diabetic animal group (C57BL/KsJ-Lepr$^{db/db}$ diabetic mice);
FENO-100: a group administered with fenofibrate 100 mg/kg/day;
CMO4-1-100: a group administered with CMO4-1 100 mg/kg/day;
CMO4-1-250: a group administered with CMO4-1 250 mg/kg/day;
CPA4-1-100: a group administered with CPA4-1 100 mg/kg/day; and
CPA4-1-250: a group administered with CPA4-1 250 mg/kg/day.

FIG. 6 is diagrams confirming a preventive effect against the damage to occludin, a tight-junction protein, as a part of preventive effects against diabetic retinopathy, after administering CMO4-1 (hot water extract of cinnamon twig and moutan root bark (1:8)) and CPA4-1 (hot water extract of cinnamon twig and peony root (1:8)) in a type 2 diabetes model, db/db mice, for 12 weeks:
NOR: normal animal group (non-diabetic heterozygote db/+ mice);
DM: diabetic animal group (C57BL/KsJ-Lepr$^{db/db}$ diabetic mice);

FENO-100: a group administered with fenofibrate 100 mg/kg/day;

CMO4-1-100: a group administered with CMO4-1 100 mg/kg/day;

CMO4-1-250: a group administered with CMO4-1 250 mg/kg/day;

CPA4-1-100: a group administered with CPA4-1 100 mg/kg/day; and

CPA4-1-250: a group administered with CPA4-1 250 mg/kg/day.

Figure 7:
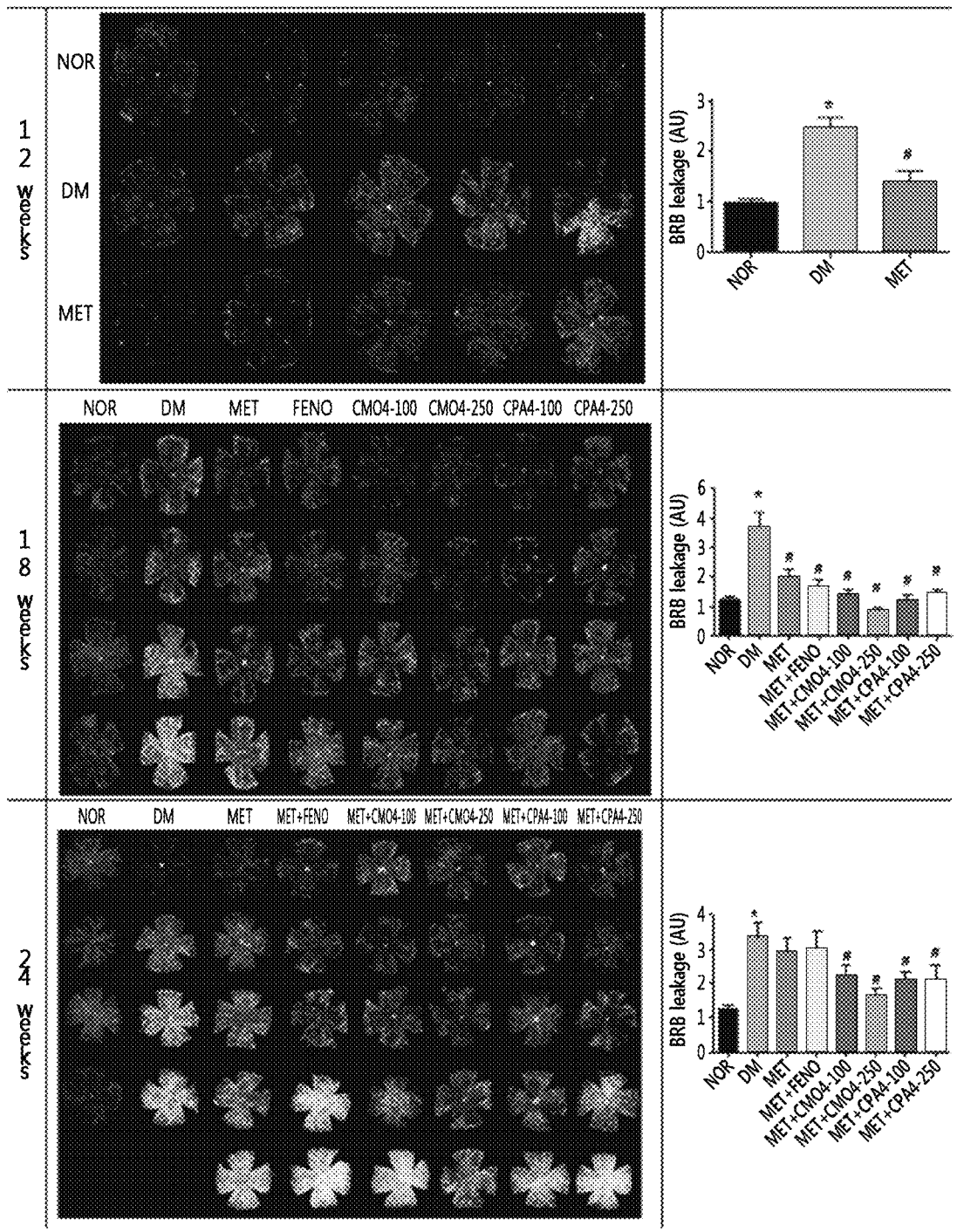

FIG. 7 is diagrams confirming an effect of treating blood-retinal barrier damage, as a part of effects of treating diabetic retinopathy, in which CMO4 (extract of cinnamon twig and moutan root bark (1:8)) and CPA4 (extract of cinnamon twig and peony root (1:8)) are co-administered with metformin for 12 weeks, after regulating blood glucose levels for 12 weeks while administering metformin in a type 2 diabetes model, db/db mice:

NOR: normal animal group (non-diabetic heterozygote db/+ mice);

DM: diabetic animal group (C57BL/KsJ-Lepr$^{db/db}$ diabetic mice);

MET: a group administered with metformin 350 mg/kg/day;

Met+Feno: a group administered with metformin 350 mg/kg/day and fenofibrate 100 mg/kg/day;

Met+CMO4-100: a group administered with metformin and CMO4 100 mg/kg/day;

Met+CMO4-250: a group administered with metformin and CMO4 250 mg/kg/day;

Met+CPA4-100: a group administered with metformin and CPA4 100 mg/kg/day;

Met+CPA4-250: a group administered with metformin and CPA4 250 mg/kg/day;

*$p<0.05$ vs. NOR; and

$p<0.05$ vs. DM.

Figure 8:
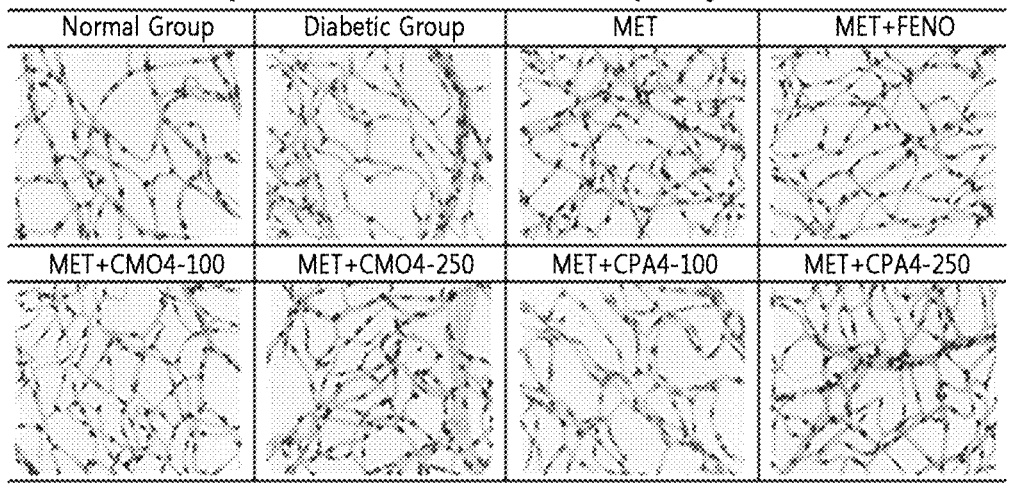
Figure 8:
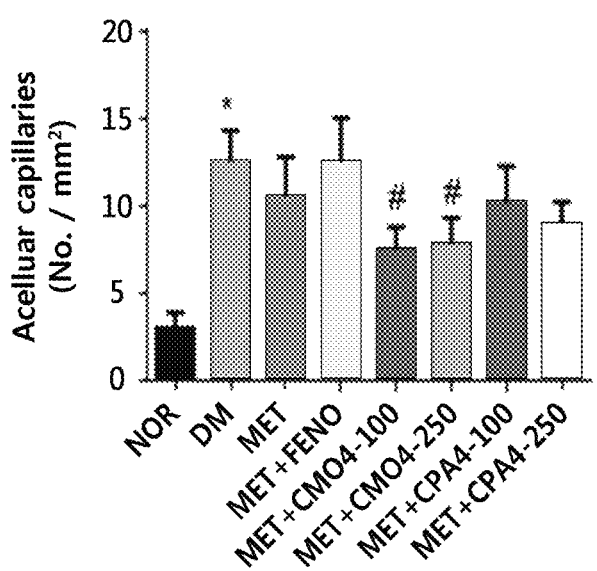

FIG. 8 is diagrams confirming an effect of inhibiting the formation of acellular capillaries, as a part of effects for treating diabetic retinopathy, in which CMO4 (extract of cinnamon twig and moutan root bark (1:8)) and CPA4 (extract of cinnamon twig and peony root (1:8)) are co-administered with metformin for 12 weeks, after regulating blood glucose levels for 12 weeks while administering metformin in a type 2 diabetes model, db/db mice:

NOR: normal animal group (non-diabetic heterozygote db/+ mice);

DM: diabetic animal group (C57BL/KsJ-Lepr$^{db/db}$ diabetic mice);

MET: a group administered with metformin 350 mg/kg/day;

Met+Feno: a group administered with metformin 350 mg/kg/day and fenofibrate 100 mg/kg/day;

Met+CMO4-100: a group administered with metformin and CMO4 100 mg/kg/day;

Met+CMO4-250: a group administered with metformin and CMO4 250 mg/kg/day;

Met+CPA4-100: a group administered with metformin and CPA4 100 mg/kg/day;

Met+CPA4-250: a group administered with metformin and CPA4 250 mg/kg/day;

*$p<0.05$ vs. NOR; and

$p<0.05$ vs. DM.

FIG. 9 is diagrams confirming an effect of treating the damage to tight-junction protein, as a part of effects of treating diabetic retinopathy, in which CMO4 (extract of cinnamon twig and moutan root bark (1:8)) and CPA4 (extract of cinnamon twig and peony root (1:8)) are co-administered with metformin for 12 weeks, after regulating blood glucose levels for 12 weeks while administering metformin in a type 2 diabetes model, db/db mice; FIG. 9a confirms the damage to claudin-5 by staining; and FIG. 9b is a diagram confirming the change of occludin using a western blot:

NOR: normal animal group (non-diabetic heterozygote db/+ mice);

DM: diabetic animal group (C57BL/KsJ-Lepr$^{db/db}$ diabetic mice);

MET: a group administered with metformin 350 mg/kg/day;

Met+Feno: a group administered with metformin 350 mg/kg/day and fenofibrate 100 mg/kg/day;

Met+CMO4-100: a group administered with metformin and CMO4 100 mg/kg/day;

Met+CMO4-250: a group administered with metformin and CMO4 250 mg/kg/day;

Met+CPA4-100: a group administered with metformin and CPA4 100 mg/kg/day;

Met+CPA4-250: a group administered with metformin and CPA4 250 mg/kg/day;

*$p<0.05$ vs. NOR; and

$p<0.05$ vs. DM.

Figure 10:
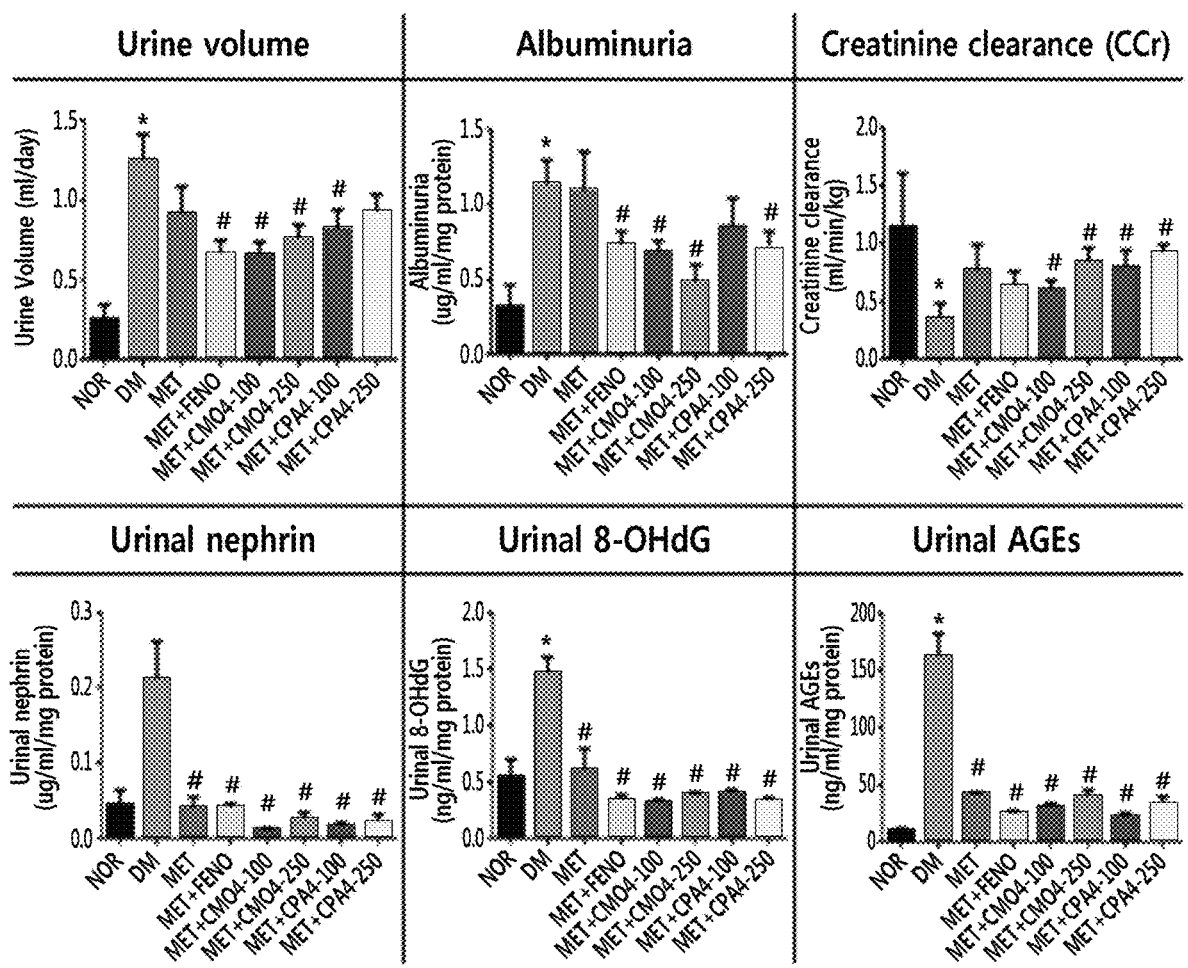
Figure 11:
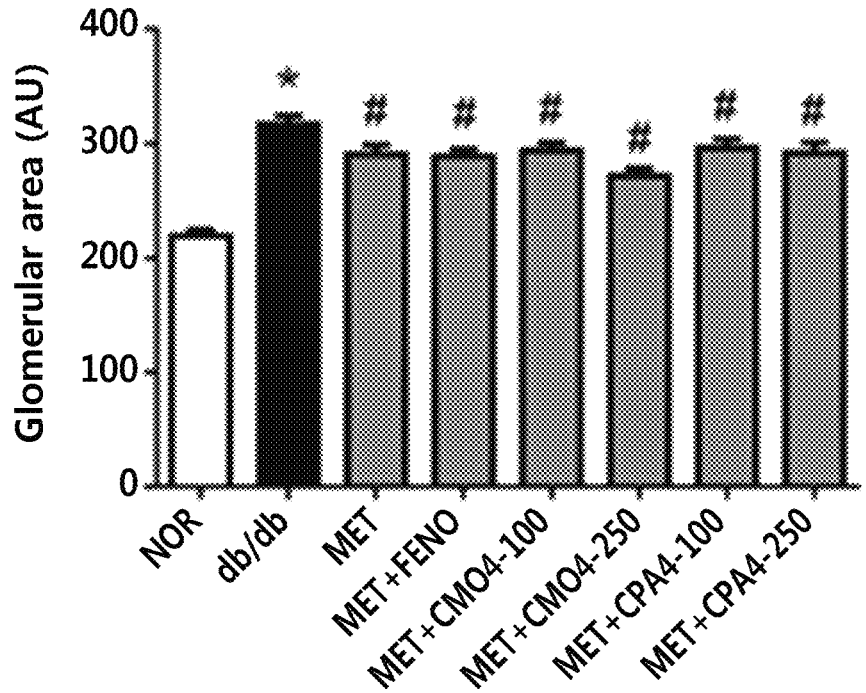
Figure 11:
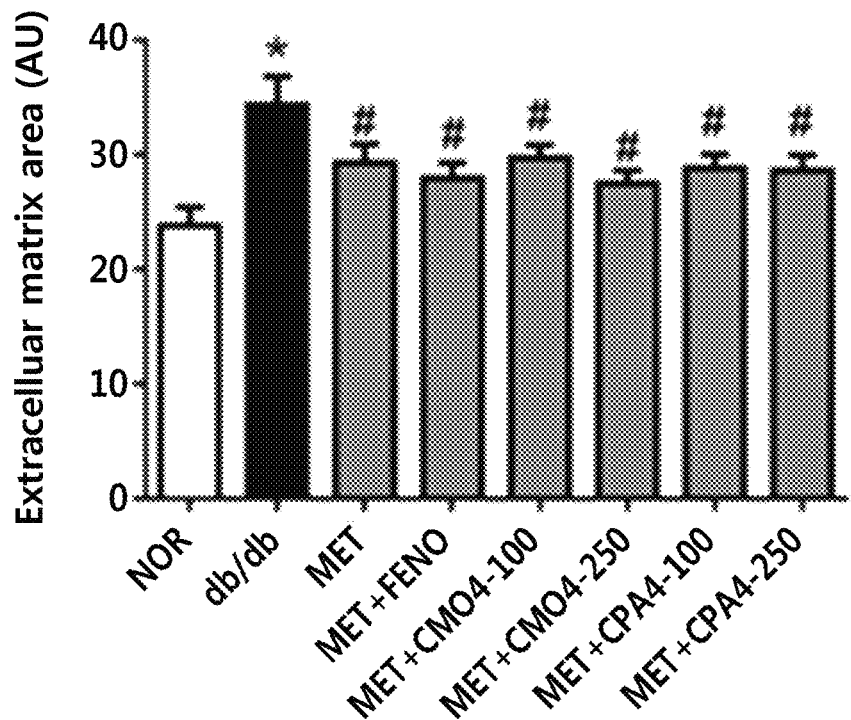

FIGS. 10 and 11 are diagrams analyzing an effect of ameliorating diabetic nephropathy, in which CMO4 (extract of cinnamon twig and moutan root bark (1:8)) and CPA4 (extract of cinnamon twig and peony root (1:8)) are co-administered with metformin for 12 weeks, after regulating blood glucose levels for 12 weeks while administering metformin in a type 2 diabetes model, db/db mice:

NOR: normal animal group (non-diabetic heterozygote db/+ mice);

DM: diabetic animal group (C57BL/KsJ-Lepr$^{db/db}$ diabetic mice);

MET: a group administered with metformin 350 mg/kg/day;

Met+Feno: a group administered with metformin 350 mg/kg/day and fenofibrate 100 mg/kg/day;

Met+CMO4-100: a group administered with metformin and CMO4 100 mg/kg/day;

Met+CMO4-250: a group administered with metformin and CMO4 250 mg/kg/day;

Met+CPA4-100: a group administered with metformin and CPA4 100 mg/kg/day;

Met+CPA4-250: a group administered with metformin and CPA4 250 mg/kg/day;

*$p<0.05$ vs. NOR; and

$p<0.05$ vs. DM (or db/db).

Figure 12:
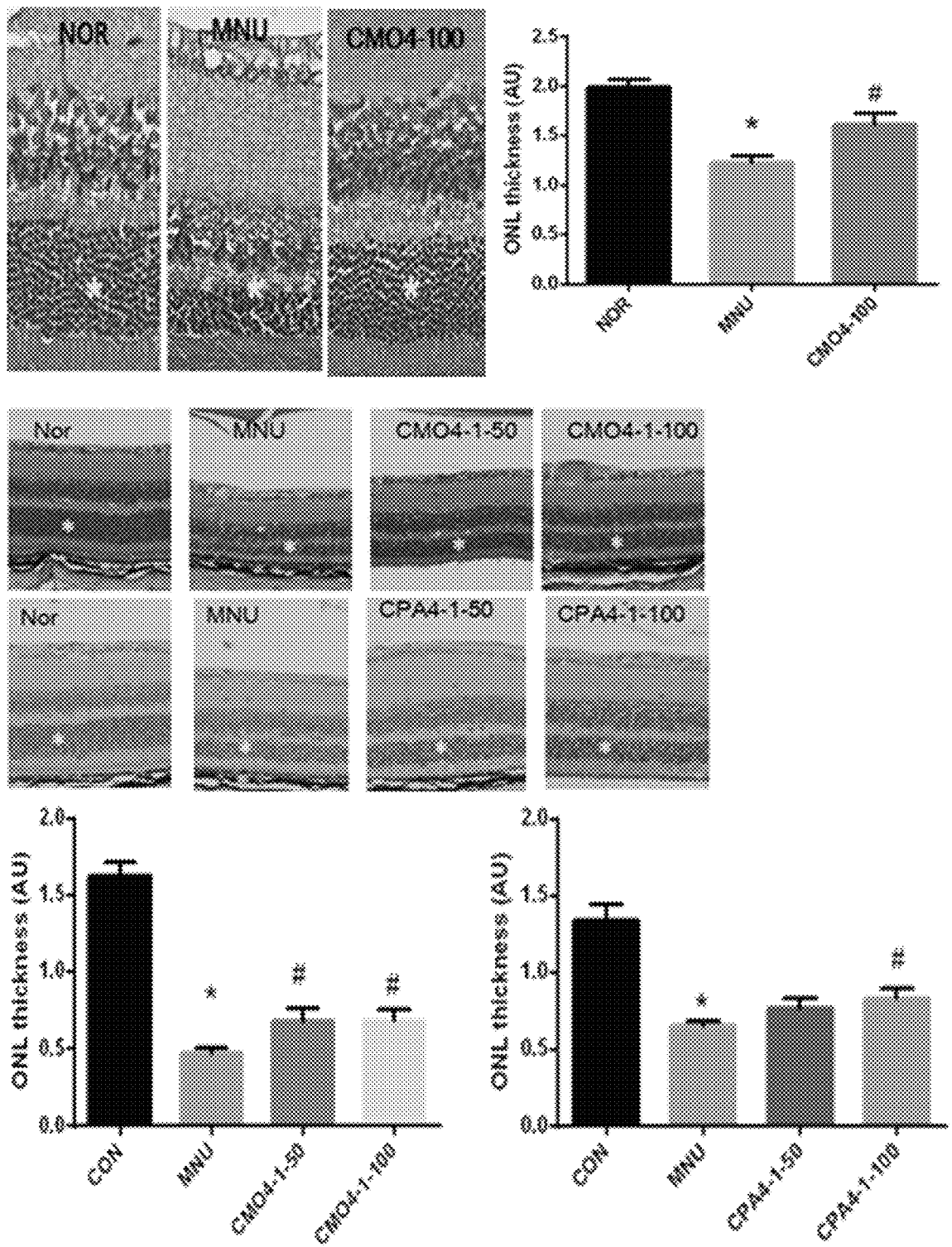

FIG. 12 is diagrams confirming a preventive effect of CMO4 (extract of cinnamon twig and moutan root bark (1:8)), CMO4-1 (hot water extract of cinnamon twig and moutan root bark (1:8)), and CPA4-1 (hot water extract of cinnamon twig and peony root (1:8)) against the damage to photoreceptor cells (macular degeneration) in an MNU-induced rodent model.

NOR: C57BL/6 normal mice;

MNU: N-methyl-N-nitrosourea (MNU) induced animal model;

CMO4-100: MNU-induced animal model administered with CMO4 100 mg/kg/day;

CMO4-1-50: MNU-induced animal model administered with CMO4-1 50 mg/kg/day;

CMO4-1-100: MNU-induced animal model administered with CMO4-1 100 mg/kg/day;

CPA4-1-50: MNU-induced animal model administered with CPA4-1 50 mg/kg/day;

CPA4-1-100: MNU-induced animal model administered with CPA4-1 100 mg/kg/day;
*p<0.05 vs. NOR; and
p<0.05 vs. MNU.

Figure 13:
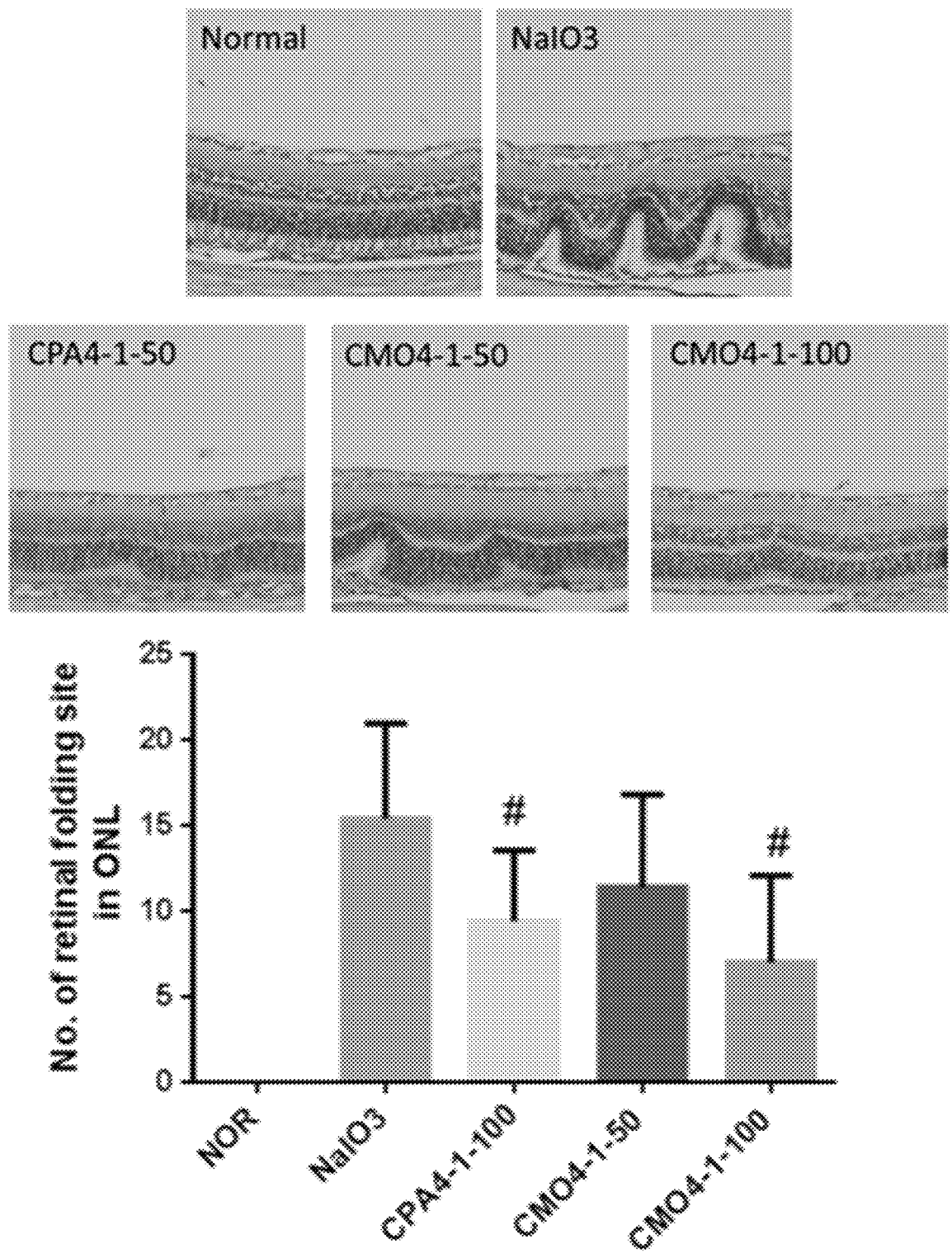

FIG. 13 is diagrams confirming a preventive effect of CMO4-1 (hot water extract of cinnamon twig and moutan root bark (1:8)) and CPA4-1 (hot water extract of cinnamon twig and peony root (1:8)) against the damage to retinal pigment epithelial cells (macular degeneration) in a NaIO$_3$-induced rodent model;
Normal: C57BL/6 normal mice;
NaIO$_3$: NaIO$_3$-induced animal model;
CMO4-1-50: NaIO$_3$-induced animal model administered with CMO4-1 50 mg/kg/day;
CMO4-1-100: NaIO$_3$-induced animal model administered with CMO4-1 100 mg/kg/day;
CPA4-1-50: NaIO$_3$-induced animal model administered with CPA4-1 50 mg/kg/day;
CPA4-1-100: NaIO$_3$-induced animal model administered with CPA4-1 100 mg/kg/day;
*p<0.05 vs. NOR; and
p<0.05 vs. NaIO$_3$.

Figure 14:
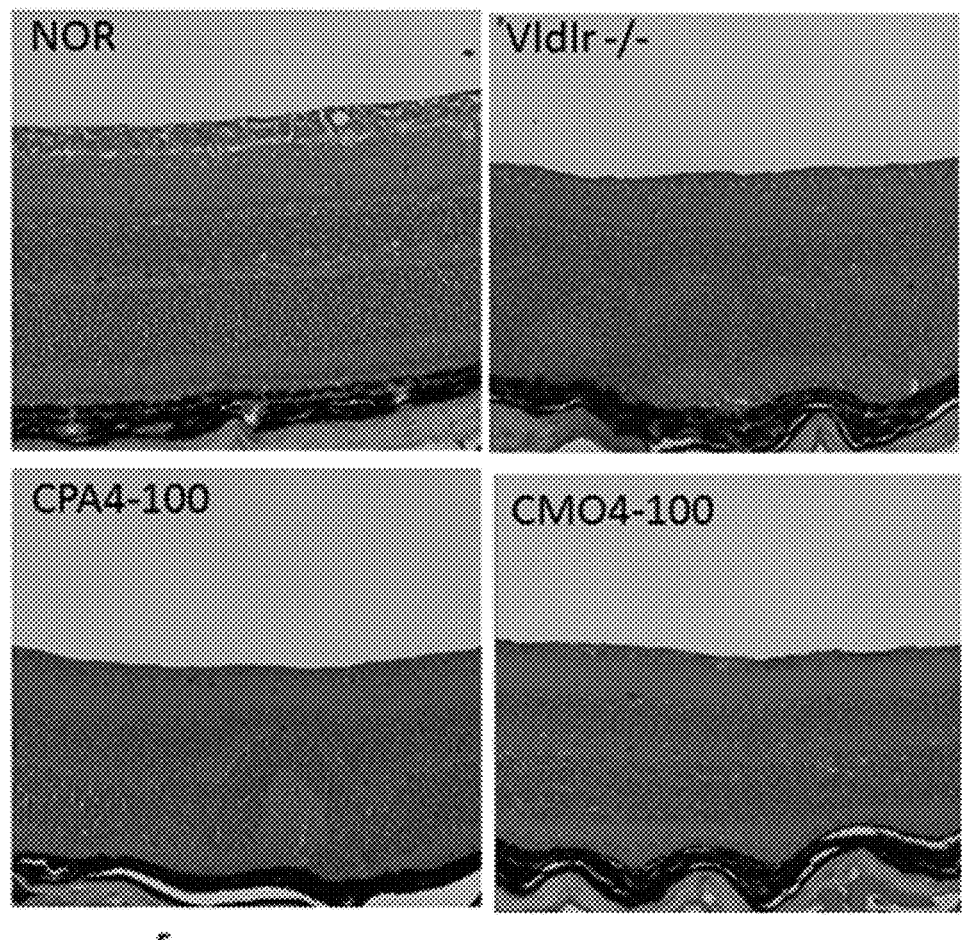
Figure 14:
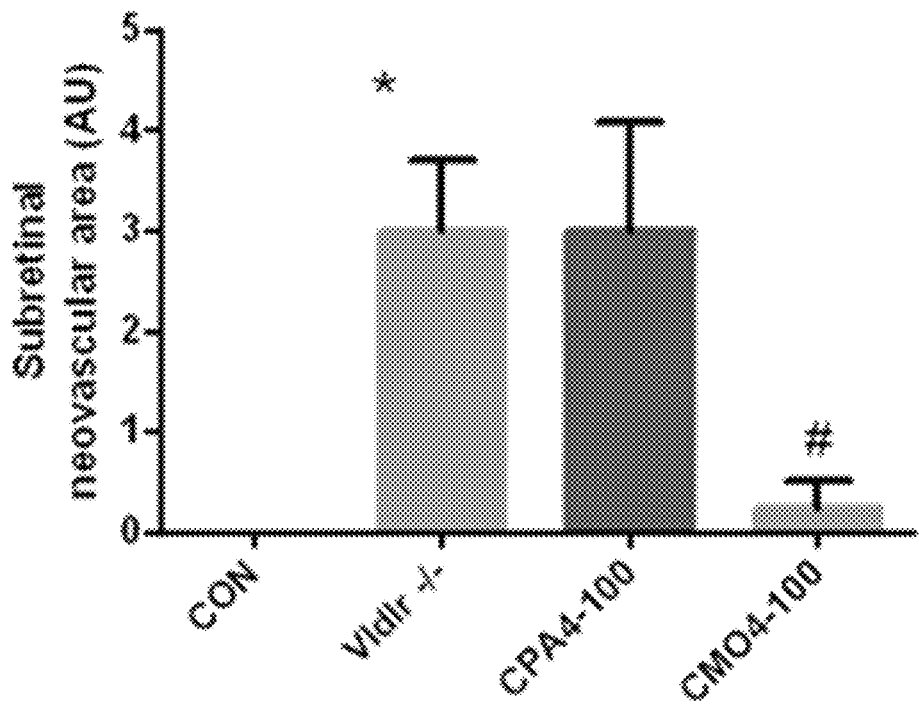

FIG. 14 is diagrams confirming an inhibitory effect of CMO4 (extract of cinnamon twig and moutan root bark (1:8)) and CPA4 (an extract of cinnamon twig and peony root (1:8)) against subretinal neovascularization in an animal model with Vldlr$^{-/-}$ macular degeneration:
NOR: C57BL/6 normal mice;
Vldlr$^{-/-}$: mouse model with wet macular degeneration;
CMO4-100: Vldlr$^{-/-}$ mice administered with CMO4 100 mg/kg/day;
CPA4-100: Vldlr$^{-/-}$ mice administered with CPA4 100 mg/kg/day;
*p<0.05 vs. CON; and
p<0.05 vs. Vldlr$^{-/-}$.

Figure 15:
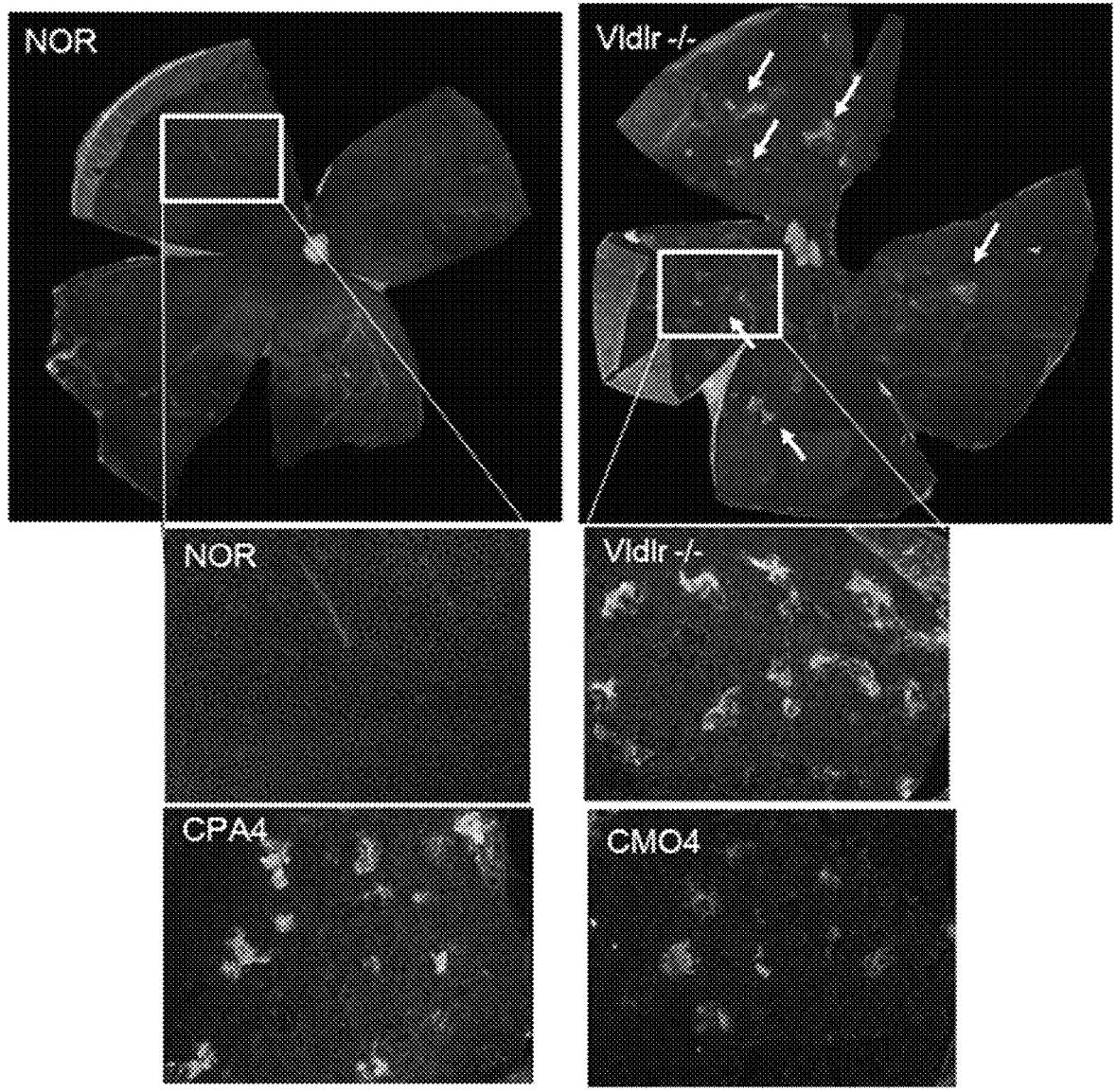

FIG. 15 is diagrams confirming an inhibitory effect of CMO4 (extract of cinnamon twig and moutan root bark (1:8)) and CPA4 (extract of cinnamon twig and peony root (1:8)) against the damage to retinal pigment epithelium cells in an animal model with Vldlr$^{-/-}$ macular degeneration:
NOR: C57BL/6 normal mice;
Vldlr$^{-/-}$: mouse model with wet macular degeneration;
CMO4-100: Vldlr$^{-/-}$ mice administered with CMO4 100 mg/kg/day; and
CPA4-100: Vldlr$^{-/-}$ mice administered with CPA4 100 mg/kg/day.

Figure 16:
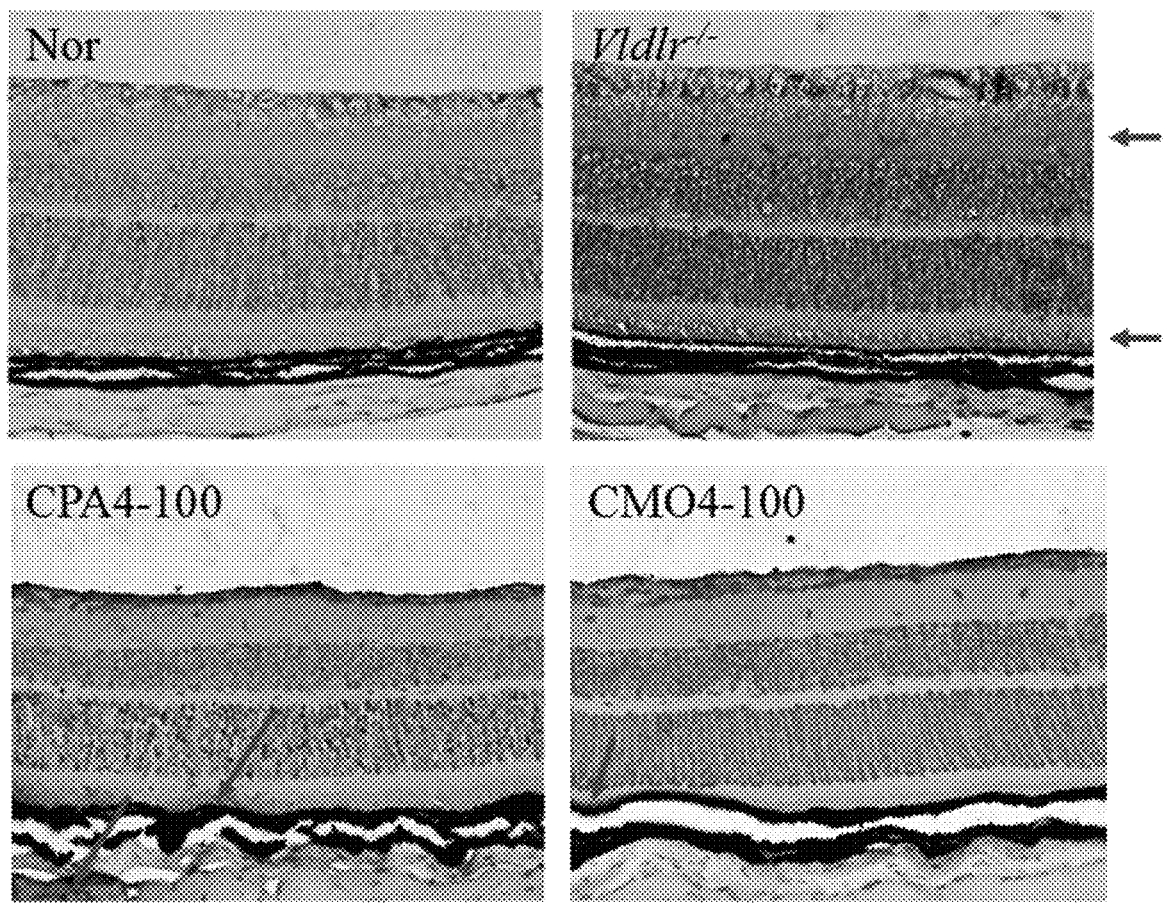

FIG. 16 is diagrams confirming an inhibitory effect of CMO4 (extract of cinnamon twig and moutan root bark (1:8)) and CPA4 (extract of cinnamon twig and peony root (1:8)) against VEGF expression (dark purple staining; indicated by arrows) in the retina of Vldlr$^{-/-}$ mice:
Nor: C57BL/6 normal mice;
Vldlr$^{-/-}$: mouse model with wet macular degeneration;
CMO4-100: Vldlr$^{-/-}$ mice administered with CMO4 100 mg/kg/day; and
CPA4-100: Vldlr$^{-/-}$ mice administered with CPA4 100 mg/kg/day.

Figure 17:
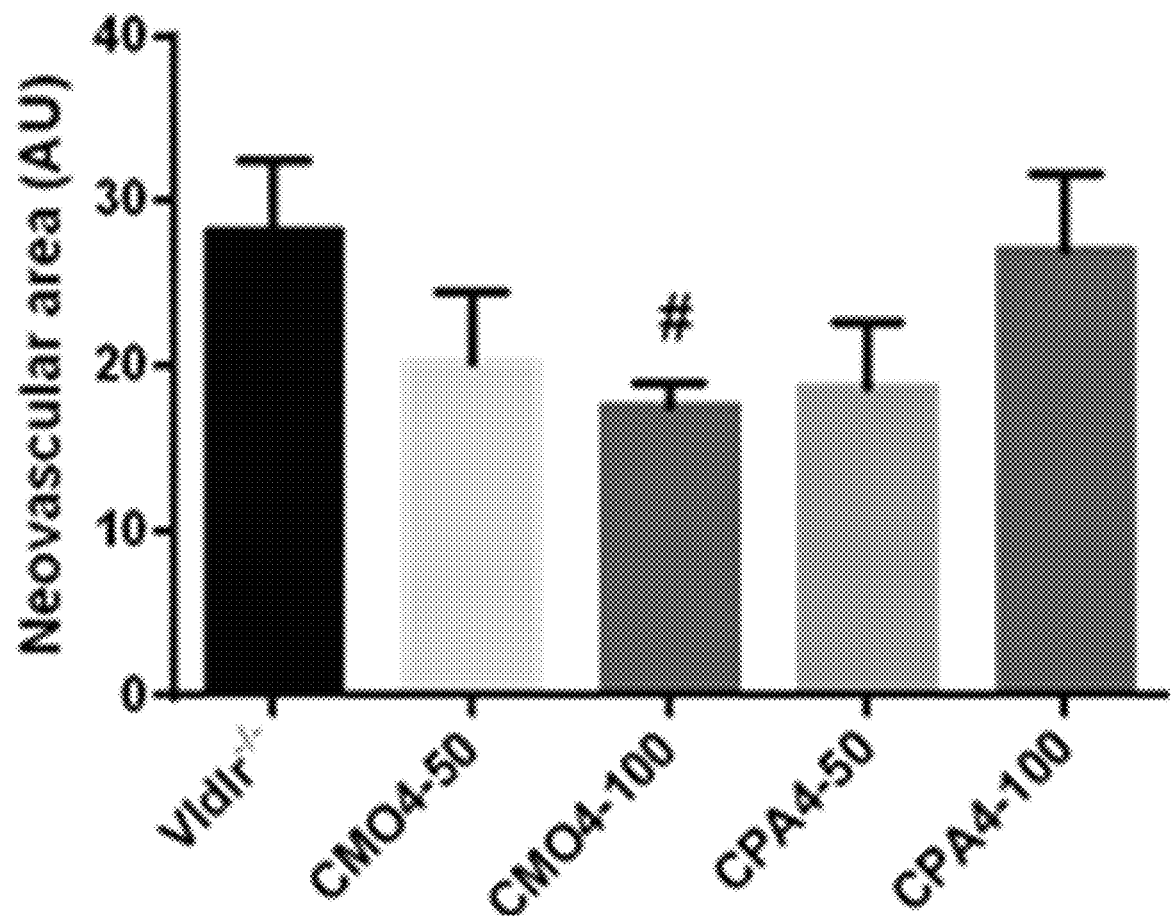

FIG. 17 is a graph confirming an inhibitory effect of CMO4 (extract of cinnamon twig and moutan root bark (1:8)) and CPA4 (extract of cinnamon twig and peony root (1:8)) against neovascularization in the retina of Vldlr$^{-/-}$ mice:
Vldlr$^{-/-}$: mouse model with wet macular degeneration;
CMO4-50: Vldlr$^{-/-}$ mice administered with CMO4 50 mg/kg/day;
CMO4-100: Vldlr$^{-/-}$ mice administered with CMO4 100 mg/kg/day;
CPA4-50: Vldlr$^{-/-}$ mice administered with CPA4 50 mg/kg/day; and
CPA4-100: Vldlr$^{-/-}$ mice administered with CPA4 100 mg/kg/day.

Figure 18:
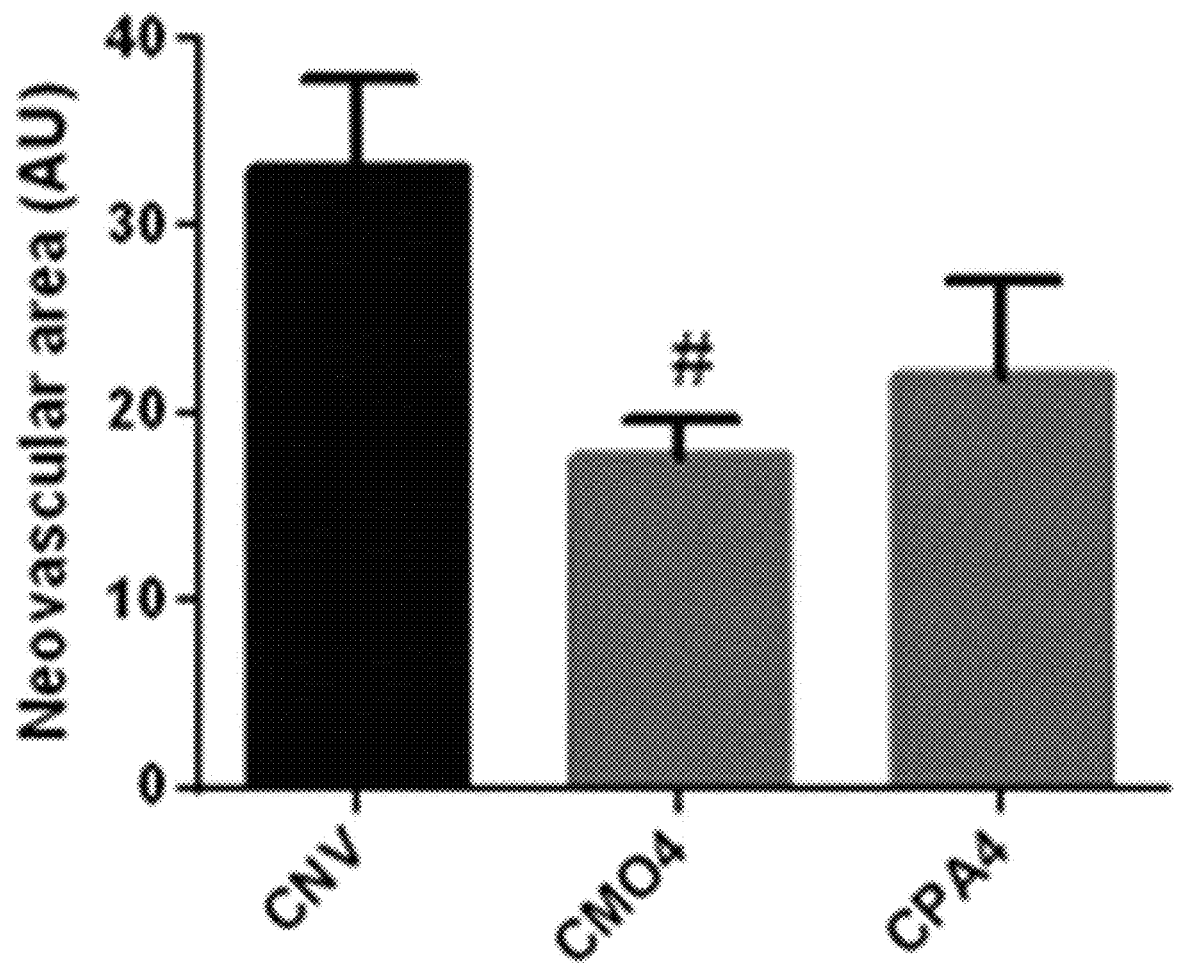

FIG. 18 is a graph confirming an inhibitory effect of CMO4 (extract of cinnamon twig and moutan root bark (1:8)) and CPA4 (extract of cinnamon twig and peony root (1:8)) against neovascularization in a subretinal area of rats with choroidal neovascularization induced by lasers:
CNV: laser-treated mouse model with wet macular degeneration;
CMO4: laser-treated mice with wet macular degeneration, in which the mice are administered with CMO4 100 mg/kg/day;
CPA4: laser-treated mice with wet macular degeneration, in which the mice are administered with CPA4 100 mg/kg/day; and
p<0.05 vs. CNV.

Figure 19:
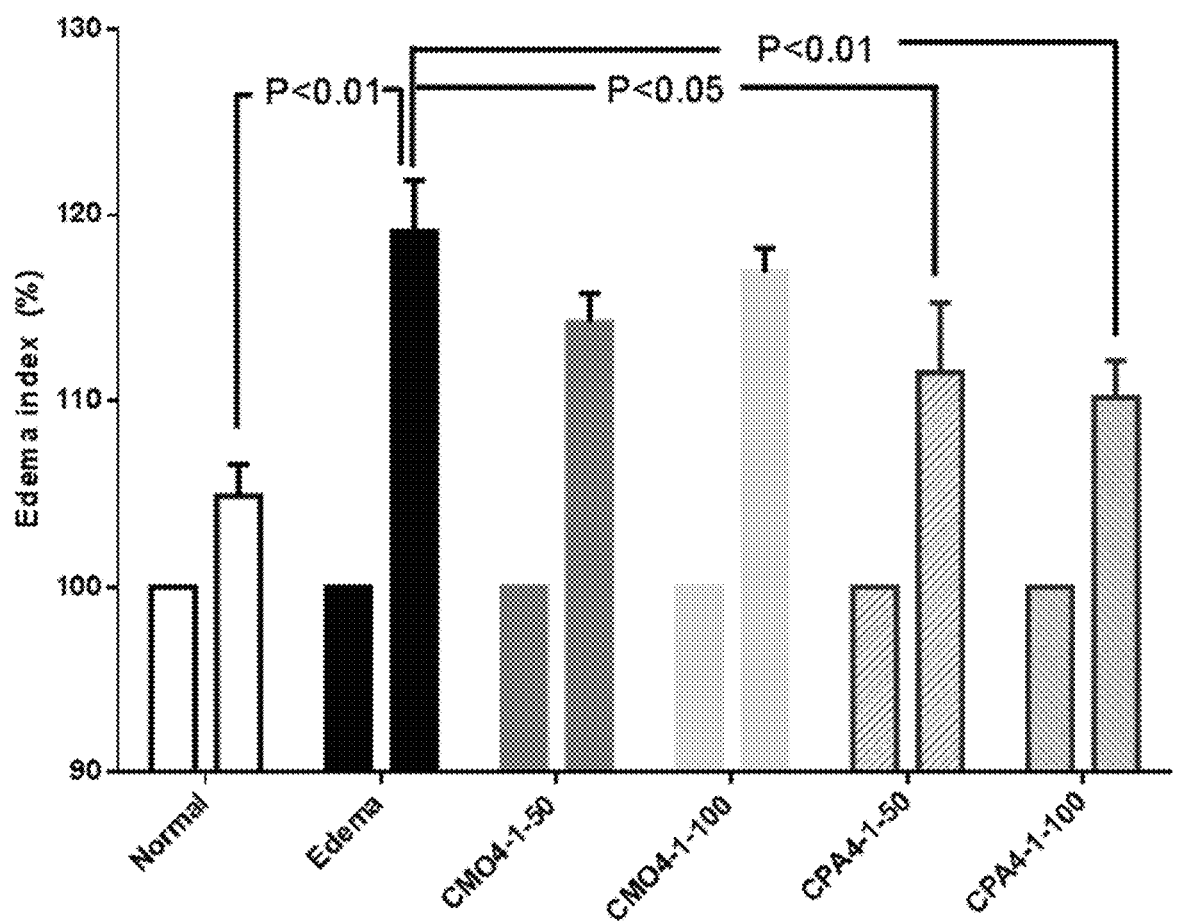

FIG. 19 is a graph confirming an effect of preventing and treating varicose veins in an animal model in which varicose veins are induced by formalin.
Normal: normal animal group (SD rat);
Edema: varicose veins-induced animal group;
CMO4-1-50: varicose veins-induced group administered with CMO4-1 50 mg/kg/day;
CMO4-1-100: varicose veins-induced group administered with CMO4-1 100 mg/kg/day;
CPA4-1-50: varicose veins-induced group administered with CPA4-1 50 mg/kg/day; and
CPA4-1-100: varicose veins-induced group administered with CPA4-1 100 mg/kg/day.

BEST MODE

Hereinbelow, the present invention will be described in more detail.

The present invention provides a pharmaceutical composition for preventing and treating diabetic complications and angioedema, containing a cinnamon twig extract as an active ingredient.

The extract is extracted by additionally mixing any one selected from the group consisting of moutan root bark, peony root, and poria.

The extract inhibits the excessive production of advanced glycation end-products, exhibits an effect of fragmentizing a cross-link between advanced glycation end-products and matrix proteins, and inhibits the production of advanced glycation end-products in a human retinal pigment epithelial cell line.

Additionally, the diabetic complications are preferably any one selected from the group consisting of diabetic retinopathy, diabetic cataract, diabetic nephropathy, diabetic neuropathy, diabetic foot ulcers, diabetic heart disease, diabetic osteoporosis, or diabetic arteriosclerosis, but are not limited thereto.

Additionally, the angioedema is preferably any one selected from the group consisting of macular degeneration, macular edema, retinal degeneration, and varicose veins, but is not limited thereto.

The mixed extract of cinnamon twig and moutan root bark, cinnamon twig and peony root, or cinnamon twig and poria is preferably prepared according to the following steps, but is not limited thereto:

1) a step of extracting cinnamon twig and moutan root bark, cinnamon twig and peony root, or cinnamon twig and poria by adding an extraction solvent to each thereof;

2) a step of filtering the extract of step 1); and 3) a step of concentrating the filtered extract of step 2) under reduced pressure;

wherein, in the above method, cinnamon twig, moutan root bark, peony root and poria used in step 1) can be used without restriction; and can be cultivated or purchased.

It is preferable that the mixed extract is mixed with cinnamon twig and moutan root bark at a weight ratio of 2:1 to 1:10, and then extracted with an extraction solvent. More preferably, they are mixed at a weight ratio of 1:1 to 1:8, and then extracted with an extraction solvent.

It is preferable that the mixed extract is mixed with cinnamon twig and peony root at a weight ratio of 2:1 to 1:10, and then extracted with an extraction solvent. More preferably, they are mixed at a weight ratio of 2:1 to 1:8, and then extracted with an extraction solvent.

It is preferable that the mixed extract is mixed with cinnamon twig and poria at a weight ratio of 2:1 to 1:2, and then extracted with an extraction solvent. More preferably, they are mixed at a weight ratio of 1:1, and then extracted with an extraction solvent.

It is preferable to use water, an alcohol, or a mixture thereof as the extraction solvent. As the alcohol, it is preferable to use $C_1$ to $C_2$ lower alcohols. In addition, it is preferable to use 30% ethanol, 50% ethanol, 70% ethanol, or methanol as lower alcohols. For an extraction method, it is preferable to use a high-temperature decompression method, a hot-water extraction method, a reflux extraction method, a hydrothermal extraction method, a maceration extraction method, a room-temperature extraction method, an ultra-sonification extraction method, or a steam extraction method, but the extraction method is not limited thereto. The amount of the extraction solvent is preferably extracted by adding 1 to 10 times the amount of cinnamon twig and moutan root bark, cinnamon twig and peony root, or cinnamon twig and poria. The extraction temperature is preferably from 30° C. to 100° C., but is not limited thereto. Further, the extraction time is preferably 2 hours to 48 hours, but is not limited thereto. Furthermore, the extraction frequency is preferably 2 to 5 times, but is not limited thereto.

In the above method, the reduced pressure concentration of step 3) is preferably accomplished using a vacuum reduced pressure concentrator or a rotary vacuum evaporator, but is not limited thereto. In addition, the concentrate is preferably dried using a reduced-pressure drying method, a vacuum drying method, a boiling drying method, a spray drying method, or a freeze drying method, but is not limited thereto.

The mixed extract may be prepared by mixing cinnamon twig and moutan root bark, cinnamon twig and peony root, or cinnamon twig and poria. In addition, each of cinnamon twig, moutan root bark, peony root, or poria may be extracted, and then mixed to prepare the mixed extract.

In a specific embodiment of the present invention, the present inventors mixed cinnamon twig and moutan root bark, cinnamon twig and peony root, or cinnamon twig and poria at various ratios to prepare the mixed extract, and ingredients thereof were analyzed (see FIGS. 1a to 1d). Additionally, the content of paeoniflorin was confirmed in each extract (see Table 1), and by using the same, an effect for inhibiting the production of advanced glycation end-products in vitro was confirmed. As a result, the mixed extract of the present invention exhibited a remarkable inhibitory effect against the production of advanced glyca- tion end-products compared to a positive control group. In particular, considering that aminoguanidine, a positive control group, is a single synthetic compound, it was confirmed that the mixed extract of the present invention exhibits a remarkably excellent inhibitory effect against the production of advanced glycation end-products (see Table 2).

Additionally, after treating the mixed extract of the present invention with glycoaldehyde, the effect of inhibiting the production of advanced glycation end-products was confirmed. As a result, it was confirmed that the extracts of cinnamon twig and moutan root bark (CMO4 and CMO4-1) and the extracts of cinnamon twig and peony root (CPA4 and CPA4-1) according to the present invention significantly inhibited the production of advanced glycation end-products in a concentration-dependent manner (1 μg/mL, 5 μg/mL, 10 μg/mL, 20 μg/mL, and 50 μg/mL) (see FIG. 2). In addition, as a result of confirming the effect of fragmentizing a cross-link between advanced glycation end-products and matrix proteins, the mixed extract of the present invention exhibited a superior effect of fragmentizing the cross-link compared to that of ALT-711, which is a positive control group. In particular, considering that ALT-711, a positive control group, is a single synthetic compound, it was confirmed that the mixed extract of the present invention exhibited a remarkably excellent effect of fragmentizing the cross-link (see Table 3).

Additionally, the inhibitory effect of the mixed extract of the present invention against the production of advanced glycation end-products in a human retinal pigment epithelial cell line under a hyperglycemic environment was confirmed. As a result, it was confirmed that the extracts of cinnamon twig and moutan root bark (CMO2, CMO4 and CMO4-1) and the extracts of cinnamon twig and peony root (CPA1-1, CPA2-1, CPA4 and CPA4-1) according to the present invention inhibited the production of advanced glycation end-products in a human retinal pigment epithelial cell line under a hyperglycemic environment, in a concentration-dependent manner (10 μg/mL, 20 μg/mL, and 50 μg/mL) (see FIG. 3).

Based on the results above, it was confirmed that the extract of cinnamon twig and moutan root bark, extract of cinnamon twig and peony root, and extract of cinnamon twig and poria inhibited the production of advanced glycation end-products, inhibited the advanced glycation end-products in ECM coated with glycoaldehyde, fragmentized a cross-link between the already-produced advanced glycation end-products and matrix proteins, and significantly suppressed the production of the advanced glycation end-products in a human retinal pigment epithelial cell line under a hyperglycemic environment.

Additionally, as a result of confirming an inhibitory effect of the mixed extract of the present invention against the damage to the blood-retinal barrier, it was confirmed that CMO4-1-100 and CMO4-1-250, groups administered with the hot water extracts of cinnamon twig and moutan root bark (1:8), and CPA4-1-100, a group administered with the hot water extract of cinnamon twig and peony root (1:8), according to the present invention significantly prevented the outflow of a fluorescent material from retina vessels (see FIG. 4). In addition, as a result of confirming an inhibitory effect against the formation of acellular capillaries, it was confirmed that CMO4-1-100 and CMO4-1-250, groups administered with the hot water extract of cinnamon twig and moutan root bark (1:8), and CPA4-1-100, a group administered with the hot water extract of cinnamon twig and peony root (1:8), according to the present invention significantly prevented the formation of acellular capillaries (see FIG. 5). In addition, as a result of confirming an inhibitory effect against the damage to occludin, a tight-junction protein between cells, it was confirmed that there was no occludin loss in CMO4-1-100 and CMO4-1-250, groups administered with the hot water extract of cinnamon twig and moutan root bark (1:8) (see FIG. 6).

Additionally, as a result of confirming an inhibitory effect of the mixed extract of the present invention against damage to the blood-retinal barrier, it was confirmed that when CMO4-100 and CMO4-250 (groups administered with the extract of cinnamon twig and moutan root bark (1:8)) and CPA4-100 and CPA4-250 (groups administered with the extract of cinnamon twig and peony root (1:8)) were respectively co-administered with metformin, they showed a therapeutic effect by significantly preventing the outflow of fluorescent material from retinal blood vessels at 18 weeks and 24 weeks (see FIG. 7). As a result of confirming an inhibitory effect against the formation of acellular capillaries, it was confirmed that when CMO4-100 and CMO4-250 (groups administered with the extract of cinnamon twig and moutan root bark (1:8)) were respectively co-administered with metformin, both significantly inhibited the formation of acellular capillaries (see FIG. 8). As a result of confirming an inhibitory effect against the damage to claudin-5, a tight-junction protein between cells, it was confirmed that when CMO4-100 and CMO4-250 (groups administered with the extract of cinnamon twig and moutan root bark (1:8)), and CPA4-100 and CPA4-250 (groups administered with the extract of cinnamon twig and peony root (1:8)) were respectively co-administered with metformin, there was no claudin-5 loss therein (see FIG. 9a). Additionally, it was confirmed that when both CMO4-250 (group administered with the extract of cinnamon twig and moutan root bark (1:8)) and CPA4-250 (group administered with the extract of cinnamon twig and peony root (1:8)) were respectively co-administered with metformin, both groups showed a significant increase in the amount of claudin-5 (see FIG. 9b).

Additionally, as a result of confirming an effect of the mixed extract of the present invention for preventing and treating decrease in renal function, it was confirmed that when CMO4-100 and CMO4-250 (groups administered with the extract of cinnamon twig and moutan root bark (1:8)) and CPA4-100 and CPA4-250 (groups administered with the extract of cinnamon twig and peony root (1:8)) were co-administered with metformin, these significantly inhibited albumin and creatinine clearance (see FIG. 10). As a result of confirming glomerulosclerosis, a morphological change caused by diabetic nephropathy, it was confirmed that when CMO4-100 and CMO4-250 (groups administered with the extract of cinnamon twig and moutan root bark (1:8)), and CPA4-100 and CPA4-250 (groups administered with the extract of cinnamon twig and peony root (1:8)) were co-administered with metformin, these groups significantly inhibited glomerulosclerosis (see FIG. 11).

Additionally, in order to confirm preventive and therapeutic effects of the mixed extract of the present invention against macular degeneration, the damage and denaturation of photoreceptor cells were confirmed using thickness of an outer nuclear layer in retinal tissues. As a result, photoreceptor cell damage caused by MNU was significantly inhibited in groups administered with CMO4, CMO4-1 (extracts of cinnamon twig and moutan root bark (1:8)), and CPA4-1 (extract of cinnamon twig and peony root (1:8)) (see FIG. 12). The damage and denaturation of retinal pigment epithelial cells were confirmed by folding numbers of an outer nuclear layer in retinal tissues. As a result, the damage to epithelial cells induced and pigmented by $NaOI_3$ was inhibited in groups administered with CMO4-1 (hot water extract of cinnamon twig and moutan root bark (1:8)) and CPA4-1 (hot water extract of cinnamon twig and peony root (1:8)), thereby significantly inhibiting phenomenon in which the outer nuclear layer bends (see FIG. 13).

Additionally, an inhibitory effect of the mixed extract of the present invention against subretinal neovascularization was confirmed by measuring a size of edema in retinal blood vessels. As a result, the subretinal neovascularization was significantly inhibited by administering CMO4 (extract of cinnamon twig and moutan root bark (1:8)) (see FIG. 14). Denaturation of the morphological structure of retinal pigment epithelial cells was confirmed. As a result, the denaturation thereof was significantly inhibited by administering CMO4 (extract of cinnamon twig and moutan root bark (1:8)) (see FIG. 15). In addition, an inhibitory effect of VEGF expression in the retina was confirmed. As a result, the VEGF expression was significantly inhibited by administering CMO4 (extract of cinnamon twig and moutan root bark (1:8)) and CPA4 (extract of cinnamon twig and peony root (1:8)) (see FIG. 16).

Additionally, an inhibitory effect of the mixed extract of the present invention against subretinal neovascularization was confirmed. As a result, the neovascularization was significantly inhibited by administering 100 mg/kg of CMO4 (extract of cinnamon twig and moutan root bark (1:8)) (see FIG. 17). As a result of confirming an inhibitory effect against subretinal neovascularization in a subretinal area, the neovascularization was significantly inhibited by administering 100 mg/kg of CMO4 (extract of cinnamon twig and moutan root bark (1:8)). In addition, the neovascularization tended to be inhibited by administering 100 mg/kg of CPA4 (extract of cinnamon twig and peony root (1:8)) (see FIG. 18). As a result of confirming the change in a thickness of an outer nuclear layer, which was caused by damage to photoreceptor cells in retinal nerve tissues, 2.7% of CMO4 (extract of cinnamon twig and moutan root bark (1:8)), which has the lowest content of paeoniflorin, showed a remarkably excellent effect. This result showed that the effect of the extract of cinnamon twig and moutan root bark, or the extract of cinnamon twig and peony root is not merely caused by paeoniflorin, but the effect thereof is, in fact, a synergistic effect of the numerous ingredients present in the extract of cinnamon twig and moutan root bark, or in the extract of cinnamon twig and peony root (see Tables 4 and 5).

Additionally, as a result of confirming the condition of edema before and after inducing lower extremity edema using the mixed extract of the present invention, the change in size of edema caused by lower extremity edema was not greatly inhibited by CMO4-1 (extract of cinnamon twig and moutan root bark (1:8)), but it was significantly inhibited by CPA4-1 (extract of cinnamon twig and peony root (1:8)) in a concentration-dependent manner (see FIG. 19).

Therefore, the mixed extract of cinnamon twig and moutan root bark, cinnamon twig and peony root, or cinnamon twig and poria according to the present invention has been confirmed to inhibit the excessive production of advanced glycation end-products, which occurs under chronic diabetic conditions, exhibit the effect of fragmentizing a cross-link between the advanced glycation end-products and matrix proteins, have an excellent effect in inhibiting the production of the advanced glycation end-products in a human retinal pigment epithelial cell line subjected to a hyperglycemic or aging environment, and have excellent effects in delaying, preventing, and treating diabetic complications, muscular degeneration, commotio retinae, and lower extremity edema in various animal models of diabetic complications, macular degeneration, and lower extremity edema, and thus the mixed extract of cinnamon twig and moutan root bark, cinnamon twig and peony root, or cinnamon twig and poria can efficiently be used as a pharmaceutical composition for preventing and treating diabetic complications and angioedema.

A composition containing the mixed extract of the present invention may contain at least one kind of active ingredients exhibiting the same or similar functions, in addition to the above ingredients.

The composition of the present invention may additionally include pharmaceutically acceptable additives such as starch, gelatinized starch, microcrystalline cellulose, milk sugar, povidone, colloidal silicon dioxide, calcium hydrogen phosphate, lactose, mannitol, malt, gum arabic, pre-gelatinized starch, corn starch, powdered cellulose, hydroxypropyl cellulose, opadry, sodium glycolate starch, carnauba wax, synthetic aluminum silicate, stearic acid, magnesium stearate, aluminum stearate, calcium stearate, sucrose, dextrose, sorbitol, and talc, among others. It is preferable for the pharmaceutically acceptable additives of the present invention to be included at 0.1 wt % to 90 wt % based on the composition, but the additives are not limited thereto.

That is, the composition of the present invention may be administered in various oral and parenteral formulations at the time of conducting actual clinical administration. When the composition is formulated, it may be prepared by using conventional diluents or excipients such as fillers, extenders, binders, wetting agents, disintegrants, surfactants, etc. Solid formulations for oral administration include tablets, pills, granules, capsules, etc., and these solid formulations may be prepared by mixing at least one excipient, e.g., starch, calcium carbonate, sucrose, lactose, or gelatin, with the mixed extract of the present invention. Additionally, lubricants such as magnesium stearate talc, among others, may be used in addition to simple excipients. Liquid formulations for oral administration include suspensions, liquid for internal use, emulsions, and syrups, among others, and various excipients such as humectants, sweetening agents, aromatic agents, and preservatives, among others, can also be included as well as water and liquid paraffin, which are simple diluents. Formulations for parenteral administration may include sterile aqueous solutions, non-aqueous solvents, suspensions, emulsions, lyophilizer, and suppositories. Propylene glycol, polyethylene glycol, vegetable oils such as olive oil, and injectable esters such as ethyl oleate, among others, may be used as the non-aqueous solvents and suspensions. Witepsol, macrogol, tween 61, cacao butter, laurinum, and glycerogelatin, among others, can be used as a base compound of suppositories.

The composition of the present invention may be administered orally or parenterally depending on intended methods. Injection selected from dermatological or intraperitoneal injections, intrarectal injection, hypodermic injection, venous injection, intramuscular injection, or intrathoracic injection is preferable when applying parenteral administration. Dosage varies depending on patient's weight, age, gender, health, diet, administration time, administration method, excretion rate, and severity of disease.

Dosage of the composition of the present invention varies depending on patient's weight, age, gender, health, diet, administration time, administration method, excretion rate, and severity of disease, and daily dosage is 0.0001 mg/kg to 100 mg/kg based on amounts of the mixed extract of the present invention. Preferably, the daily dosage is 0.001 mg/kg to 10 mg/kg, and can be administered 1 to 6 times a day.

The composition of the present invention may be used alone or in conjunction with surgery, radiation therapy, hormone therapy, chemically therapy, and methods using biological response modifiers for preventing and treating diabetic complications or angioedema.

Additionally, the present invention provides a health functional food for preventing and ameliorating diabetic complications and angioedema, containing a cinnamon twig extract as an active ingredient.

The extract is extracted by additionally mixing any one selected from the group consisting of moutan root bark, peony root, and poria.

The extract inhibits the excessive production of advanced glycation end-products, exhibits an effect of fragmentizing a cross-link between advanced glycation end-products and matrix proteins, and inhibits the production of advanced glycation end-products in a human retinal pigment epithelial cell line.

Additionally, the diabetic complications are preferably any one selected from the group consisting of diabetic retinopathy, diabetic cataract, diabetic nephropathy, diabetic neuropathy, diabetic foot ulcers, diabetic heart disease, diabetic osteoporosis, or diabetic arteriosclerosis, but are not limited thereto.

Additionally, the angioedema is preferably any one selected from the group consisting of macular degeneration, macular edema, retinal degeneration, and varicose veins, but is not limited thereto.

The mixed extract of cinnamon twig and moutan root bark, cinnamon twig and peony root, or cinnamon twig and poria is preferably prepared according to the following steps, but is not limited thereto:

1) a step of extracting cinnamon twig and moutan root bark, cinnamon twig and peony root, or cinnamon twig and poria by adding an extraction solvent to each thereof;

2) a step of filtering the extract of step 1); and 3) a step of concentrating the filtered extract of step 2) under reduced pressure;

wherein, in the above method, cinnamon twig, moutan root bark, peony root, and poria used in step 1) can be used without restriction; and can be cultivated or purchased.

It is preferable that the mixed extract is mixed with cinnamon twig and moutan root bark at a weight ratio of 2:1 to 1:10, and then extracted with an extraction solvent. More preferably, they are mixed at a weight ratio of 1:1 to 1:8, and then extracted with an extraction solvent.

It is preferable that the mixed extract is mixed with cinnamon twig and peony root at a weight ratio of 2:1 to 1:10, and then extracted with an extraction solvent. More preferably, they are mixed at a weight ratio of 2:1 to 1:8, and then extracted with an extraction solvent.

It is preferable that the mixed extract is mixed with cinnamon twig and poria at a weight ratio of 2:1 to 1:2, and then extracted with an extraction solvent. More preferably, they are mixed at a weight ratio of 1:1, and then extracted with an extraction solvent.

It is preferable to use water, an alcohol, or a mixture thereof as the extraction solvent. As the alcohol, it is preferable to use $C_1$ to $C_2$ lower alcohols. In addition, it is preferable to use 30% ethanol, 50% ethanol, 70% ethanol, or methanol as lower alcohols. For an extraction method, it is preferable to use a high-temperature decompression method, a hot-water extraction method, a reflux extraction method, a hydrothermal extraction method, a maceration extraction method, a room-temperature extraction method, an ultrasonification extraction method, or a steam extraction method, but the extraction method is not limited thereto. The amount of the extraction solvent is preferably extracted by adding 1 to 10 times the amount of cinnamon twig and moutan root bark, cinnamon twig and peony root, or cinnamon twig and poria. The extraction temperature is preferably from 30° C. to 100° C., but is not limited thereto. Further, the extraction time is preferably 2 hours to 48 hours, but is not limited thereto. Furthermore, the extraction frequency is preferably 2 to 5 times, but is not limited thereto.

In the above method, the reduced pressure concentration of step 3) is preferably accomplished using a vacuum reduced pressure concentrator or a rotary vacuum evaporator, but is not limited thereto. In addition, the concentrate is preferably dried using a reduced-pressure drying method, a vacuum drying method, a boiling drying method, a spray drying method, or a freeze drying method, but is not limited thereto.

The mixed extract may be prepared by mixing cinnamon twig and moutan root bark, cinnamon twig and peony root, or cinnamon twig and poria. In addition, each of cinnamon twig, moutan root bark, peony root, or poria may be extracted, and then mixed to prepare the mixed extract.

The mixed extract of cinnamon twig and moutan root bark, cinnamon twig and peony root, or cinnamon twig and poria according to the present invention has been confirmed to inhibit the excessive production of advanced glycation end-products, which occurs under chronic diabetic conditions, exhibit the effect of fragmentizing a cross-link between the advanced glycation end-products and matrix proteins, have an excellent effect in inhibiting the production of the advanced glycation end-products in a human retinal pigment epithelial cell line subjected to a hyperglycemic or aging environment, and have excellent effects in delaying, preventing, and treating diabetic complications, muscular degeneration, commotio retinae, and lower extremity edema in various animal models of diabetic complications, macular degeneration, and lower extremity edema, and thus the mixed extract of cinnamon twig and moutan root bark, cinnamon twig and peony root, or cinnamon twig and poria can be used as a health functional food for preventing and ameliorating diabetic complications and angioedema.

The health functional food may be prepared and processed in the form of tablets, capsules, powders, granules, liquids, pills, etc., but is not limited thereto. In addition, it can be prepared and processed in any forms pursuant to the law.

The mixed extract of the present invention may be added to foods alone or in combination with different foods or food ingredients. In addition, it may appropriately be used according to conventional methods. The mixed amount of the active ingredient may suitably be determined depending on a purpose (prevention or improvement) of using the active ingredient. Generally, the amount of the mixed extract in health functional foods may be added in 0.1 to 90 parts by weight of the total weight of the food. However, in the case of long-term intake for health and hygiene or health control, the amount may be less than the above range. Alternately, since there is no problem in terms of safety, the active ingredient may be used in an amount greater than the above range.

The composition for a health functional beverage of the present invention may contain the above-described mixed extract as an essential ingredient at a predetermined ratio, and various flavoring agents or natural carbohydrates as additional ingredients without particular limitation, as in a conventional beverage. Examples of the above-described natural carbohydrates include conventional sugars, such as a monosaccharide, for example, glucose, fructose, etc., a disaccharide, for example, maltose, sucrose, etc., and a polysaccharide, for example, dextrin, cyclodextrin, etc., and sugar alcohols such as xylitol, sorbitol, erythritol, etc. In addition to the above-described ingredients, a natural flavoring agent (thaumatin, a *stevia* extract (e.g., rebaudioside A, glycyrrhizin, etc.) and a synthetic flavoring agent (e.g., saccharin, aspartame, etc.) may favorably be used as the flavoring agent.

In addition to the above-described ingredients, the mixed extract of the present invention may further contain various nutritional supplements, vitamins, minerals (electrolytes), flavoring agents such as a synthetic flavoring agent and a natural flavoring agent, a coloring agent and an enhancer (e.g., cheese, chocolate, etc.), pectic acid and a salt thereof, alginic acid and a salt thereof, an organic acid, a protective colloid thickener, a pH regulator, a stabilizer, a preservative, glycerin, an alcohol, and a carbonating agent used in soft drinks. In addition, the extract of the present invention may contain pulps for manufacturing natural fruit juices, fruit juices, and vegetable drinks. Such ingredients may be used independently or in combination with other ingredients. The ratio of these additives is not quite important, but is generally selected in the range of from 0.1 to about 20 parts by weight per 100 parts by weight of the mixed extract of the present invention.

Hereinbelow, the present invention will be described in detail with accompanying exemplary embodiments and experimental embodiments. However, the exemplary and experimental embodiments disclosed herein are only for illustrative purposes and should not be construed as limiting the scope of the present invention.

Example 1: Preparation of Mixed Extract of Cinnamon Twig and Moutan Root Bark

Cinnamon twig and moutan root bark were purchased from Baekjedang, an herbal medicine shop in Daejeon, Korea, and Examples were conducted as follows. In addition, the purchased cinnamon twig and moutan root bark were kept in a cold room of the diabetic complications research team at the Korea Institute of Oriental Medicine.

1-1 Preparation of CMO1, an Extract of Cinnamon Twig and Moutan Root Bark (1:1)

Cinnamon twig (12 g) and moutan root bark (12 g) were mixed at a ratio of 1:1, and then a total of 24 g thereof was added to 50% ethanol (144 mL). Thereafter, the resultant was repeatedly extracted twice under reflux at about 50° C. for about three hours, thereby preparing CMO1, an extract of cinnamon twig and moutan root bark.

1-2 Preparation of CMO1-1, a Hot Water Extract of Cinnamon Twig and Moutan Root Bark (1:1)

Cinnamon twig (90 g) and moutan root bark (90 g) were mixed at a ratio of 1:1, and then a total of 180 g thereof was added to purified water (1080 mL). Thereafter, the resultant was extracted under hot water for about two hours in an herbal-decoction machine, thereby preparing CMO1-1, a hot water extract of cinnamon twig and moutan root bark.

1-3 Preparation of CMO2, an Extract of Cinnamon Twig and Moutan Root Bark (1:2)

In the same manner as Example 1-1 above, cinnamon twig (10 g) and moutan root bark (20 g) were mixed at a ratio of 1:2, and then a total of 30 g thereof was added to 50% ethanol (180 mL). Thereafter, the resultant was repeatedly extracted twice under reflux at about 50° C. for about three hours, thereby preparing CMO2, an extract of cinnamon twig and moutan root bark.

1-4 Preparation of CMO2-1, a Hot Water Extract of Cinnamon Twig and Moutan Root Bark (1:2)

In the same manner as Example 1-2 above, cinnamon twig (60 g) and moutan root bark (120 g) were mixed at a ratio of 1:1, and then a total of 180 g thereof was added to purified water (1080 mL). Thereafter, the resultant was extracted under hot water for about two hours in an herbal-decoction machine, thereby preparing CMO2-1, a hot water extract of cinnamon twig and moutan root bark.

1-5 Preparation of CMO3, an Extract of Cinnamon Twig and Moutan Root Bark (1:4)

In the same manner as Example 1-1 above, cinnamon twig (6 g) and moutan root bark (24 g) were mixed at a ratio of 1:4, and then a total of 30 g thereof was added to 50% ethanol (180 mL). Thereafter, the resultant was repeatedly extracted under reflux at about 50° C. for about three hours, thereby preparing CMO3, an extract of cinnamon twig and moutan root bark.

1-6 Preparation of CMO3-1, a Hot Water Extract of Cinnamon Twig and Moutan Root Bark (1:4)

As the same manner in Example 1-2, cinnamon twig (36 g) and moutan root bark (144 g) were mixed at a ratio of 1:4, and then a total of 180 g thereof was added to purified water (1080 mL). Thereafter, the resultant was extracted under hot water for about two hours in an herbal-decoction machine, thereby preparing CMO3-1, a hot water extract of cinnamon twig and moutan root bark.

1-7 Preparation of CMO4, an Extract of Cinnamon Twig and Moutan Root Bark (1:8)

As the same manner in Example 1-1, cinnamon twig (3.5 g) and moutan root bark (28 g) were mixed at a ratio of 1:8, and then a total of 31.5 g thereof was added to 50% ethanol (190 mL). Thereafter, the resultant was repeatedly extracted under reflux at about 50° C. for about three hours, thereby preparing CMO4, an extract of cinnamon twig and moutan root bark.

1-8 Preparation of CMO4-1, a Hot Water Extract of Cinnamon Twig and Moutan Root Bark (1:8)

As the same manner in Example 1-2, cinnamon twig (20 g) and moutan root bark (160 g) were mixed at a ratio of 1:8, and then a total of 180 g thereof was added to purified water (1080 mL). Thereafter, the resultant was extracted under hot water for about two hours in an herbal-decoction machine, thereby preparing CMO4-1, a hot water extract of cinnamon twig and moutan root bark.

Example 2: Preparation of Mixed Extract of Cinnamon Twig and Peony Root

Cinnamon twig and peony root were purchased from Baekjedang, an herbal medicine shop in Daejeon, Korea, and Examples were conducted as follows. In addition, the purchased cinnamon twig and peony root were kept in a cold room of the diabetic complications research team at the Korea Institute of Oriental Medicine.

2-1 Preparation of CPA1, an Extract of Cinnamon Twig and Peony Root (2:1)

In the same manner as Example 1-1, cinnamon twig (16 g) and peony root (8 g) were mixed at a ratio of 2:1, and then a total of 24 g thereof was added to 50% ethanol (144 mL). Thereafter, the resultant was repeatedly extracted twice under reflux at about 50° C. for about three hours, thereby preparing CPA1, an extract of cinnamon twig and peony root.

2-2 Preparation of CPA1-1, a Hot Water Extract of Cinnamon Twig and Peony Root (2:1)

In the same manner as Example 1-2, cinnamon twig (120 g) and moutan root bark (60 g) were mixed at a ratio of 2:1, and then a total of 180 g thereof was added to purified water (1080 mL). Thereafter, the resultant was extracted under hot water for about two hours in an herbal-decoction machine, thereby preparing CPA1-1, a hot water extract of cinnamon twig and peony root.

2-3 Preparation of CPA2, an Extract of Cinnamon Twig and Peony Root (1:2)

In the same manner as Example 1-1, cinnamon twig (10 g) and peony root (20 g) were mixed at a ratio of 1:2, and then a total of 30 g thereof was added to 50% ethanol (180 mL). Thereafter, the resultant was repeatedly extracted twice under reflux at about 50° C. for about three hours, thereby preparing CPA2, an extract of cinnamon twig and peony root.

2-4 Preparation of CPA2-1, a Hot Water Extract of Cinnamon Twig and Peony Root (1:2)

In the same manner as Example 1-2, cinnamon twig (60 g) and peony root (120 g) were mixed at a ratio of 1:2, and then a total of 180 g thereof was added to purified water (1080 mL). Thereafter, the resultant was extracted under hot water for about two hours in an herbal-decoction machine, thereby preparing CPA2-1, a hot water extract of cinnamon twig and peony root.

2-5 Preparation of CPA3, an Extract of Cinnamon Twig and Peony Root (1:4)

In the same manner as Example 1-1, cinnamon twig (6 g) and peony root (24 g) were mixed at a ratio of 1:4, and then a total of 30 g thereof was added to 50% ethanol (180 mL). Thereafter, the resultant was repeatedly extracted twice under reflux at about 50° C. for about three hours, thereby preparing CPA3, an extract of cinnamon twig and peony root.

2-6 Preparation of CPA3-1, a Hot Water Extract of Cinnamon Twig and Peony Root (1:4)

In the same manner as Example 1-2, cinnamon twig (36 g) and peony root (144 g) were mixed at a ratio of 1:4, and then a total of 180 g thereof was added to purified water (1080 mL). Thereafter, the resultant was extracted under hot water for about two hours in an herbal-decoction machine, thereby preparing CPA3-1, a hot water extract of cinnamon twig and peony root.

2-7 Preparation of CPA4, an Extract of Cinnamon Twig and Peony Root (1:8)

In the same manner as Example 1-1, cinnamon twig (3.5 g) and peony root (28 g) were mixed at a ratio of 1:8, and then a total of 31.5 g thereof was added to 50% ethanol (190 mL). Thereafter, the resultant was repeatedly extracted twice under reflux at about 50° C. for about three hours, thereby preparing CPA4, an extract of cinnamon twig and peony root.

2-8 Preparation of CPA4-1, a Hot Water Extract of Cinnamon Twig and Peony Root (1:8)

In the same manner as Example 1-2, cinnamon twig (20 g) and peony root (160 g) were mixed at a ratio of 1:8, and then a total of 180 g thereof was added to purified water (1080 mL). Thereafter, the resultant was extracted under hot water for about two hours in an herbal-decoction machine, thereby preparing CPA4-1, a hot water extract of cinnamon twig and peony root.

Example 3: Preparation of Mixed Extract of Cinnamon Twig and Poria

Cinnamon twig and poria were purchased from Baekjedang, an herbal medicine shop in Daejeon, Korea, and Examples were conducted as follows. In addition, the purchased cinnamon twig and poria were kept in a cold room of the diabetic complications research team at the Korea Institute of Oriental Medicine.

3-1 Preparation of CPO, an Extract of Cinnamon Twig and poria (1:1)

In the same manner as Example 1-1, cinnamon twig (12 g) and poria (12 g) were mixed at a ratio of 1:1, and then a total of 24 g thereof was added to 50% ethanol (144 mL). Thereafter, the resultant was repeatedly extracted twice under reflux at about 50° C. for about three hours, thereby preparing CPO, an extract of cinnamon twig and poria.

Example 4: Preparation of KBT, a Mixed Extract of Cinnamon Twig, Poria, Moutan Root Bark, *Radix paeoniae rubra*, and Peach Kernel The same amount of each of cinnamon twig, poria, moutan root bark, *Radix paeoniae rubra*, and peach kernel were mixed, and 10 volumes of distilled water was added thereto. Thereafter, the resultant was decocted for about two hours using a super-speed vacuum low-temperature extraction machine, extracted at high temperature under reduced pressure, and dried, thereby preparing KBT, which is the extract used as a control group.

Example 5: Preparation of KJT, a Mixed Extract of Cinnamon Twig, Peony Root, Licorice, Ginger, and Jujube Cinnamon twig, peony root, licorice, ginger, and jujube were mixed at a ratio of 3:2:1:1:1, and 10 volumes of distilled water was added thereto. Thereafter, the resultant was decocted for about two hours using a super-speed vacuum low-temperature extraction machine, extracted at high temperature under reduced pressure, and dried, thereby preparing KJT, which is the extract used as a control group.

Example 6: Analysis of Ingredients in Cinnamon Twig and Moutan Root Bark Extract and Cinnamon Twig and Peony Root Extract In order to confirm the ingredients of CMO4 (extract of cinnamon twig and moutan root bark), CMO4-1 (hot water extract of cinnamon twig and moutan root bark), CPA4 (extract of cinnamon twig and peony root), and CPA4-1 (hot water extract of cinnamon twig and peony root), HPLC analysis was conducted.

As a result, as shown in FIG. 1, it was confirmed that the index ingredients of CMO4 (extract of cinnamon twig and moutan root bark) and CMO4-1 (hot water extract of cinnamon twig and moutan root bark) were gallic acid, oxypaeoniflorin, albiflorin, paeoniflorin, benzoic acid, cinnamic acid, cinnamaldehyde, and paeonol (FIGS. 1a to 1b). In addition, it was also confirmed that the index ingredients of CPA4 (extract of cinnamon twig and peony root) and CPA4-1 (hot water extract of cinnamon twig and peony root) were gallic acid, oxypaeoniflorin, albiflorin, paeoniflorin, benzoic acid, cinnamic acid, and cinnamaldehyde (FIGS. 1c to 1d). In addition, as shown in Table 1 below, the content of paeoniflorin in each extract was confirmed (Table 1).

TABLE 1

|  | Content (%) of paeoniflorin (PF) |
|---|---|
| CMO4 (extract of cinnamon twig and moutan root bark) | 2.7 |
| CMO4-1 (hot water extract of cinnamon twig and moutan root bark) | 2.3 |
| CPA4 (extract of cinnamon twig and peony root) | 12.3 |
| CPA4-1 (hot water extract of cinnamon twig and peony root) | 8.9 |

Experimental Example 1: Inhibition of Producing Advanced Glycation End-Products (AGEs)

The present inventors analyzed an inhibitory effect of producing in vitro advanced glycation end-products of the mixed extract containing cinnamon twig, which was prepared in Examples 1 to 5.

Specifically, 10 mg/mL of bovine serum albumin (BSA, Sigma, USA) dissolved in 50 mM phosphate buffer (pH 7.4) was used as a protein source, and the solution mixed with 0.2 M fructose and 0.2 M glucose was used as a sugar source. The extracts of Examples and aminoguanidine (positive control group) were dissolved in 0.2% dimethylsulfoxide (DMSO), followed by dissolving again in 15% tween 80. The thus-prepared protein source, sugar source, and extracts were mixed, prepared at 1 mL in total, cultured at 37° C. for seven days, and allowed to undergo glycation. Herein, 0.02% sodium azide, an antibacterial agent, was added to prevent bacterial production. After cultivation, the fluorescence was measured at an absorption wavelength of 350 nm and an emission wavelength of 450 nm using a spectrofluorometric detector (Bio-TEK, USA). It was calculated as shown in Equation 1 below, and the results are shown in Table 2 below.

$$\text{Inhibitory rate of production } (\%) = \left[ 100 - \frac{\left(\begin{array}{c}\text{fluorescence intensity of}\\\text{experimental group sample}\end{array}\right) * \left(\begin{array}{c}\text{fluorescence intensity}\\\text{of empty sample}\end{array}\right)}{\left(\begin{array}{c}\text{fluorescence intensity of}\\\text{control group sample}\end{array}\right) * \left(\begin{array}{c}\text{fluorescence intensity of}\\\text{control group empty sample}\end{array}\right)} \right] * 100$$

Equation 1

As a result, as shown in Table 2 below, it was confirmed that CMO1, CMO2, CMO3, and CMO4, which are the extracts of cinnamon twig and moutan root bark, exhibited an inhibitory effect against the production of advanced glycation end-products. That is, the inhibitory effect of CMO1, CMO2, CMO3, and CMO4 against the production of advanced glycation end-products was respectively 17-fold, 21.3-fold, 21.3-fold, and 22.7-fold higher than that of aminoguanidine, the positive control group. Further, CPA1, CPA2, CPA3, and CPA4, which are the extracts of cinnamon twig and peony root, respectively exhibited an inhibitory effect against the production of advanced glycation end-products 8-fold, 10.9-fold, 10.1-fold, and 12.1-fold higher than that of aminoguanidine, the positive control group. Furthermore, CPO, which is the extract of cinnamon twig and poria, exhibited an inhibitory effect against the production of advanced glycation end-products 4-fold higher than that of aminoguanidine, the positive control group (Table 2).

Additionally, it was confirmed that CMO1, CMO2, CMO3, and CMO4, which are the extracts of cinnamon twig and moutan root bark, and CPA1, CPA2, CPA3, and CPA4, which are the extracts of cinnamon twig and poria, respectively exhibited an inhibitory effect against the production of advanced glycation end-products 4.8-fold, 5.9-fold, 5.9-fold, 6.3-fold, 2.3-fold, 3.0-fold, 2.8-fold, 3.4-fold, and 1.1-fold higher than the inhibitory effect of KBT, the extract of Example 4. Further, it was also confirmed that CMO1, CMO2, CMO3, and CMO4, which are the extracts of cinnamon twig and moutan root bark, and CPA1, CPA2, CPA3, and CPA4, which are the extracts of cinnamon twig and peony root, and CPO, which is the extract of cinnamon twig and poria, respectively exhibited inhibitory effect against the production of advanced glycation end-products 8.5-fold, 10.4-fold, 10.4-fold, 10.4-fold, 11.1-fold, 4.1-fold, 5.4-fold, 8.6-fold, and 2.0-fold higher than the inhibitory effect of KJT, the extract of Example 5 (Table 2).

Accordingly, considering that aminoguanidine, which is the positive control group, is a single synthetic compound, it was confirmed that the extracts of cinnamon twig and moutan root bark, the extracts of cinnamon twig and peony root, or the mixed extract of cinnamon twig and poria according to the present invention exhibited a remarkably superior inhibitory effect against the production of advanced glycation end-products. At the same time, it was also confirmed that the extracts of cinnamon twig and moutan root bark, the extracts of cinnamon twig and peony root, or the mixed extract of cinnamon twig and poria were remarkably superior compared with KBT (the extract of Example 4) or KJT (the extract of Example 5).

TABLE 2

| Sample | $IC_{50}$ (μg/mL) | Comparison of effect | | |
|---|---|---|---|---|
| | | Contrast with AG (positive control group) | Contrast with KBT (extract of Example 4) | Contrast with KJT (extract of Example 5) |
| KBT (extract in Example 4) | 22.96 ± 0.49 | ×3.6 | | |
| KJT (extract in Example 5) | 40.43 ± 2.20 | ×2.0 | | |
| CMO1 (extract of cinnamon twig and moutan root bark (1:1) in Example 1-1) | 4.78 ± 0.12 | ×17 | ×4.8 | ×8.5 |
| CMO2 (extract of cinnamon twig and moutan root bark (1:2) in Example 1-2) | 3.87 ± 0.09 | ×21.3 | ×5.9 | ×10.4 |
| CMO3 (extract of cinnamon twig and moutan root bark (1:4) in Example 1-3) | 3.87 ± 0.12 | ×21.3 | ×5.9 | ×10.4 |
| CMO4 (extract of cinnamon twig and moutan root bark (1:8) in Example 1-4) | 3.63 ± 0.17 | ×22.7 | ×6.3 | ×10.4 |
| CPA1 (extract of cinnamon twig and peony root (2:1) in Example 2-1) | 9.94 ± 0.20 | ×8.0 | ×2.3 | ×11.1 |
| CPA2 (extract of cinnamon twig and peony root (1:2) in Example 2-2) | 7.54 ± 0.18 | ×10.9 | ×3.0 | ×4.1 |
| CPA3 (extract of cinnamon twig and peony root (1:4) in Example 2-3) | 8.16 ± 0.23 | ×10.1 | ×2.8 | ×5.4 |
| CPA4 (extract of cinnamon twig and peony root (1:8) in Example 2-4) | 6.84 ± 0.08 | ×12.1 | ×3.4 | ×8.6 |
| CPO (extract of cinnamon twig and poria (1:1) extract in Example 3-1) | 20.46 ± 0.36 | ×4.0 | ×1.1 | ×2.0 |
| AG (aminoguanidine, positive control group) | 82.50 ± 1.10 | — | | |

Experimental Example 2: Inhibitory Effect Against the Production of Advanced Glycation End-Products in Extracellular Matrix (ECM) Treated with Glycoaldehyde After treating the mixed extracts prepared in Examples 1 and 2 with glycoaldehyde, an inhibitory effect against the production of advanced glycation end-products was confirmed.

The extracellular matrix (ECM) (Sigma-Aldrich, Cat. No. c-3867) was set to 10 μg/cm², dispensed into a 96-black well plate, and then coated overnight at 4° C. On the following day, the ECM in the coated plate was removed, completely dried at room temperature, and then mixed together with 100 mM glycoaldehyde (Sigma-Aldrich) and already-diluted extracts at various concentrations (1 μg/mL, 5 μg/mL, 10 μg/mL, 20 μg/mL, and 50 μg/mL), so that the total volume thereof became 100 μL. Thereafter, the resultant was reacted at 37° C. for four hours, and whether it inhibited the production of advanced glycation end-products (AGEs) was confirmed. For the positive control group, only 100 mM glycoaldehyde (Sigma-Aldrich) was added to the coated plate to confirm the production of advanced glycation endproducts. After washing the resultant and positive group twice with PBS, 50 mM sodium borohydride (Sigma-Aldrich) was added, and the remaining aldehyde group was then neutralized for five minutes. After the neutralization, they were washed twice with PBS, and then PBS (100 μL) was again added thereto to confirm using fluorescence spectroscopy (Ex. 370 nm/Em 440 nm). For the statistical analysis, a significant value was made to be p<0.05 using the Prism 5.0 program (GraphPad).

As a result, as shown in FIG. 2, it was confirmed that CMO4 and CMO4-1, the extracts of cinnamon twig and moutan root bark, and CPA4 and CPA4-1, the extracts of cinnamon twig and peony root, according to the present invention significantly inhibited the production of advanced glycation end-products in a concentration-dependent manner (1 μg/mL, 5 μg/mL, 10 μg/mL, 20 μg/mL, and 50 μg/mL) (FIG. 2).

Experimental Example 3: Effect of Fragmentizing Cross-Link of Advanced Glycation End-Products An effect of the mixed extract prepared in Examples 1 to 3, in which a cross-link between advanced glycation end-products and matrix proteins was fragmentized, was confirmed. ALT-711 (Alteon Inc., Ramsey, N.J.) was used for a positive control group.

Specifically, 1.0 μg of AGE-BSA (Transgenic Inc. Kobe, Japan) was dispensed into a collagen-coated 96-well microtiter plate (Greiner Bio-One, Germany) and cultured at 37° C. for four hours, and then the AGE-BSA and collagen were allowed to cross-link. After washing the resultant three times with PBST (0.05%) to remove AGE-BSA not linked, a mixed extract and ALT-711 were added, and cultured at 37° C. for four hours. Thereafter, the resultant was washed with PBST (0.05%), and in order to detect the AGE-BSA remaining due to the cross-link to collagen, mouse monoclonal anti-AGE-BSA antibodies (6D12, Transgenic Inc. Kobe, Japan) were diluted at 1:250 and dispensed, followed by cultivation at 37° C. for one hour. After one hour, the resultant was washed with PBST (0.05%) and reacted with HRP-linked goat anti-mouse IgG antibodies (Santa Cruz, USA) to develop TMB (3.3',5,5'-tetramethylbenzidine) as a substrate. Thereafter, absorbance was measured at 450 nm. The cross-link fragmentation effect (%) of AGE-BSA was calculated as shown in the following Equation 2.

$$\text{Fragmentation effect (\%)} = \frac{\text{absorbance of well to which drug was added}}{\text{absorbance of well to which drug was not added}} \times 100 \qquad \text{Equation 2}$$

As a result, as shown in Table 3 below, it was confirmed that CMO1, CMO1-1, CMO2, CMO2-1, CMO3, CMO3-1, CMO4, and CMO4-1, which are the extracts of cinnamon twig and moutan root bark, respectively exhibited a cross-link fragmentation effect of advanced glycation end-products, 1183-fold, 12362-fold, 16726-fold, 4352-fold, 13225-fold, 3419-fold, 11685-fold, and 3281-fold higher than that of ALT-711, the positive control group. Further, it was also confirmed that CPA1, CPA1-1, CPA2, CPA2-1, CPA3, CPA3-1, CPA4, and CPA4-1, which are the extracts of cinnamon twig and peony root, respectively exhibited a cross-link fragmentation effect of advanced glycation end-products, 2221-fold, 13124-fold, 1965-fold, 12362-fold, 2093-fold, 11373-fold, 1977-fold, and 7515-fold higher than that of ALT-711, the positive control group. Furthermore, CPO, which is the extract of cinnamon twig and poria, exhibited a cross-link fragmentation effect of advanced glycation end-products 3495-fold higher than that of ALT-711, the positive control group (Table 3).

Accordingly, it was confirmed that the extracts of cinnamon twig and moutan root bark, the extracts of cinnamon twig and peony root, or the extract of cinnamon twig and poria have a superior cross-link fragmentation effect compared to ALT-711, the positive control group. In particular, considering that ALT-711, the positive control group, is a single synthetic compound, it was confirmed that the mixed extracts of the present invention have a remarkably superior effect.

TABLE 3

| Sample | IC$_{50}$ (μg/mL) | Comparison of effect Contrast with ALT-711 |
|---|---|---|
| CMO1 (extract of cinnamon twig and moutan root bark (1:1) in Example 1-1) | 14.41 ± 8.94 | ×1183 |
| CMO1-1 (hot water extract of cinnamon twig and moutan root bark (1:1) in Example 1-2) | 1.38 ± 0.37 | ×12362 |
| CMO2 (extract of cinnamon twig and moutan root bark (1:2) in Example 1-3) | 1.02 ± 0.15 | ×16725.5 |
| CMO2-1 (hot water extract of cinnamon twig and moutan root bark (1:2) in Example 1-4) | 3.92 ± 1.09 | ×4352 |
| CMO3 (extract of cinnamon twig and moutan root bark (1:4) in Example 1-5) | 1.29 ± 0.70 | ×13224.8 |
| CMO3-1 (hot water extract of cinnamon twig and moutan root bark (1:4) in Example 1-6) | 4.99 ± 2.53 | ×3419 |
| CMO4 (extract of cinnamon twig and moutan root bark (1:8) in Example 1-7) | 1.46 ± 0.65 | ×11685 |
| CMO4-1 (hot water extract of cinnamon twig and moutan root bark (1:8) in Example 1-8) | 5.20 ± 1.18 | ×3281 |
| CPA1 (extract of cinnamon twig and peony root (2:1) in Example 2-1) | 7.68 ± 3.78 | ×2221 |
| CPA1-1 (hot water extract of cinnamon twig and peony root (2:1) in Example 2-2) | 1.30 ± 0.37 | ×13124 |

TABLE 3-continued

| Sample | IC$_{50}$ (μg/mL) | Comparison of effect Contrast with ALT-711 |
|---|---|---|
| CPA2 (extract of cinnamon twig and peony root (1:2) in Example 2-3) | 8.68 ± 0.90 | ×1965 |
| CPA2-1 (hot water extract of cinnamon twig and peony root (1:2) in Example 2-4) | 1.38 ± 0.24 | ×12362 |
| CPA3 (extract of cinnamon twig and peony root (1:4) in Example 2-5) | 8.15 ± 0.39 | ×2093 |
| CPA3-1 (hot water extract of cinnamon twig and peony root (1:4) in Example 2-6) | 1.50 ± 1.64 | ×11373 |
| CPA4 (extract of cinnamon twig and peony root (1:8) in Example 2-7) | 8.63 ± 0.70 | ×1977 |
| CPA4-1 (hot water extract of cinnamon twig and peony root (1:8) in Example 2-8) | 2.27 ± 0.38 | ×7515 |
| CPO (extract of cinnamon twig and poria (1:1) in Example 3-1) | 4.88 ± 1.34 | ×3495 |
| ALT-711 (positive control group) | 17,060 ± 2.35 | — |

Experimental Example 4: Inhibitory Effect Against Production of Advanced Glycation End-Products in Human Retinal Pigment Epithelial Cell Line Under Hyperglycemic Environment The inhibitory effect against the production of advanced glycation end-products in a human retinal pigment epithelial cell line under a hyperglycemic environment was confirmed from CMO2, CMO4, and CMO4-1, which are extracts of cinnamon twig and moutan root bark, and CPA1-1, CPA2-1, CPA4, and CPA4-1, which are extracts of cinnamon twig and peony root, prepared in Examples 1 and 2.

Specifically, a human pigment epithelial cell line (ARPE-19: ATCC No. CRL-2302) was cultured in a 5% CO$_2$ incubator using Dulbecco's modified Eagles medium (DMEM, Gibco, USA) under a hyperglycemic environment. After culturing the human pigment epithelial cell line under a hyperglycemic condition (25 mM) containing the final concentration of BSA (500 μg/mL), CMO2, CMO4, and CMO4-1, which are the extracts of cinnamon twig and moutan root bark, and CPA1-1, CPA2-1, CPA4, and CPA4-1, which are the extracts of cinnamon twig and peony root, were treated in each concentration (10 μg/mL, 20 μg/mL, and 50 μg/mL). In addition, aminoguanidine (AG, 10 mM) was also treated for the positive control group. After washing with 1×PBS, samples were treated with LaemmLi Sample Buffer (Cat. No. 161-0737, Bio-Rad Laboratories, CA, USA), boiled at 100° C. for five minutes, and then used after proteins for the samples were quantified using BCA (Pierce Biotechnology, IL, USA). Proteins were electrophoresed at 120 V for two hours on 10% polyacrylamide gel containing SDS (PAGE), and then the protein was transferred to a PVDF membrane (Bio-Rad Laboratories, CA, USA) at 250 mA for 1.5 hours by transfer buffer (0.25 M Tris, 1.92 M Glycine, pH 8.3 to 8.4). After blocking with 5% non fat milk in TBS-T (200 mM Tris, 1.37 M NaCl, 0.05% Tween 20) solution, AGEs antibodies (Anti-AGEs monoclonal Ab, Clone No. 6D12) were reacted at 4° C. After washing, HRP-conjugated secondary antibodies were reacted, washed again, and reacted by enhanced chemiluminescence (ECL) for analysis using LAS-3000 (Fuji film, JPN). Thereafter, the results were statistically analyzed using GraphPad Prism 5 (San Diego).

As a result, as shown in FIG. 3, it was confirmed that CMO2, CMO4, and CMO4-1, which are the extracts of cinnamon twig and moutan root bark, and CPA1-1, CPA2-1, CPA4, and CPA4-1, which are the extracts of cinnamon twig and peony root, also exhibited the production of advanced glycation end-products in a human retinal pigment epithelial cell line under a hyperglycemic environment, in a concentration-dependent manner (10 μg/mL, 20 μg/mL, and 50 μg/mL) (FIG. 3).

Based on the results above, it was confirmed that the extracts of cinnamon twig and moutan root bark, the extracts of cinnamon twig and peony root, and the extract of cinnamon twig and poria inhibited the production of advanced glycation end-products, inhibited the production of advanced glycation end-products in ECM coated with glycoaldehyde, fragmentized a cross-link between the already-produced advanced glycation end-products and matrix proteins, and significantly inhibited the production of advanced glycation end-products in a human retinal pigment epithelial cell line under a hyperglycemic environment.

Experimental Example 5: Preventive Effect of Diabetic Complications in Animal Model In order to confirm a preventive effect of CMO4-1, which is the hot water extract of cinnamon twig and moutan root bark (1:8), and CPA4-1, which is the hot water extract of cinnamon twig and peony root (1:8), against diabetic complications in a type 2 diabetes model, db/db mice, CMO4-1 (hot water extract of cinnamon twig and moutan root bark (1:8)) and CPA4-1 (hot water extract of and cinnamon twig and peony root (1:8)) were administered to the db/db mice for 12 weeks. Fenofibrate, a drug approved in Australia for treating diabetic retinopathy, was used as the positive control group.

5-1 Experimental Animal Breeding and Experimental Design 7-week-old male db/db mice, a type 2 diabetes animal model in which diabetes was developed due to a mutation in a leptin receptor, were divided into seven groups by providing 10 mice in each group as follows:

(1) normal animal group (non-diabetic heterozygote db/+ mice, NOR); (2) Diabetic animal group (C57BL/KsJ-Lepr$^{db/db}$ diabetic mice, DM); (3) FENO (group administered with fenofibrate 100 mg/kg/day); (4) CMO4-1-100 (group administered with CMO4-1 100 mg/kg/day); (5) CMO4-1-250 (group administered with CMO4-1 250 mg/kg/day); (6)

CPA4-1-100 (group administered with CPA4-1 100 mg/kg/day); and (7) CPA4-1-250 (group administered with CPA4-1 250 mg/kg/day).

All drugs were suspended in 0.5% methylcellulose, and orally administered once a day for 12 weeks. The same amount of only 0.5% methylcellulose solution, a vehicle solution, was orally administered in experimental groups (1) and (2). Body weight and feed and water intakes during the drug administration period were measured.

5-2 Inhibitory Effect Against Damage to Blood-Retinal Barrier

If hyperglycemia persists, the blood-retinal barrier will be damaged due to dysfunction of retinal blood vessels in the eyeball. In this regard, after administering CMO4-1 (hot water extract of cinnamon twig and moutan root bark (1:8)) and CPA4-1 (hot water extract of cinnamon twig and peony root (1:8)), an effect of inhibiting the damage to the blood-retinal barrier was confirmed.

Specifically, mice in the experimental group designed as in Experimental Example 5-1 were anesthetized by intraperitoneally injecting pentobarbital sodium (25 mg/kg), and the peritoneal cavity and thoracic cavity were opened to secure the heart. In addition, 50 mg/mL of fluorescein-dextran ($2 \times 10^6$ molecular weight) which was prepared by dissolving in sterilized PBS (1 mL) was injected into the left ventricle. After 10 minutes, the eyeballs were enucleated, and the left eyeball was placed in an eyecup. The separated retina was placed on a slide, and then mounted using an aqueous mounting medium. After this was sufficiently dried, a fluorescence microscope was used to observe the same.

As a result, as shown in FIG. 4, it was confirmed that although fluorescence outflow was not observed in the normal group (NOR), fluorescent substances released due to the damage to the blood-retinal barrier were significantly increased in the diabetic group (DM). In addition, it was also confirmed that the outflow of fluorescent substances was not prevented in the fenofibrate-administered group (FENO), the positive control group. However, CMO4-1-100 and CMO4-1-250, which are the groups administered with a hot water extract of cinnamon twig and moutan root bark (1:8), and CPA4-1-100, which is the group administered with a hot water extract of cinnamon twig and peony root (1:8), according to the present invention significantly prevented the outflow of fluorescent substances from retina vessels (FIG. 4).

5-3 Inhibitory Effect Against Formation of Acellular Capillary

One of the initial symptoms of diabetic retinopathy is the formation of acellular capillaries, which kills the nuclei of pericytes to cause retinopathy. In this regard, an inhibitory effect against the formation of acellular capillaries was confirmed after administering CMO4-1 (hot water extract of cinnamon twig and moutan root bark (1:8)) and CPA4-1 (hot water extract of cinnamon twig and peony root (1:8)) prepared in Examples 1 and 2.

Specifically, eyeballs were enucleated from mice in the same manner as Experimental Example 5-2, and retinas were enucleated from the eyeballs and washed with running water. Thereafter, they were placed in 3% trypsin and cultured at 37° C. for one hour. The digested retinas were transferred to PBS, and the internal membrane (membrane of organelle present in cells) was removed. The vascular frame was separated from the retinal background using a glass rod, placed on a slide, and dried. The dried vascular frame was then stained with PAS and hematoxylin, and variations in cell walls and nuclei were confirmed.

As a result, as shown in FIG. 5, it was confirmed that although the formation of acellular capillaries was not observed in the normal group (NOR), the number of acellular capillaries was significantly increased in the diabetic group (DM). In addition, it was also confirmed that the formation of acellular capillaries was not prevented in the fenofibrate-administered group (FENO). However, CMO4-1-100 and CMO4-1-250, which are the hot water extracts of cinnamon twig and moutan root bark (1:8), and CPA4-1-100, which is the hot water extract of cinnamon twig and peony root (1:8), according to the present invention significantly prevented the formation of acellular capillaries (FIG. 5).

5-4 Inhibitory Effect Against Damage to Tight-Junction Protein Between Cells

An inhibitory effect against the damage to occludin, a tight-junction protein between cells, was confirmed after administering CMO4-1 (hot water extract of cinnamon twig and moutan root bark (1:8)) and CPA4-1 (hot water extract of cinnamon twig and peony root (1:8)), which were prepared in Examples 1 and 2.

Specifically, eyeballs in mice were enucleated in the same manner as Experimental Example 5-2, and fixed in 10% neutralized formalin overnight. In addition, the resultant was dehydrated and substituted three times with xylene, thereby embedding the same with paraffin. Blocks of the embedded tissue were prepared as serial sections in a thickness of 4 µm, and placed on slides for use. In order to remove an endogenous peroxidase activity, a slide which underwent deparaffinization and function processes was allowed to react with 3% hydrogen peroxide solution for 10 minutes, and then washed three times with PBS containing 0.05% tween 20. In order to remove non-specific reactions, 5% casein was used for blocking, and then primary antibodies were diluted at a ratio of 1:200, respectively. Thereafter, the diluted primary antibodies were treated for one hour or overnight. After washing with PBS for one hour, a labeled streptoavidin biotin (LSAB) kit (Dako, USA) was applied to the resultants, developed with DAB, and then observed using an optical microscope. In the case of fluorescent staining, FITC-conjugated secondary antibodies were diluted at a ratio of 1:200, respectively, and reacted for one hour. Thereafter, the resultants were stained with DAPI and observed using a fluorescence microscope.

As a result, as shown in FIG. 6, although it was confirmed that connection lines such as the threads of occludin were snapped in the diabetic group (DM), there was no occludin loss in the fenofibrate-administered group (FENO) and the groups administered with a hot water extract of cinnamon twig and moutan root bark (1:8), which are CMO4-1-100 and CMO4-1-250 (FIG. 6).

Experimental Example 6: Therapeutic Effect of Diabetic Complications in Animal Model In order to confirm a therapeutic effect of co-administration of CMO4 (extract of cinnamon twig and moutan root bark (1:8)), CPA4 (extract of cinnamon twig and peony root (1:8)), and metformin, metformin was administered to a type 2 diabetes model, db/db mice, for 12 weeks to regulate blood glucose level. Thereafter, CMO4 (extract of cinnamon twig and moutan root bark (1:8)) and CPA4 (extract of cinnamon twig and peony root (1:8)) were co-administered with metformin for an additional 12 weeks to confirm the therapeutic effect of CMO4 (extract of cinnamon twig and moutan root bark (1:8)) and CPA4 (extract of cinnamon twig and peony root (1:8)) on diabetic retinopathy and nephropathy. Fenofibrate, a drug approved in Australia for treating diabetic retinopathy, was used as the positive control group.

6-1 Experimental Animal Breeding and Experimental Design 7-week-old male db/db mice, a type 2 diabetes animal model in which diabetes were developed due to a mutation in a leptin receptor, were divided into eight groups by providing 10 mice in each group as follows:

(1) normal animal group (non-diabetic heterozygote db/+ mice, NOR); (2) Diabetic animal group (C57BL/KsJ-Lepr$^{db/db}$ diabetic mice, DM); (3) MET (group administered with metformin 350 mg/kg/day); (4) MET+FENO (group administered with metformin and fenofibrate 100 mg/kg/day); (5) MET+CMO4-100 (group administered with metformin and CMO4 100 mg/kg/day); (6) MET+CMO4-250 (group administered with metformin and CMO4 250 mg/kg/day); (7) MET+CPA4-100 (group administered with metformin and CPA4 100 mg/kg/day); and (8) MET+CPA4-250 (group administered with metformin and CPA4 250 mg/kg/day).

In groups (3) to (8), metformin (350 mg/kg) was administered for 12 weeks in order to lower the blood glucose level to a certain level. Metformin and extracts were suspended in 0.5% methylcellulose, and orally administered once a day for 12 weeks. The same amount of only 0.5% methylcellulose solution, a vehicle solution, was orally administered in experimental groups (1) and (2). After administering metformin for 12 weeks, a determined amount of extracts corresponding to each group was added to metformin daily for co-administration. Body weight and feed and water intakes during the drug administration period were measured, and blood glucose levels were measured at intervals of four weeks.

6-2 Inhibitory Effect Against Damage to Blood-Retinal Barrier

If hyperglycemia persists, the blood-retinal barrier will be damaged due to dysfunction of retinal blood vessels in the eyeball. In this regard, after administering CMO4 (extract of cinnamon twig and moutan root bark (1:8)) and CPA4 (extract of cinnamon twig and peony root (1:8)), an effect of inhibiting the damage to the blood-retinal barrier was confirmed.

Specifically, mice in the experimental group designed as in Experimental Example 6-1 were anesthetized by intraperitoneally injecting pentobarbital sodium (25 mg/kg), and the peritoneal cavity and thoracic cavity were opened to secure the heart. In addition, 50 mg/mL of fluorescein-dextran ($2\times10^6$ molecular weight) which was prepared by dissolving in sterilized PBS (1 mL) was injected into the left ventricle. After 10 minutes, the eyeballs were enucleated, and the left eyeball was placed in an eyecup. The separated retina was placed on a slide, and then mounted using aqueous mounting medium. After this was sufficiently dried, a fluorescence microscope was used to observe the same. The results were confirmed at 12 weeks, 18 weeks, and 24 weeks of inducing diabetes, respectively.

As a result, as shown in FIG. 7, it was confirmed that although fluorescence outflow was not observed until 24 weeks in the normal group (NOR), the diabetic group (DM) exhibited a phenomenon in which fluorescent substances leaked out of blood vessels due to the damage to the blood-retinal barrier, and which was confirmed in the majority of subjects at 12 weeks, 18 weeks, and 24 weeks. In addition, in MET, the metformin-administered group, which is the positive control group, the outflow of the fluorescent substances was significantly reduced at 18 weeks compared to the diabetic group (DM), but the outflow of the fluorescent substances was not prevented at 24 weeks. In MET+FENO, the group co-administered with metformin and fenofibrate, the outflow of the fluorescent substances was prevented at 18 weeks, but there was no effect of preventing the outflow of the fluorescent substances at 24 weeks. In addition, when CMO4-100 and CMO4-250 (groups administered with cinnamon twig and moutan root bark (1:8)) and CPA4-100 and CPA4-250 (groups administered with cinnamon twig and peony root (1:8)) according to the present invention were co-administered with metformin, respectively, it was confirmed that these groups have the therapeutic effect by significantly preventing the outflow of the fluorescent substances from retinal blood vessels at 18 and 24 weeks (FIG. 7).

Based on the results above, it was confirmed that metformin can prevent the damage to retinal blood vessels during a certain period of time, but metformin has a limitation in that the damage to retinal blood vessels is ultimately not prevented.

6-3 Inhibitory Effect Against Formation of Acellular Capillaries

One of the initial symptoms of diabetic retinopathy is the formation of acellular capillaries, which kills the nuclei of pericytes to cause retinopathy. In this regard, the inhibitory effect against the formation of acellular capillaries was confirmed after administering CMO4 (extract of cinnamon twig and moutan root bark (1:8)) and CPA4 (extract of cinnamon twig and peony root (1:8)) prepared in Examples 1 and 2.

Specifically, eyeballs were enucleated from mice in the same manner as Experimental Example 6-2, and retinas were enucleated from the eyeballs and washed with running water. Thereafter, they were placed in 3% trypsin and cultured at 37° C. for one hour. The digested retinas were transferred to PBS, and the internal membrane (membrane of organelle present in cells) was removed. The vascular frame was separated from the retinal background using a glass rod, placed on a slide, and dried. The dried vascular frame was then stained with PAS and hematoxylin, and variations in cell walls and nuclei were confirmed.

As a result, as shown in FIG. 8, when the number of acellular capillaries in each group was analyzed, the number of the acellular capillaries was increased by 5-fold in the diabetic group (DM), whereas the metformin-administered group (MET) and the group (MET+FENO) co-administered with metformin and fenofibrate could not prevent the proliferation of the acellular capillaries. However, it was confirmed that when CMO4-100 and CMO4-250, which are the group administered with the extract of cinnamon twig and moutan root bark (1:8), according to the present invention were co-administered with metformin, respectively, these groups of the present invention significantly inhibited the formation of the acellular capillaries (FIG. 8).

6-4 Inhibitory Effect Against Damage to Tight-Junction Protein Between Cells

An inhibitory effect against the damage to a tight junction protein between cells was confirmed after administering CMO4 (extract of cinnamon twig and moutan root bark (1:8)) and CPA4 (extract of cinnamon twig and peony root (1:8)) which were prepared in Examples 1 and 2.

Specifically, eyeballs in mice were enucleated in the same manner as Experimental Example 6-2, and fixed in 10% neutralized formalin overnight. In addition, the resultant was dehydrated and substituted three times with xylene, thereby embedding the same with paraffin. Blocks of the embedded tissue were prepared as serial sections in a thickness of 4 µm, and placed on slides for use. In order to remove an endogenous peroxidase activity, a slide which underwent deparaffinization and function processes was allowed to react with 3% hydrogen peroxide solution for 10 minutes, and then washed three times with PBS containing 0.05% tween 20. In order to remove non-specific reactions, 5% casein was used for blocking, and then primary antibodies were diluted at a ratio of 1:200, respectively. Thereafter, the diluted primary antibodies were treated for one hour or overnight. After washing with PBS for one hour, a labeled streptoavidin biotin (LSAB) kit (Dako, USA) was applied to the resultants, developed with DAB, and then observed using an optical microscope. In the case of fluorescent staining, FITC-conjugated secondary antibodies were diluted at a ratio of 1:200, respectively, and reacted for one hour. Thereafter, the resultants were stained with DAPI and observed using a fluorescence microscope.

Figure 9A:
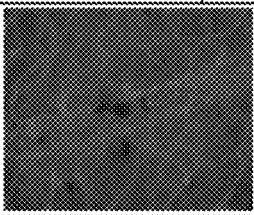
Figure 9A:
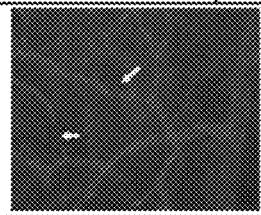
Figure 9A:
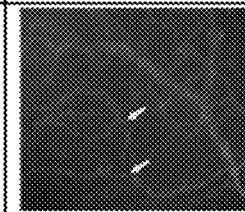
Figure 9A:
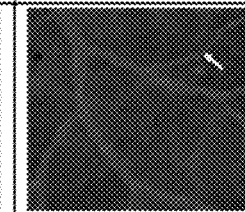
Figure 9A:
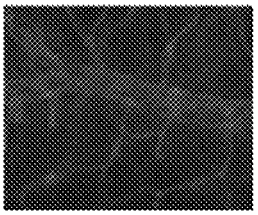
Figure 9A:
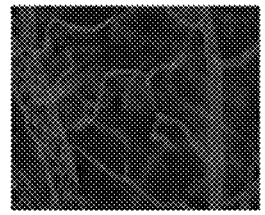
Figure 9A:
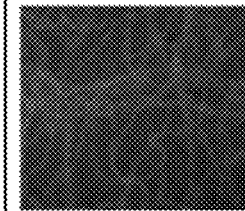
Figure 9A:
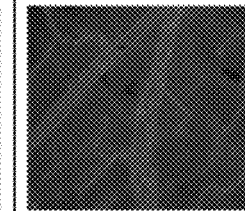
Figure 9B:
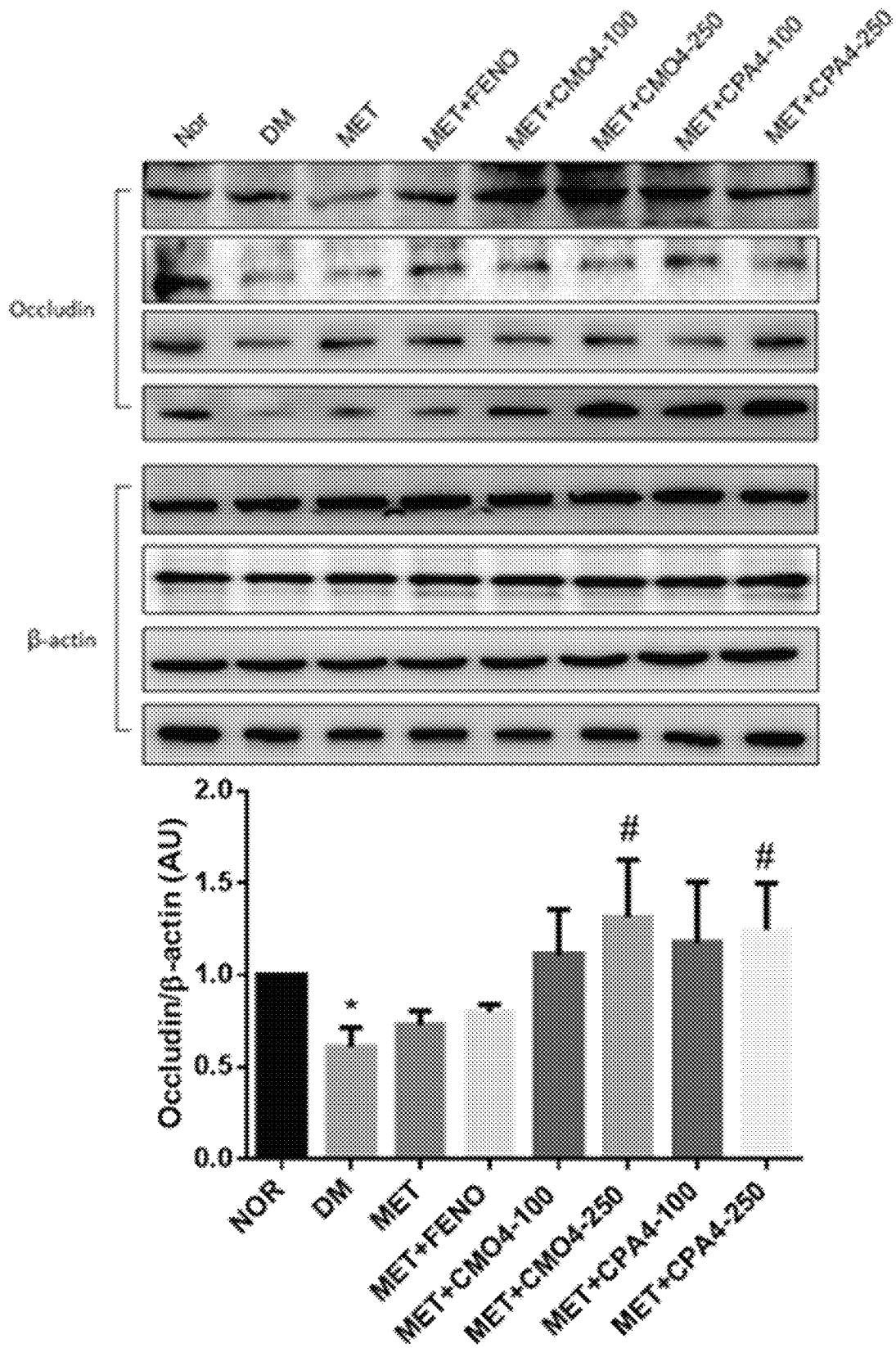

As a result, as shown in FIGS. 9a and 9b, it was confirmed that connection lines such as the threads of claudin-5 were snapped in various regions of blood vessels in the diabetic group (DM), the metformin-administered group (MET), or the group (MET+FENO) co-administered with metformin and fenofibrate. However, when CMO4-100 and CMO4-250, which are the groups administered with the extract of cinnamon twig and moutan root bark (1:8), and CPA4-100 and CPA4-250, which are the groups administered with the extract of cinnamon twig and peony root (1:8), according to the present invention were co-administered with metformin, respectively, there was no claudin-5 loss in these groups (FIG. 9a). In addition, the amount of occludin was significantly reduced in the diabetic group (DM), and there was no significant increase thereof in the metformin-administered group (MET) and in the group (MET+FENO) co-administered with metformin and fenofibrate. However, it was confirmed that when CMO4-250, the group administered with the extract of cinnamon twig and moutan root bark (1:8) and CPA4-250, the group administered with the extract of cinnamon twig and peony root (1:8), according to the present invention were co-administered with metformin, respectively, these groups significantly increased the amount of occludin (FIG. 9b).

6-5 Effect on Renal Function and Proteinuria

In order to confirm an effect of preventing and treating renal function degradation caused by hyperglycemia, 24-hour urine outputs, proteinuria, albuminuria, and creatinine clearance, and amounts of nephrin, 8-OHd, and AGE in urine were confirmed.

As a result, as shown in FIG. 10, amounts of nephrin, 8-OHd, and AGE in urine in all groups showed the significant effect, but amounts of urine and albuminuria and creatinine clearance were not inhibited in the metformin-only administered group. In addition, it was confirmed when CMO4-100 and CMO4-250, which are the groups administered with the extract of cinnamon twig and moutan root bark (1:8), and CPA4-100 and CPA4-250, which are the groups administered with the extract of cinnamon twig and peony root (1:8), according to the present invention were co-administered with metformin, respectively, these groups significantly inhibited the albuminuria and creatinine clearance. However, the effect on the creatinine clearance was not exhibited in MET+FENO, the group co-administered with metformin and fenofibrate (FIG. 10).

Based on the results above, it was confirmed that it is not possible to inhibit progression to diabetic nephropathy by solely administering metformin. However, when the extract of cinnamon twig and moutan root bark, or the extract of cinnamon twig and peony root was co-administered with metformin, it can significantly treat the progression to diabetic nephropathy.

6-6 Change of Glomerulosclerosis

Symptoms of glomerulosclerosis, i.e., mesangial and extracellular matrix expansions, were confirmed by PAS staining and trichrome staining.

As a result, as shown in FIG. 11, in the diabetic group, a symptom of glomerulosclerosis, i.e., enlarged and expanded mesangial regions due to production and accumulation of extracellular matrix substances in a glomerulus, was observed. In addition, it was confirmed that when CMO4-100 and CMO4-250, which are the groups administered with the extract of cinnamon twig and moutan root bark (1:8), and CPA4-100 and CPA4-250, which are the groups administered with the extract of cinnamon twig and peony root (1:8), according to the present invention were co-administered with metformin, respectively, these groups significantly inhibited mesangial and extracellular matrix expansions (FIG. 11).

Experimental Example 7: Therapeutic Effect on Macular Degeneration in Rodent Animal Model 7-1 Effect of Preventing and Treating Macular Degeneration in MNU-Induced Animal Model with Age-Related Macular Degeneration 7-1-1 Experimental Animal Breeding and Experimental Design 6-week-old male C57BL/6 mice were used after purification thereof for one week. Among the morphological changes of retinal tissues which appeared in macular degeneration, 60 mg/kg of 1% (0.05% acetic acid) N-methyl-N-nitrosourea (MNU, Sigma, USA) was intraperitoneally injected into the 7-week-old C57BL/6 mice in order to induce damage and denaturation of photoreceptor cells. The same amount of 0.05% acetic acid was intraperitoneally administered to the normal group. CMO4 and CMO4-1, which are the extracts of cinnamon twig and moutan root bark (1:8), and CPA4-1, which is the extract of cinnamon twig and peony root (1:8), according to the present invention were suspended and prepared in 0.5% sodium carboxymethyl cellulose (CMC), and orally administered once at an exclusive concentration of 50 mg/kg and 100 mg/kg, or 100 mg/kg before the day of administering MNU. Thereafter, the resultants were orally administered once a day for seven days after the MNU administration. In the normal group and MNU-induced group, only 0.5% CMC was orally administered in the same amount.

7-1-2 Histopathological Evaluation

Among the morphological changes of retinal tissues which appeared in macular degeneration, the damage and denaturation of photoreceptor cells were confirmed by change in a thickness of outer nuclear layers in retinal tissues.

Specifically, using the mice prepared in Experimental Example 7-1-1, eyeballs in the mice were enucleated in the same manner as Experimental Example 6-2, and fixed in 10% neutralized formalin overnight. In addition, the resultant was dehydrated and substituted three times with xylene, thereby embedding the same with paraffin. Blocks of the embedded tissue were prepared as serial sections in a thickness of 4 μm, and placed on slides for use. In order to remove an endogenous peroxidase activity, a slide which underwent deparaffinization and function processes was allowed to react with 3% hydrogen peroxide solution for 10 minutes, and then washed three times with PBS containing 0.05% tween 20. The slide sections were stained with Hematoxylin & Eosin, (H&E) and observed with an optical microscope.

As a result, as shown in FIG. 12, it was confirmed that the thickness of outer nuclear layers (*), in which the nuclei of photoreceptor cells were densely formed in the retina, became thin because the number of cells was decreased due to the damage caused by the MNU administration. However, in the groups administered with CMO4 and CMO4-1 (extracts of cinnamon twig and moutan root bark (1:8)), and CPA4-1 (extract of cinnamon twig and peony root (1:8)), the damage to photoreceptor cells which was caused by MNU was significantly inhibited (FIG. 12).

7-2 Effect of Preventing Damage to Retinal Pigment Epithelial Cells in NaIO$_3$-Induced Animal Model 7-2-1 Experimental Animal Breeding and Experimental Design 6-week-old male SD rats were used after purification thereof for one week. 35 mg/kg of 3.5% NaOI$_3$ (Sigma, USA) was intravenously injected under the tongues of the 7-week-old rats in order to induce damage and denaturation of retinal pigment epithelial cells, which is one of the changes which appear in macular degeneration. The same amount of saline was administered to the normal group. CMO4-1, which is the hot water extract of cinnamon twig and moutan root bark (1:8), and CPA4-1, which is the hot water extract of cinnamon twig and peony root (1:8), according to the present invention were suspended and prepared in 0.5% sodium carboxymethyl cellulose (CMC), and orally administered once at a concentration of 50 mg/kg and 100 mg/kg before the day of administering NaOI$_3$. Thereafter, the resultants were orally administered once a day for seven days after the NaOI$_3$ administration. In the normal and control groups, only 0.5% CMC was orally administered in the same amount.

7-2-2 Histopathological Evaluation

The damage and denaturation of retinal pigment epithelial cells, which were one of changes which appeared in macular degeneration, were confirmed by the folding number of outer nuclear layers in retinal tissues.

Specifically, using the mice prepared in Experimental Example 7-2-1, eyeballs in the mice were enucleated as the same manner in Experimental Example 6-2, and fixed in 10% neutralized formalin overnight. In addition, the resultant was dehydrated and substituted three times with xylene, thereby embedding the same with paraffin. Blocks of the embedded tissue were prepared as serial sections in a thickness of 4 µm, and placed on slides for use. In order to remove an endogenous peroxidase activity, a slide which underwent deparaffinization and function processes was allowed to react with 3% hydrogen peroxide solution for 10 minutes, and then washed three times with PBS containing 0.05% tween 20. The slide sections were stained with Hematoxylin & Eosin, (H&E) and observed with an optical microscope.

As a result, as shown in FIG. 13, a phenomenon in which an outer nuclear layer, in which the nuclei of photoreceptor cells located just above epithelial cells were dense, was bent due to damage to the epithelial cells pigmented by the NaOI$_3$-administration was observed with the naked eye. However, in the groups administered with CMO4-1 (hot water extract of cinnamon twig and moutan root bark (1:8)) and CPA4-1 (hot water extract of cinnamon twig and peony root (1:8)), it was confirmed that the damage to pigmented epithelial cells induced by NaOI$_3$ was suppressed in order to significantly inhibit the phenomenon in which an outer nuclear layer is bent (FIG. 13).

7-3 Effect of Preventing Macular Degeneration in Very-Low-Density Lipoprotein Receptor (VLDLR) Knockout Mice 7-3-1 Experimental Animal Breeding and Experimental Design A pair of male and female Vldlr$^{-/-}$ mice, an animal model which has subretinal neovascularization, a clinical symptom of wet macular degeneration, expressed from 3 weeks of age was purchased from Jacson laboratory. In addition, 2-week-old mice were obtained through breeding of the above mice, and then used for the experiment. For the normal animal, C57BL/6 mice having the same age in weeks were used. CMO4, which is the extract of cinnamon twig and moutan root bark (1:8), and CPA4, which is the extract of cinnamon twig and peony root (1:8), according to the present invention were suspended and prepared in 0.5% CMC, and then intraperitoneally administered once a day for seven days at a concentration of 100 mg/kg. In the normal and control groups, only 0.5% CMC was orally administered in the same amount.

7-3-2 Inhibition of Subretinal Neovascularization

Edema of retinal blood vessels was measured to confirm an inhibitory effect against the subretinal neovascularization.

Specifically, using the animal model of Experimental Example 7-3-1, Zoletil 50 (Virbac, 30 mg/kg) and Rompun (Bayer Korea, 10 mg/kg) were mixed at a ratio of 3:2 during an autopsy and diluted by 10-fold to make saline, and then the saline (50 µL) was intraperitoneally injected for anesthesia. After laparotomy, 5 mg of fluorescein isothiocyanate-dextran (FD40S-1G, Sigma) was dissolved in PBS, and the mixture thereof (100 µL) was injected into the heart. After five minutes, the eyeballs were enucleated, and one eyeball was fixed in 10% neutralized formalin for the preparation of retinal tissue sections while the other eyeball was fixed in 4% paraformaldehyde for 10 minutes. Thereafter, retinas were separated therefrom, flat-mounted retinal slides were prepared, and the slides were observed under a fluorescence microscope (BX51, Olympus, Japan).

As a result, as shown in FIG. 14, neovessels were formed in a subretinal area under an outer nuclear layer so that retinal tissues were bent upwardly; this phenomenon was observed in the Vldlr$^{-/-}$ mice. However, such neovascularization was confirmed to be significantly inhibited by administration of CMO4 of the present invention, the extract of cinnamon twig and moutan root bark (1:8) (FIG. 14).

7-3-3 Inhibition Against Damage to Retinal Pigment Epithelial Cells

ZO-1 staining was carried out to confirm the presence or absence of denaturation of morphological structures of retinal pigment epithelial cells.

Specifically, using the animal model of Experimental Example 7-3-1, after separating retinas from the ocular tissues extracted at autopsy, conjunctival tissue was fixed in 4% paraformaldehyde for three hours, washed with PBS, and stirred in PBS containing 5% Triton X-100 and 1% BSA for three hours. After washing the resultant again, lectin (L2140, Sigma) dissolved in PBS at 1 mg/mL was diluted at a ratio of 1:50 and reacted at 4° C. overnight. After washing the resultant for two hours with PBS containing 0.05% tween 20, streptavidin TRITC was diluted at a ratio of 1:500, reacted at 37° C. for four hours, washed with PBS for 30 minutes, and observed using a fluorescence microscope (BX51, Olympus, Japan).

As a result, as shown in FIG. 15, the retinal pigment epithelial cells of the normal mice were stained with ZO-1 so that an aligned shape thereof was observed. Whereas, in the Vldlr$^{-/-}$ mice, sites (arrows) where cells were damaged and neovessels grew to denature were observed. However, it was confirmed that the denaturation of retinal pigment epithelial cells was significantly inhibited by administration of CMO4 of the present invention, the extract of cinnamon twig and moutan root bark (1:8) (FIG. 15).

7-3-4 Inhibitory Effect Against VEGF Expression in Retina

An inhibitory effect against VEGF expression in retinas was confirmed by staining.

Specifically, slide sections were prepared in the same manner as Experimental Example 7-2-2 using the animal model of Experimental Example 7-3-1. The slide sections were stained with H&E, and quantitatively analyzed neovascular lesions in a subretinal area under an optical microscope.

As a result, as shown in FIG. 16, it was confirmed that VEGF, an important factor involved in permeability of neovessels and blood vessels, was excessively expressed (stained by dark purple) in the Vldlr$^{-/-}$ mice, whereas the VEGF expression was significantly inhibited by administration of CMO4 (extract of cinnamon twig and moutan root bark (1:8)) and CPA4 (extract of cinnamon twig and peony root (1:8)) (FIG. 16).

7-4 Effect of Treating Macular Degeneration in Very-Low-Density Lipoprotein Receptor (VLDLR) Knockout Mice 7-4-1 Experimental Animal Breeding and Experimental Design A pair of male and female Vldlr$^{-/-}$ mice, an animal model which has subretinal neovascularization, a clinical symptom of wet macular degeneration, expressed from 3 weeks of age, was purchased from Jacson laboratory. In addition, 2-week-old mice were obtained through breeding of the above mice, and then used for the experiment. For the normal animal, C57BL/6 mice having the same age of the week were used. CMO4, which is the extract of cinnamon twig and moutan root bark (1:8), and CPA4, which is the extract of cinnamon twig and peony root (1:8), according to the present invention were suspended and prepared in 0.5% CMC, and then intraperitoneally administered once a day for seven days at a concentration of 50 mg/kg and 100 mg/kg from 3 weeks of age, respectively. In the normal and control groups, only 0.5% CMC was orally administered in the same amount.

7-4-2 Inhibition of Subretinal Neovascularization

The inhibitory effect of subretinal neovascularization appeared in macular degeneration was confirmed using retinal tissue sections.

Specifically, using the animal model of Experimental Example 7-4-1, the retinal tissue sections were observed in the same manner as Experimental Example 7-3-2 under a fluorescence microscope (BX51, Olympus, Japan).

As a result, as shown in FIG. 17, neovessels were formed in a subretinal area under an outer nuclear layer so that retinal tissues were bent upwardly; this phenomenon was observed in the Vldlr$^{-/-}$ mice. However, such neovascularization was confirmed to be significantly inhibited by administering CMO4 (100 mg/kg) of the present invention, the extract of cinnamon twig and moutan root bark (1:8) (FIG. 17).

7-5 Inhibitory Effect Against Neovascularization in Laser-Induced Choroidal Membrane Neovascular Rat Model 7-5-1 Experimental Animal Breeding and Experimental Design 7-week-old male Long-Evans rats (SLC Japan, Tokyo, Japan) were anesthetized by intraperitoneally injecting Zoletil 50 (Virbac, 30 mg/kg) and Rompun (Bayer Korea, 10 mg/kg). Thereafter, 1% tropicamide eye drops were used to enlarge pupils, and then four photocoagulation spots were formed around an optic nerve head using a diode laser (wavelength: 532 nm, diameter: 100 μm, power: 150 mW, duration: 0.1 sec). Destruction of Bruch's membrane was verified by formation of distinguishing bubbles. The rats awakened from the anesthesia were randomly divided into groups and drugs were administered thereto. CMO4, the extract of cinnamon twig and moutan root bark (1:8), and CPA4, the extract of cinnamon twig and peony root (1:8), according to the present invention were suspended and prepared in 0.5% CMC, and then each extract was orally administered once a day for 10 days at a concentration of 100 mg/kg. In the normal group, only 0.5% CMC was orally administered in the same amount.

7-5-2 Inhibition of Subretinal Neovascularization

An inhibitory effect of subretinal neovascularization which appeared in macular degeneration was confirmed using retinal tissue sections.

Specifically, using the animal model of Experimental Example 7-5-1, after 10 days, the rats were anesthetized by intraperitoneally injecting a mixed solution of Zoletil 50 (Virbac, 30 mg/kg) and Rompun (Bayer Korea, 10 mg/kg) in a ratio of 3:2 at an autopsy. After laparotomy, 5 mg of fluorescein isothiocyanate-dextran (MW 2×10$^6$, Sigma) was dissolved in PBS, and injected the mixture thereof (100 μL) into the heart. After 10 minutes, the eyeballs were enucleated and fixed in 4% paraformaldehyde for 10 minutes. Thereafter, retinas were separated therefrom, and conjunctival tissues containing subretinal area were prepared as flat-mounted slices. The flat-mounted slices were observed under a fluorescence microscope (BX51, Olympus, Japan). A size of neovessels-produced regions was analyzed using Image J software (NIH, USA).

As a result, as shown in FIG. 18, it was confirmed that the neovascularization was significantly inhibited by administration of CMO4 (100 mg/kg) of the present invention, the extract of cinnamon twig and moutan root bark (1:8). In addition, the neovascularization tended to be inhibited by administration of CPA4 (100 mg/kg) of the present invention, the extract of cinnamon twig and peony root (1:8) (FIG. 18).

Experimental Example 8: Effect of Preventing and Treating Macular Degeneration in Rodent Animal Model with MNU-Induced Macular Degeneration As shown in the analysis results of Table 1, it was confirmed that the content of paeoniflorin in the extracts of cinnamon twig and moutan root bark (1:8) (CMO4 and CMO4-1), and the extracts of cinnamon twig and peony root (1:8) (CPA4 and CPA4-1) was 2.7%, 2.3%, 12.3%, and 8.9%, respectively. It was reported that since paeoniflorin has an inhibitory effect on apoptosis caused by $H_2O_2$ in a human retinal pigment epithelial cell line (ARPE-19), the paeoniflorin can effectively be used to treat an ophthalmologic disease, e.g., macular degeneration (Molecular Vision 2011; 17: 3512-3522). However, in the animal model, preventive and therapeutic effects on macular degeneration were not demonstrated, and instead an antioxidant effect and inhibition of apoptosis were merely confirmed after adding $H_2O_2$, a toxic substance which is different from an aging condition, and a general cause of macular degeneration in retinal pigment epithelial cell lines. That is, the effect of paeoniflorin on macular degeneration was not demonstrated in an animal model. Accordingly, in order to demonstrate that although the extracts of the present invention contain paeoniflorin, the effects of the extracts were not merely the sole effects of paeoniflorin, the effects of paeoniflorin contained in each extract (100 mg) were confirmed in an animal model.

8-1 Experimental Animal Breeding and Experimental Design 6-week-old male C57BL/6 mice were used after purification thereof for one week. In order to induce damage and denaturation of photoreceptor cells, among morphological changes of retinal tissues which appeared in macular degeneration, 1% (0.05% acetic acid) N-methyl-N-nitrosourea (MNU, Sigma, USA) was intraperitoneally injected to the 7-week-old male C57BL/6 mice at a concentration of 60 mg/kg. The same amount of 0.05% acetic acid was intraperitoneally administered to the normal group. As the samples, CMO4 (100 mg/kg), which is the extract of cinnamon twig and moutan root bark (1:8), and CPA4 (100 mg/kg), which is the extract of cinnamon twig and peony root (1:8), paeoniflorin -2.7 (2.7 mg/kg), and paeoniflorin -12.3 (12.3 mg/kg) were suspended and prepared in 0.5% CMC and administered orally once before the MNU administration day. After administration of MNU, these resultants were orally administered once a day for seven days, respectively. In the normal and MNU-induced groups, the same amount of 0.5% CMC was orally administered.

8-2 Change in Thickness of Outer Nuclear Layers in Retinal Nerve Tissues

Change in a thickness of outer nuclear layers caused by damage to photoreceptor cells in retinal nerve tissues was confirmed.

Specifically, experimental groups in which the samples were treated in the same manner as Experimental Example 8-1 were autopsied after the administration, and eyeballs were enucleated. Thereafter, the enucleated eyeballs were fixed in 10% neutralized formalin for one day, and embedded with paraffin to prepare slide sections. The slide sections were stained with H&E and observed under an optical microscope.

As a result, as shown in Table 4, the group administered with CMO4, which is the extract of cinnamon twig and moutan root bark (1:8), was proven to have effects 50% higher than the MNU-administered group (1.23±0.20 AU→1.61±0.32 AU). However, it was confirmed that the group (PF-2.7) administered with paeoniflorin contained in CMO4 (100 mg) had no effect at all compared with the MNU-administered group (1.23±0.20 AU→1.23±0.21 AU) (Table 4).

Additionally, as shown in Table 5, the degree of damage to outer nuclear layers in which nuclei of photoreceptor cells are dense in retinas was deteriorated by approximately 50% or more in the MNU-administered group (1.99±0.21 AU→0.92±0.17 AU). However, it was confirmed that the effect was improved by 21.4% in the group administered with CPA4, which is the extract of cinnamon twig and peony root (1:8), compared with the MNU-administered group (0.92±0.17 AU→1.14±0.21 AU). In addition, it was also confirmed that the effect was improved by 17.5% in the group (PF-12.4) administered with paeoniflorin contained in CPA4 (100 mg) (0.92±0.17 AU→1.11±0.19 AU), and that the CPA4-administered group improved the effect by 4% compared with the group (PF-12.4) administered with paeoniflorin (12.4 mg/kg) (Table 5).

TABLE 4

| Experimental group | Thickness of outer nuclear layer (AU) | Thickness of outer nuclear layer (%) |
| --- | --- | --- |
| NOR | 1.99 ± 0.21 | 100.00 ± 27.72 |
| MNU | 1.23 ± 0.20* | 0.00 ± 25.55 |
| CMO4 | 1.61 ± 0.32# | 50.31 ± 42.41 |
| PF-2.7 | 1.23 ± 0.21 | 0.76 ± 27.23 |

(*$p < 0.05$ vs. NOR; #$p < 0.05$ vs. MNU)

TABLE 5

| Experimental group | Thickness of outer nuclear layer (AU) | Thickness of outer nuclear layer (%) |
| --- | --- | --- |
| NOR | 1.99 ± 0.21 | 100.00 ± 10.92 |
| MNU | 0.92 ± 0.17* | 0.57 ± 15.64 |
| CPA4 | 1.14 ± 0.25# | 21.38 ± 23.30 |
| PF-12.4 | 1.11 ± 0.19# | 17.46 ± 17.39 |

(*$p < 0.05$ vs. NOR; #$p < 0.05$ vs. MNU)

Based on the results above, it was confirmed that the effect (2.7%) of CMO4 (extract of cinnamon twig and moutan root bark (1:8)) having a very low content of paeoniflorin is remarkably superior not only because the effect of the extract of cinnamon twig and moutan root bark is not merely caused by paeoniflorin, but because the effect thereof was, in fact, a synergistic effect of numerous ingredients present in the extract of cinnamon twig and moutan root bark. In addition, based on the results of the extract of cinnamon twig and moutan root bark, it was also confirmed that the effect of the extract of cinnamon twig and peony root was not caused by paeoniflorin, but the effect thereof was a synergistic effect of numerous ingredients present in the extract of cinnamon twig and peony root.

Additionally, the superior effect was confirmed in CMO4 or CMO4-1, which is the cinnamon twig and moutan root bark extract having a lower content of paeoniflorin compared with CPA4 or CPA4-1, which is the cinnamon twig and peony root extract; such superior effect thereof was already confirmed in the previous Experimental Examples (FIGS. 13 to 18). These results demonstrated that the effect of the mixed extracts of the present invention was not caused by paeoniflorin, but was a synergistic effect of numerous ingredients present in the mixed extracts.

Experimental Example 9: Effect of Inhibiting and Treating Lower Extremity Edema 9-1 Experimental Animal Breeding and Experimental Design 6-week-old male SD rats were purchased from Orientbio Inc. (Seongnam, Korea), and used after purification thereof for one week. After the purification, the animals were randomly grouped as follows:

Normal: Normal control group; Edema: Lower extremity edema-induced group; CMO4-1-50: Lower extremity edema-induced group+group administered with CMO4-1 (50 mg/kg/day); CMO4-1-100: Lower extremity edema-induced group+group administered with CMO4-1 (100 mg/kg/day); CPA4-1-50: Lower extremity edema-induced group+group administered with CPA4-1 (50 mg/kg/day); and CPA4-1-100: Lower extremity edema-induced group+group administered with CPA4-1 (100 mg/kg/day).

Each group was orally administered once daily from three days before onset of lower extremity edema, pretreated for four days, and then lower extremity edema was induced in the afternoon. CMO4-1, which is the extract of cinnamon twig and moutan root bark (1:8), and CPA4-1, which is the extract of cinnamon twig and peony root (1:8), were prepared by suspending the same in 0.5% CMC. In addition, in the normal and lower extremity edema-induced group, only the same amount of 0.5% CMC was orally administered. Lower extremity edema was induced by administering 2.5% formalin-containing saline (0.1 mL) into a right hind foot of the rats, and only the same amount of saline was injected into the normal group.

9-2 Change in State of Lower Extremity Edema

A state of edema before and after the induction of lower extremity edema was confirmed.

Specifically, with the experimental group of Experimental Example 9-1, increase in the paw volume before the administration of formalin and one hour after the administration thereof was measured using a plethysmometer, an edema-measuring instrument (Ugo Basile, Milan, Italy). The edema index was calculated by the following Equation 3.

$$\text{Edema index (\%)} = \frac{\text{size of foot per hour} - \text{size of foot at 0 hour}}{\text{size of foot at 0 hour}} \times 100 \quad \text{Equation 3}$$

As shown in FIG. 19, as a result of confirming the state of edema before the induction of the edema and one hour after the onset of the edema, there was little increase in the edema size when sterilized saline was injected to the normal group, but a slight increase did occur. Further, it was confirmed that the size was significantly increased by approximately 20% in the lower extremity edema-induced group in which formalin was administered, but such change in the size caused by lower extremity edema was not greatly increased by CMO4-1 (extract of cinnamon twig and moutan root bark (1:8)). Furthermore, it was also confirmed that the size of lower extremity edema was concentration-dependent and significantly inhibited when CPA4-1 (extract of cinnamon twig and peony root (1:8)) was administered (FIG. 19).

Based on the results above, it was confirmed that the preventive and therapeutic effects of the mixed extracts of cinnamon twig and peony root on lower extremity edema were remarkably excellent.

INDUSTRIAL APPLICABILITY

The present invention can be used not only as a composition of a natural mixed extract for preventing and treating diabetic complications and angioedema, but can also effectively be used as a health functional food.

The invention claimed is:

1. A method for treating angioedema, the method comprising administering a pharmaceutically effective amount of a mixed extract consisting of a cinnamon twig extract and a moutan root bark extract to a subject having angioedema, wherein cinnamon twig and moutan root bark are mixed prior to extraction in a weight ratio of 1:1 to 1:8.

2. The method of claim 1, wherein the extract is extracted using water, ethanol, methanol, or a mixture thereof as a solvent.

3. The method of claim 1, wherein the extract is extracted by a high-temperature decompression method, a hot-water extraction method, a reflux extraction method, a hydrothermal extraction method, a maceration extraction method, a room-temperature extraction method, an ultrasonification extraction method, or a steam extraction method.

4. The method of claim 1, wherein the angioedema is any one selected from the group consisting of macular degeneration, macular edema, retinal degeneration, and varicose veins.

5. A method for ameliorating angioedema, the method comprising administering a pharmaceutically effective amount of a mixed extract consisting of a cinnamon twig extract and a moutan root bark extract to a subject having angioedema, wherein cinnamon twig and moutan root bark are mixed prior to extraction in a weight ratio of 1:1 to 1:8.

6. The method of claim 5, wherein the extract is extracted using water, ethanol, methanol, or a mixture thereof as a solvent.

7. The method of claim 5, wherein the extract is extracted by a high-temperature decompression method, a hot-water extraction method, a reflux extraction method, a hydrothermal extraction method, a maceration extraction method, a room-temperature extraction method, an ultrasonification extraction method, or a steam extraction method.

8. The method of claim 5, wherein the angioedema is any one selected from the group consisting of macular degeneration, macular edema, retinal degeneration, and varicose veins.

9. The method of claim 1, wherein the extract is extracted using an ethanol reflux extraction method, and wherein the angioedema is macular degeneration.

10. The method of claim 5, wherein the extract is extracted using an ethanol reflux extraction method, and wherein the angioedema is macular degeneration.

* * * * *